(12) United States Patent
Kurhade et al.

(10) Patent No.: US 11,845,767 B2
(45) Date of Patent: Dec. 19, 2023

(54) ARGINASE INHIBITORS

(71) Applicant: RIJKSUNIVERSITEIT GRONINGEN, Groningen (NL)

(72) Inventors: Santosh Kurhade, Groningen (NL); Alexander Dömling, Groningen (NL)

(73) Assignee: Rijksuniversiteit Groningen, Groningen (NL)

(*) Notice: Subject to any disclaimer, the term of this patent is extended or adjusted under 35 U.S.C. 154(b) by 171 days.

(21) Appl. No.: 17/617,065

(22) PCT Filed: Jun. 15, 2020

(86) PCT No.: PCT/EP2020/066507
§ 371 (c)(1),
(2) Date: Dec. 7, 2021

(87) PCT Pub. No.: WO2020/249821
PCT Pub. Date: Dec. 17, 2020

(65) Prior Publication Data
US 2022/0227791 A1    Jul. 21, 2022

(30) Foreign Application Priority Data
Jun. 14, 2019   (EP) .................................... 19180260

(51) Int. Cl.
*C07F 5/02* (2006.01)
(52) U.S. Cl.
CPC .................................... *C07F 5/025* (2013.01)
(58) Field of Classification Search
CPC ....................................................... C07F 5/025
See application file for complete search history.

(56) References Cited

U.S. PATENT DOCUMENTS

2018/0009830 A1   1/2018   Blaszczyk et al.

FOREIGN PATENT DOCUMENTS

| AU | 2015372690 A1 | 7/2017 |
| CA | 2973474 A1 | 7/2016 |
| CN | 107406464 A | 11/2017 |
| EP | 3240777 A1 | 11/2017 |
| PL | 3240777 T3 | 10/2019 |
| WO | 2016108707 A1 | 7/2016 |

OTHER PUBLICATIONS

M.P.M. van den Berg et al., "Pharmacological Screening Identifies SHK242 and SHK277 as Novel Arginase Inhibitors with Efficacy against Allergen-Induced Airway Narrowing In Vitro and In Vivos" (Journal of Pharmacology and Experimental Therapeutics Apr. 13, 2020, jpet.119.264341; DOI: 10.1124/jpet.119.264341).
Yuanze Wang et al., "Easy Synthesis of Two Positional Isomeric Tetrazole Libraries" (Georg Thieme Verlag Stuttgart, New York—Synthesis 2016, 48, 3701-3712.
Beggio et al. J. Pharmacol. Exp. Ther. 1999, 290, 1409-1416.
International Search Report of PCT/EP2020/066507.
Written Opinion of PCT/EP2020/066507.

*Primary Examiner* — Golam M Shameem
(74) *Attorney, Agent, or Firm* — Fox Rothschild LLP

(57) ABSTRACT

The present invention relates to novel arginase inhibitors of formula (I). These novel compounds are useful in the treatment of diseases that are associated with arginase activity, such as asthma, allergic rhinitis and COPD (chronic obstructive pulmonary disease).

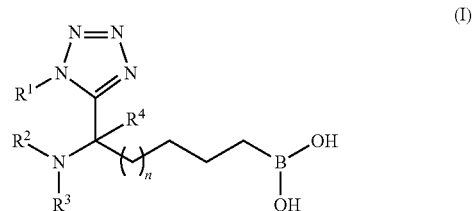

19 Claims, No Drawings

ARGINASE INHIBITORS

CROSS REFERENCE TO RELATED APPLICATIONS

This Application is a U.S. National Stage Entry of the International Patent Application No. PCT/EP2020/066507 filed on Jun. 15, 2020, which claims the benefit of European Patent Application No. 19180260.2, filed on Jun. 14, 2019. The entire contents of these applications are incorporated herein by reference in their entirety.

The present invention relates to novel arginase inhibitors. These novel compounds are useful in the treatment of diseases that are associated with arginase activity, such as asthma, allergic rhinitis and COPD (chronic obstructive pulmonary disease).

Arginase is a manganese-containing enzyme. The reaction catalyzed by this enzyme is: arginine+$H_2$→ornithine+urea. Arginase catalyzes the fifth and final step in the urea cycle, a series of biochemical reactions in mammals during which the body disposes of harmful ammonia.

In most mammals, two isozymes of this enzyme exist; the first, Arginase I, functions in the urea cycle, and is located primarily in the cytoplasm of hepatocytes (liver cells). The second isozyme, Arginase II, has been implicated in the regulation of intracellular arginine/ornithine levels. It is located in mitochondria of several tissues in the body, with most abundance in the kidney and prostate. It may be found at lower levels in macrophages, lactating mammary glands, and brain. The second isozyme may be found in the absence of other urea cycle enzymes.

Allergic asthma is a chronic inflammatory airways' disease, characterized by allergen-induced early and late bronchial obstructive reactions, airway hyperresponsiveness (AHR), airway inflammation and airway remodelling. Recent ex vivo and in vivo studies in animal models and asthmatic patients have indicated that arginase plays a central role in all these features. Thus, increased arginase activity in the airways induces reduced bioavailability of L-arginine to constitutive (cNOS) and inducible (iNOS) nitric oxide synthases, causing a deficiency of bronchodilating and anti-inflammatory NO, as well as increased formation of peroxynitrite, which may be involved in allergen-induced airways obstruction, AHR and inflammation. In addition, both via reduced NO production and enhanced synthesis of L-ornithine, increased arginase activity may be involved in airway remodelling by promoting cell proliferation and collagen deposition in the airway wall. Therefore, arginase inhibitors have therapeutic potential in the treatment of acute and chronic asthma. Boron-containing arginase inhibitors are described in WO 2016/108707 A1. However, so far, no arginase inhibitors are available for therapeutic treatment of asthma.

It has therefore been the object to provide novel arginase inhibitors which may be used for the treatment of diseases that are associated with arginase activity, such as asthma and COPD.

The present invention provides compounds of formula (I):

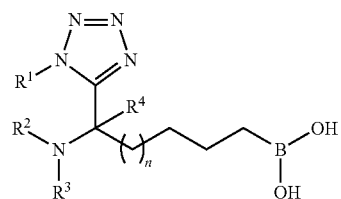

wherein
n is 1 or 2;
$R^1$ is hydrogen or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted;
$R^2$ is hydrogen or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted, and $R^3$ is hydrogen; or
$R^2$ and $R^3$ together are part of an optionally substituted heterocycloalkyl or heteroaryl group; and
$R^4$ is hydrogen or methyl.
or a pharmaceutically acceptable salt, solvate or hydrate or a pharmaceutically acceptable formulation thereof.

According to a preferred embodiment, $R^4$ is hydrogen.

According to a further preferred embodiment, $R^1$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted.

Further preferably, if $R^3$ is hydrogen, also $R^2$ is hydrogen.

Moreover preferably, $R^2$ and $R^3$ together are part of an optionally substituted heterocycloalkyl group comprising 5 or 6 ring atoms selected from C, N, O and S or part of an optionally substituted heteroaryl group comprising 5 or 6 ring atoms selected from C, N, O and S.

Further preferably, n is 1.

Moreover preferably, n is 2.

Further preferably, $R^1$ is a group of formula —$CH_2$—C(=O)—NH—$R^5$, wherein $R^5$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted.

Moreover preferably, $R^1$ is a group of formula —$CH_2$—$CH_2$—C(=O)—NH—$R^5$, wherein $R^5$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted.

Further preferably, $R^1$ is a group of formula —$CH_2$—C(=O)—N($CH_3$)—$R^5$, wherein $R^5$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted.

Moreover preferably, $R^1$ is a group of formula -$L^1$-$Cy^1$-$L^2$-$Cy^2$, wherein $L^1$ and $L^2$ are independently selected from a bond, a $C_{1-4}$ alkyl group or a $C_{1-4}$ heteroalkyl group; $Cy^1$ is a $C_{3-7}$ cycloalkylene group, a heterocycloalkylene group containing from 3 to 7 ring atoms selected from O, S, N and C, a phenylene group or a heteroarylene group containing 5 or 6 ring atoms selected from O, S, N and C, all of which groups may optionally be substituted; and $Cy^2$ is a $C_{3-7}$ cycloalkyl group, a heterocycloalkyl group containing from 3 to 7 ring atoms selected from O, S, N and C, a phenyl group or a heteroaryl group containing 5 or 6 ring atoms selected from O, S, N and C, all of which groups may optionally be substituted.

Especially preferred compounds of formula (I) are compounds of formula (II):

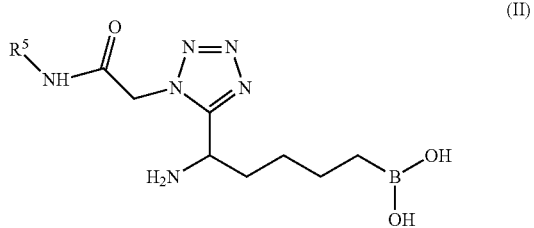

wherein $R^5$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or a pharmaceutically acceptable salt, solvate or hydrate or a pharmaceutically acceptable formulation thereof.

Moreover especially preferred compounds of formula (I) are compounds of formula (III):

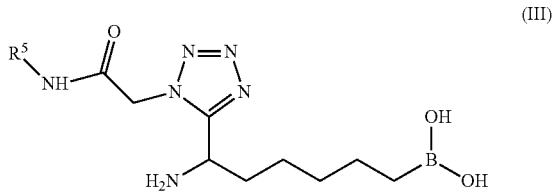

wherein $R^5$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or a pharmaceutically acceptable salt, solvate or hydrate or a pharmaceutically acceptable formulation thereof.

Preferably, $R^5$ is a group of formula —$CH_2$—$R^6$, —$CH_2CH_2$—$R^6$ or —$CH(CH_3)$—$R^6$ wherein $R^6$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted.

Especially preferably, $R^5$ is a group of formula —$CH_2$—$R^6$ or —$CH_2CH_2$—$R^6$; most preferably, $R^5$ is a group of formula —$CH_2$—$R^6$.

Preferably, $R^6$ is a $C_{1-4}$ alkyl, a $C_{2-4}$ alkenyl, a $C_{2-4}$ alkynyl or a $C_{1-4}$ heteroalkyl group.

Further preferably, $R^6$ is selected from the following groups, all of which may optionally be substituted: $C_{3-7}$ cycloalkyl, phenyl, heterocycloalkyl containing from 3 to 7 ring atoms selected from C, N, O and S and heteroaryl containing 5 or 6 ring atoms selected from C, N, O and S.

Moreover preferably, $R^6$ is an optionally substituted phenyl group or an optionally substituted heteroaryl group containing 5 or 6 ring atoms selected from C, N, O and S.

Especially preferably, $R^6$ is a phenyl group or a pyridyl group, all of which may optionally be substituted, especially by one or two F or Cl atoms.

Further especially preferred compounds of formula (I), (II) or (III) are compounds of formula (I), (II) or (III) given in the examples or a pharmaceutically acceptable salt, solvate or hydrate or a pharmaceutically acceptable formulation thereof.

The expression alkyl refers to a saturated, straight-chain or branched hydrocarbon group that contains from 1 to 20 carbon atoms, preferably from 1 to 12 carbon atoms, especially from 1 to 6 (e.g. 1, 2, 3 or 4) carbon atoms, for example a methyl, ethyl, propyl, iso-propyl, n-butyl, iso-butyl, sec-butyl, tert-butyl, n-pentyl, iso-pentyl, n-hexyl, 2,2-dimethylbutyl or n-octyl group. Furthermore, the term alkyl refers to groups in which one or more hydrogen atoms have been replaced by a halogen atom (preferably F or Cl) such as, for example, a 2,2,2-trichloroethyl or a trifluoromethyl group.

The expressions alkenyl and alkynyl refer to at least partially unsaturated, straight-chain or branched hydrocarbon groups that contain from 2 to 20 carbon atoms, preferably from 2 to 12 carbon atoms, especially from 2 to 6 (e.g. 2, 3 or 4) carbon atoms, for example an ethenyl (vinyl), propenyl (allyl), iso-propenyl, butenyl, ethinyl, propinyl, butinyl, acetylenyl, propargyl, isoprenyl or hex-2-enyl group. Preferably, alkenyl groups have one or two (especially preferably one) double bond(s), and alkynyl groups have one or two (especially preferably one) triple bond(s). Furthermore, the terms alkenyl and alkynyl refer to groups in which one or more hydrogen atoms have been replaced by a halogen atom (preferably F or Cl).

The expression heteroalkyl refers to an alkyl, alkenyl or alkynyl group in which one or more (preferably 1, 2 or 3) carbon atoms have been replaced by an oxygen, nitrogen, phosphorus, boron, selenium, silicon or sulfur atom (preferably by an oxygen, sulfur or nitrogen atom) or a group of formula SO or $SO_2$. Accordingly, the expression heteroalkyl also refers to a carboxylic acid or to a group derived from a carboxylic acid, such as, for example, acyl, acylalkyl, alkoxy-carbonyl, acyloxy, acyloxyalkyl, carboxyalkylamide or alkoxycarbonyloxy. Furthermore, the term heteroalkyl refers to groups in which one or more hydrogen atoms have been replaced by a halogen atom (preferably F or Cl).

Preferably, a heteroalkyl group contains from 1 to 12 carbon atoms and from 1 to 4 hetero atoms selected from oxygen, nitrogen and sulphur (especially oxygen and nitrogen). Especially preferably, a heteroalkyl group contains from 1 to 6 (e.g. 1, 2, 3 or 4) carbon atoms and 1, 2 or 3 (especially 1 or 2) hetero atoms selected from oxygen, nitrogen and sulphur (especially oxygen and nitrogen). The term $C_{1-6}$ heteroalkyl refers to a heteroalkyl group containing from 1 to 6 carbon atoms and 1, 2 or 3 heteroatoms selected from O, S and/or N (especially O and/or N). The term $C_{1-4}$ heteroalkyl refers to a heteroalkyl group containing from 1 to 4 carbon atoms and 1, 2 or 3 heteroatoms selected from O, S and/or N (especially O and/or N).

Examples of heteroalkyl groups are groups of formulae:
$R^a$—O—$Y^a$—, $R^a$—S—$Y^a$—, $R^a$—SO—$Y^a$—, $R^a$—$SO_2$—$Y^a$—, $R^a$—N($R^b$)—$SO_2$—$Y^a$—, $R^a$—$SO_2$—N($R^b$)—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N ($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ being a hydrogen atom, a $C_1$-$C_6$ alkyl, a $C_2$-$C_6$ alkenyl or a $C_2$-$C_6$ alkynyl group; $R^b$ being a hydrogen atom, a $C_1$-$C_6$ alkyl, a $C_2$-$C_6$ alkenyl or a $C_2$-$C_6$ alkynyl group; $R^c$ being a hydrogen atom, a $C_1$-$C_6$ alkyl, a $C_2$-$C_6$ alkenyl or a $C_2$-$C_6$ alkynyl group; $R^d$ being a hydrogen atom, a $C_1$-$C_6$ alkyl, a $C_2$-$C_6$ alkenyl or a $C_2$-$C_6$ alkynyl group and $Y^a$ being a direct bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by fluorine or chlorine atoms. Preferred examples of heteroalkyl groups are groups of formulae: $R^a$—O—$Y^a$—, $R^a$—S—$Y^a$—, $R^a$—SO—$Y^a$—, $R^a$—SO$_2$—$Y^a$—, $R^a$—N($R^b$)—SO$_2$—$Y^a$—, $R^a$—SO$_2$—N($R^b$)—$Y^a$—, $R^a$—N($R^b$)—$Y^a$—, $R^a$—CO—$Y^a$—, $R^a$—O—CO—$Y^a$—, $R^a$—CO—N($R^b$)—$Y^a$—, $R^a$—N($R^b$)—CO—$Y^a$—, $R^a$—O—CO—N($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$— and $R^a$—N($R^b$)—C(=N$R^d$)—N($R^c$)—$Y^a$—.

Specific examples of heteroalkyl groups are methoxy, trifluoromethoxy, ethoxy, n-propyloxy, isopropyloxy, butoxy, tert-butyloxy, methoxymethyl, ethoxymethyl, —CH$_2$CH$_2$OH, —CH$_2$OH, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, isopropyl-ethylamino, methylamino methyl, ethylamino methyl, diisopropylamino ethyl, methylthio, ethylthio, isopropylthio, enol ether, dimethylamino methyl, dimethylamino ethyl, acetyl, propionyl, butyryloxy, acetyloxy, methoxycarbonyl, ethoxycarbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile, isonitrile, cyanate, thiocyanate, isocyanate, isothiocyanate and alkylnitrile groups.

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, =O, SH, =S, NH$_2$, =NH, N$_3$ or NO$_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group. Preferably, the expression cycloalkyl refers to a saturated cyclic group that contains one or more rings (preferably 1 or 2), and from 3 to 14 ring carbon atoms, especially preferably from 3 to 10 (more especially preferably 3, 4, 5, 6 or 7) ring carbon atoms.

The expression heterocycloalkyl refers to a cycloalkyl group as defined above in which one or more (preferably 1, 2, 3 or 4) ring carbon atoms have been replaced by an oxygen, nitrogen, silicon, selenium, phosphorus or sulfur atom (preferably by an oxygen, sulfur or nitrogen atom). A heterocycloalkyl group has preferably 1 or 2 ring(s) containing from 3 to 10 (especially 3, 4, 5, 6 or 7) ring atoms (preferably selected from C, O, N and S). The expression heterocycloalkyl refers furthermore to groups that may be substituted by one or more fluorine, chlorine, bromine or iodine atoms or by one or more OH, =O, SH, =S, NH$_2$, =NH, N$_3$ or NO$_2$ groups. Examples are a piperidyl, prolinyl, imidazolidinyl, piperazinyl, morpholinyl, urotropinyl, pyrrolidinyl, tetrahydrothiophenyl, tetrahydropyranyl, tetrahydrofuryl or 2-pyrazolinyl group and also lactames, lactones, cyclic imides and cyclic anhydrides.

The expression alkylcycloalkyl refers to groups that contain both cycloalkyl and also alkyl, alkenyl or alkynyl groups in accordance with the above definitions, for example alkylcyclo-alkyl, cycloalkylalkyl, alkylcycloalkenyl, alkenylcycloalkyl and alkynylcycloalkyl groups. An alkylcycloalkyl group preferably contains a cycloalkyl group that contains one or two rings having from 3 to 10 (especially 3, 4, 5, 6 or 7) ring carbon atoms, and one or two alkyl, alkenyl or alkynyl groups (especially alkyl groups) having 1 or 2 to 6 carbon atoms.

The expression heteroalkylcycloalkyl refers to alkylcycloalkyl groups as defined above in which one or more (preferably 1, 2, 3, 4 or 5) carbon atoms have been replaced by an oxygen, nitrogen, silicon, selenium, phosphorus or sulfur atom (preferably by an oxygen, sulfur or nitrogen atom). A heteroalkylcycloalkyl group preferably contains 1 or 2 rings having from 3 to 10 (especially 3, 4, 5, 6 or 7) ring atoms, and one or two alkyl, alkenyl, alkynyl or heteroalkyl groups (especially alkyl or heteroalkyl groups) having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and hetero-alkylheterocycloalkenyl, the cyclic groups being saturated or mono-, di- or tri-unsaturated.

The expression aryl refers to an aromatic group that contains one or more rings and from 5 or 6 to 14 ring carbon atoms, preferably from 5 or 6 to 10 (especially 6) ring carbon atoms. The expression aryl refers furthermore to groups in which one or more hydrogen atoms have been replaced by fluorine, chlorine, bromine or iodine atoms or by OH, SH, NH$_2$, N$_3$ or NO$_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings and from 5 to 14 ring atoms, preferably from 5 to 10 (especially 5 or 6 or 9 or 10) ring atoms (preferably selected from O, S, N and C), and contains one or more (preferably 1, 2, 3, 4 or 5) oxygen, nitrogen, phosphorus or sulfur ring atoms (preferably O, S or N). The expression heteroaryl refers furthermore to groups in which one or more hydrogen atoms have been replaced by fluorine, chlorine, bromine or iodine atoms or by OH, SH, N$_3$, NH$_2$ or NO$_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, oxazolyl, isoxazolyl, triazolyl, tetrazolyl, isoxazolyl, indazolyl, indolyl, benzimidazolyl, benzoxazolyl, benzisoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression aralkyl refers to groups containing both aryl and also alkyl, alkenyl, alkynyl and/or cycloalkyl groups in accordance with the above definitions, such as, for example, aryl-alkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic ring systems (1 or 2 rings) containing from 6 to 10 carbon atoms and one or two alkyl, alkenyl and/or alkynyl groups containing from 1 or 2 to 6 carbon atoms and/or one or two cycloalkyl groups containing 5 or 6 ring carbon atoms.

The expression heteroaralkyl refers to an aralkyl group as defined above in which one or more (preferably 1, 2, 3 or 4) carbon atoms have been replaced by an oxygen, nitrogen, silicon, selenium, phosphorus, boron or sulfur atom (preferably oxygen, sulfur or nitrogen), that is to say to groups containing both aryl or heteroaryl, respectively, and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (1 or 2 rings) containing from 5 or 6 to 10 ring carbon atoms and one or two alkyl, alkenyl and/or alkynyl groups containing 1 or 2 to 6 carbon atoms and/or one or two cycloalkyl groups containing 5 or 6 ring carbon atoms, wherein 1, 2, 3, 4, 5 or 6 of these carbon atoms have been replaced by oxygen, sulfur or nitrogen atoms.

Examples are arylheteroalkyl, arylheterocycloalkyl, arylheterocycloalkenyl, arylalkyl-heterocycloalkyl, arylalkenylheterocycloalkyl, arylalkynylheterocycloalkyl, arylalkylhetero-cycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, hetero-arylheterocycloalkenyl, heteroarylalkylcycloalkyl, heteroarylalkylheterocycloalkenyl, hetero-arylheteroalkylcycloalkyl, heteroarylheteroalkylcycloalkenyl and heteroarylheteroalkylhetero-cycloalkyl groups, the cyclic groups being saturated or mono-, di- or tri-unsaturated. Specific examples are a tetrahydroisoquinolinyl, benzoyl, 2- or 3-ethylindolyl, 4-methylpyridino, 2-, 3- or 4-methoxyphenyl, 4-ethoxyphenyl, 2-, 3- or 4-carboxyphenylalkyl group.

The term halogen or halogen atom refers to F, Cl, Br or I.

The expression "optionally substituted" preferably refers to groups in which one, two, three or more hydrogen atoms may have been replaced by fluorine, chlorine, bromine or iodine atoms or by OH, =O, SH, =S, $NH_2$, =NH, $N_3$ or $NO_2$ groups. This expression refers furthermore to groups that may be substituted by one, two, three or more (preferably unsubstituted) $C_1$-$C_{10}$ alkyl, $C_2$-$C_{10}$ alkenyl, $C_2$-$C_{10}$ alkynyl, $C_1$-$C_{10}$ heteroalkyl, $C_3$-$C_{18}$ cycloalkyl, $C_2$-$C_{17}$ heterocycloalkyl, $C_4$-$C_{20}$ alkylcycloalkyl, $C_2$-$C_{19}$ heteroalkylcycloalkyl, $C_6$-$C_{18}$ aryl, $C_1$-$C_{17}$ heteroaryl, $C_7$-$C_{20}$ aralkyl or $C_2$-$C_{19}$ heteroaralkyl groups. This expression refers furthermore especially to groups that may be substituted by one, two, three or more (preferably unsubstituted) $C_1$-$C_6$ alkyl, $C_2$-$C_6$ alkenyl, $C_2$-$C_6$ alkynyl, $C_1$-$C_6$ heteroalkyl, $C_3$-$C_{10}$ cycloalkyl, $C_2$-$C_9$ heterocycloalkyl, $C_7$-$C_{12}$ alkylcycloalkyl, $C_2$-$C_{11}$ heteroalkylcycloalkyl, $C_6$-$C_{10}$ aryl, $C_1$-$C_9$ heteroaryl, $C_7$-$C_{12}$ aralkyl or $C_2$-$C_{11}$ heteroaralkyl groups.

If a substituent contains a ring, this ring may be bonded to the respective substituted group via a single or double bond (especially a single bond) or, if the substituted group also contains a ring, the ring of the substituent may also be annulated to the ring of the substituted group.

Preferred substituents are F, Cl, Br, I, OH, =O, $NH_2$, $NO_2$, $C_{1-4}$ alkyl (e.g. —$CH_3$, $CF_3$), $C_{1-4}$ heteroalkyl (e.g. —CN, —OMe), cyclopropyl and $SO_2NH_2$.

Especially preferred substituents are F, Cl, Br, OH, =O, $NH_2$, $CH_2NH_2$, $NO_2$, Me, Ethyl, $NMe_2$, NHMe, $CONH_2$, OMe, $OCF_3$, CN and $CF_3$. The most preferred substituents are F and Cl.

According to a preferred embodiment, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may optionally be substituted.

When an aryl, heteroaryl, cycloalkyl, alkylcycloalkyl, heteroalkylcycloalkyl, heterocycloalkyl, aralkyl or heteroaralkyl group contains more than one ring, these rings may be bonded to each other via a single or double bond or these rings may be annulated.

The present invention further provides pharmaceutical compositions comprising one or more compounds of formula (I), (II) or (III) as defined herein or a pharmaceutically acceptable ester, prodrug, hydrate, solvate or salt thereof, optionally in combination with a pharmaceutically acceptable carrier.

It is a further object of the present invention to provide a compound of formula (I), (II) or (III) as defined herein or a pharmaceutical composition as defined herein for the preparation of a medicament for the treatment of one or more diseases associated with arginase activity.

Preferably the compounds of the present invention may be used for the treatment and/or prevention of asthma (e.g. acute and chronic asthma), COPD, allergic rhinitis, erectile dysfunction, pulmonary hypertension, hypertension, T cell dysfunction, atherosclerosis, renal disease, ischemia reperfusion injury, neurodegenerative diseases, wound healing, inflammatory diseases, fibrotic diseases and cancer.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage may be adjusted to the individual requirements in each particular case including the specific compound being administered, the route of administration, the condition being treated, as well as the patient being treated.

Examples of pharmacologically acceptable salts of sufficiently basic compounds of formula (I), (II) or (III) are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound of formula (I), (II) or (III) may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of formula (I), (II) or (III). Compounds of formula (I), (II) or (III) may be solvated, especially hydrated. The hydratization/hydration may occur during the process of production or as a consequence of the hygroscopic nature of the initially water free compounds of formula (I), (II) or (III). The solvates and/or hydrates may e.g. be present in solid or liquid form.

It should be appreciated that certain compounds of formula (I), (II) or (III) or may have tautomeric forms from which only one might be specifically mentioned or depicted in the following description, different geometrical isomers (which are usually denoted as cis/trans isomers or more generally as (E) and (Z) isomers) or different optical isomers as a result of one or more chiral carbon atoms (which are usually nomenclatured under the Cahn-Ingold-Prelog or R/S system). All these tautomeric forms, geometrical or optical isomers (as well as racemates and diastereomers) and polymorphous forms are included in the invention. Since the compounds of formula (I), (II) or (III) may contain asymmetric C-atoms, they may be present either as achiral compounds, mixtures of diastereomers, mixtures of enantiomers or as optically pure compounds. The present invention comprises both all pure enantiomers and all pure diastereomers, and also the mixtures thereof in any mixing ratio.

The therapeutic use of compounds according to formula (I), (II) or (III), their pharmacologically acceptable salts, solvates and hydrates, respectively, as well as formulations and pharmaceutical compositions also lie within the scope of the present invention.

The pharmaceutical compositions according to the present invention comprise at least one compound of formula (I), (II) or (III) as an active ingredient and, optionally, carrier substances and/or adjuvants.

The present invention also relates to pro-drugs which are composed of a compound of formula (I), (II) or (III) and at least one pharmacologically acceptable protective group which will be cleaved off under physiological conditions, such as an alkoxy-, arylalkyloxy-, acyl-, acyloxymethyl group (e.g. pivaloyloxymethyl), an 2-alkyl-, 2-aryl- or 2-arylalkyl-oxycarbonyl-2-alkylidene ethyl group or an acyloxy group as defined herein, e.g. ethoxy, benzyloxy, acetyl or acetyloxy or, especially for a compound of formula (I), (II) or (III), carrying a hydroxy group (—OH): a sulfate, a phosphate (—OPO$_3$ or —OCH$_2$OPO$_3$) or an ester of an amino acid.

Preferably, the present invention also relates to a prodrug, a biohydrolyzable ester, a biohydrolyzable amide, a polymorph, tautomer, stereoisomer, metabolite, N-oxide, biohydrolyzable carbamate, biohydrolyzable ether, physiologically functional derivative, atropisomer, or in vivo-hydrolysable precursor, diastereomer or mixture of diastereomers, chemically protected form, affinity reagent, complex, chelate and a stereoisomer of the compounds of formula (I), (II) or (III).

As used herein, the term pharmaceutically acceptable ester especially refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

As mentioned above, therapeutically useful agents that contain compounds of formula (I), (II) or (III), their solvates, salts or formulations are also comprised in the scope of the present invention. In general, compounds of formula (I), (II) or (III) will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 10 mg to about 10,000 mg, preferably from about 20 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

EXAMPLES

Example 1: Pent-4-en-1-yl acetate

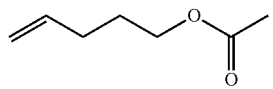

To a solution of 1-Pentenol (20 g, 232 mmol) in CH$_2$Cl$_2$ (100 mL) was added Et$_3$N (65 mL, 464 mmol) and DMAP (0.68 g, 5.5 mmol). The mixture was cooled to 0° C. using an ice bath and acetic anhydride (25 mL, 255 mmol) was added drop wise. The mixture was stirred at RT for 1 hour. The mixture was diluted using CH$_2$Cl$_2$ (100 mL) and washed with water (2×100 mL), 1N aqueous HCl (100 mL), brine (100 mL). The organic layer was collected and dried over MgSO4, filtered and concentrated under reduced pressure to obtain the pent-4-en-1-yl acetate (27 g, 90% yield) as a colorless oil.

¹H NMR (400 MHz, Chloroform-d) δ5.83-5.78 (m, 1H), 5.06-4.90 (m, 2H), 4.07 (t, J=6.7 Hz, 2H), 2.15-2.10 (m, 2H), 2.04 (d, J=3.2 Hz, 3H), 1.76-1.70 (m, 2H); ¹³C NMR (126 MHz, CDCl3) δ171.1, 137.6, 115.4, 64.0, 30.1, 28.0, 21.0.

Example 2: 5-(4,4,5,5-tetramethyl-1,3,2-dioxaborolan-2-yl)pentyl acetate

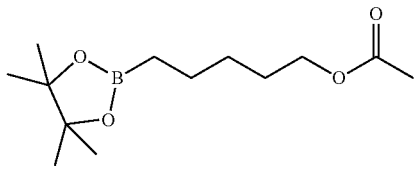 [SMILES: CC(=O)OCCCCCB1OC(C)(C)C(C)(C)O1]

To a solution of the chloro(1,5-cyclooctadiene)iridium(I) dimer (395 mg, 0.6 mmol) and ethylenebis(diphenylphosphine) (492 mg, 1.2 mmol) in 50 mL was added the Pent-4-en-1-yl acetate (5.5 g, 43 mmol, obtained in example 1) and pinacolborane (6.0 g, 47 mmol). The mixture was stirred for 20 h. and then quenched using 10 mL MeOH, washed with water (2×50 mL), brine (50 mL), dried over MgSO4, filtered and concentrated under reduced pressure to obtain the crude product 11.5 g crude product as a yellow oil. The crude product was purified by flash chromatography yielding 5-(4,4,5,5-tetramethyl-1,3,2-dioxaborolan-2-yl) pentyl acetate (7.8 g, 83% yield) of as a colorless oil.

¹H NMR (500 MHz, CDCl3) δ4.06 (t, J=6.8 Hz, 2H), 2.07-2.01 (m, 3H), 1.68-1.59 (m, 2H), 1.48-1.42 (m, 2H), 1.39-1.35 (m, 2H), 1.26-1.25 (s, 12H), 0.79 (t, J=7.7 Hz, 2H) ppm; ¹³C NMR (126 MHz, CDCl3) δ83.1, 64.8, 28.7, 28.6, 25.0, 24.7, 23.8, 21.1.

Example 3: 5-(4,4,5,5-tetramethyl-1,3,2-dioxaborolan-2-yl)pentan-1-ol

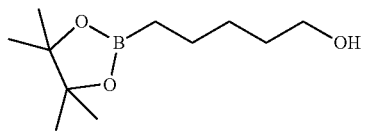

To a solution of the 5-(4,4,5,5-tetramethyl-1,3,2-dioxaborolan-2-yl)pentyl acetate (11 g, 43 mmol, obtained in example 2) in EtOH (150 mL) was added powdered K₂CO₃ (11.3 g, 82 mmol). After 20 hours of stirring at RT, the solvent was removed under reduced pressure. The resultant mixture was re-dissolved in EtOAc (100 mL), washed with water (100 mL), brine (100 mL), dried over MgSO₄, filtered and concentrated under reduced pressure to obtain 13 g crude product. Further purification was performed by flash chromatography to obtain 5-(4, 4, 5, 5-tetramethyl-1,3,2-dioxaborolan-2-yl)pentan-1-ol (6.7 g, 77% yield) as a slightly yellow oil.

¹H NMR (500 MHz, Chloroform-d) δ3.62 (t, J=6.6 Hz, 1H), 1.59-1.54 (m, 2H), 1.46-1.41 (m, 2H), 1.39-1.34 (m, 2H) 1.25 (s, 12H), 0.79 (t, J=7.6 Hz, 2H); ¹³C NMR (126 MHz, Chloroform-d) δ 83.1, 64.7, 28.7, 28.5, 24.9, 24.7, 23.8, 21.1.

Example 4: 5-(4,4,5,5-tetramethyl-1,3,2-dioxaborolan-2-yl)pentanal

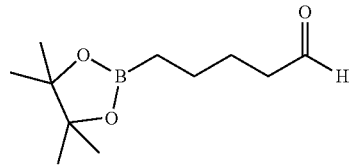

Oxalyl chloride (3.2 mL, 38 mmol) was dissolved in CH₂Cl₂ and cooled to −78° C. DMSO (8.9 mL, 125 mmol) was dissolved in DCM (9.0 mL) and added drop wise. After 15 minutes of stirring, the 5-(4,4,5,5-tetramethyl-1,3,2-dioxaborolan-2-yl)pentan-1-ol (6.7 g, 31 mmol, obtained in example 3) was dissolved in CH₂Cl₂ (10 mL) and drop wise added to the reaction mixture and stirred for 40 minutes. Et₃N (26.2 mL, 188 mmol) was added slowly and the mixture was allowed to warm slowly to room temperature. The mixture was diluted with CH₂Cl₂ (100 mL) and poured onto ice-water (100 mL). The mixture was washed with water (2×50 mL), brine (3×50 mL), dried over MgSO4, filtered and concentrated under reduced pressure to obtain 12 g crude product. The product 5-(4,4,5,5-tetramethyl-1,3,2-dioxaborolan-2-yl)pentanal was afforded by flash chromatography purification yielding 4.6 g (69% yield) as a slightly yellow oil.

Example 5: 5-(4,4,5,5-tetramethyl-1,3,2-dioxaborolan-2-yl)pentanal

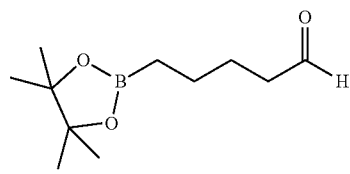

To a stirred solution of 5-(4,4,5,5-tetramethyl-1,3,2-dioxaborolan-2-yl)pentan-1-ol (5 g, 21.91 mmol, obtained in example 3) was dissolved in CH₂Cl₂ (50 mL) was added pyridinium chlorochromate (PCC) (7.08 g, 32.87 mmol) in portion wise over the period of 0.5 h. The resulted reaction mixture was further stirred for 1 h at room temperature. Reaction mixture was diluted with DCM (50 mL) and filtered through pad of silica and the solvent was removed under reduced pressure to obtain 5-(4,4,5,5-tetramethyl-1,3, 2-dioxaborolan-2-yl)pentanal (4.0 g). ¹H NMR (500 MHz, Chloroform-d) δ9.76 (s, 1H), 2.44-2.40 (m, 2H), 1.68-1.61 (m, 2H), 1.50-1.43 (m, 2H), 1.25 (s, 12H), 0.82-0.78 (m, 2H) ppm; ¹³C NMR (126 MHz, Chloroform-d) δ203.1, 83.1, 83.0, 43.9, 24.9, 24.8, 24.7, 23.8.

Examples 6 and 7 were prepared in analogous manner of example 5, starting from appropriates intermediates.

| Example No. | IUPAC name |
|---|---|
| 6 | 6-(4,4,5,5-tetramethyl-1,3,2-dioxaborolan-2-yl)hexanal |
| 7 | 4-(4,4,5,5-tetramethyl-1,3,2-dioxaborolan-2-yl)butanal |

Example 8: (1-(4-chlorobenzyl)piperidin-4-yl)methanamine hydrochloride

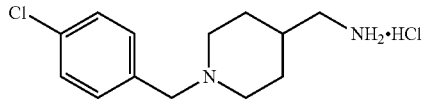

To a stirred solution of tert-butyl (piperidin-4-ylmethyl)carbamate (1.0 g, 4.67 mmol) and 4-chlorobenzaldehyde (0.85 g, 6.07 mmol) in dichloroethane (10 mL) was added glacial acetic acid (0.03 mL, 0.467 mmol) and stirred for 1.5 h. Subsequently, sodium triacetoxyborohydride (2.47 g, 11.67 mmol) was added in portions over the period of 1 h. and the reaction mixture was further stirred for 18 h. To the reaction mixture was added DCM (20 mL) and aqueous saturated sodium bicarbonate solution (15 mL). The organic layer was separated and washed with brine (20 mL), dried over MgSO4, filtered and concentrated under reduced pressure to obtain the tert-butyl ((1-(4-chlorobenzyl)piperidin-4-yl)methyl)carbamate (1.05 g). $^1$H NMR (500 MHz, Chloroform-d) δ7.30-7.19 (m, 4H), 4.58 (br. s, 1H), 3.43 (s, 2H), 3.01 (t, J=6.4 Hz, 2H), 2.84 (dt, J=11.9, 3.3 Hz, 2H), 1.92 (td, J=11.6, 2.5 Hz, 2H), 1.69-1.60 (m, 2H), 1.43 (s, 9H), 1.25 (tt, J=11.9, 6.0 Hz, 2H); MS (EI) m/z: 339.2 (M+H)$^+$ The tert-butyl ((1-(4-chlorobenzyl)piperidin-4-yl)methyl)carbamate (1.0 g) was dissolved in 1,4-dioxane (3.0 mL) and 4N HCl/dioxane (3.0 mL) was added. The reaction mixture was further stirred for 16 h. The solvent was removed under reduced pressure and to the residue was added diethyl ether (10 mL) and the solid product (1-(4-chlorobenzyl)piperidin-4-yl)methanamine hydrochloride (1.05 g) was collected by filtration.

Example 9: N-((1-(4-chlorobenzyl)piperidin-4-yl)methyl)formamide

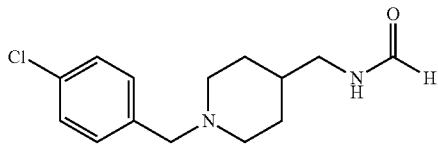 [SMILES: O=CNCC1CCN(Cc2ccc(Cl)cc2)CC1]

To a stirred suspension of (1-(4-chlorobenzyl)piperidin-4-yl)methanamine hydrochloride (1.0 g) in ethyl formate (10 mL) was added triethyl amine (2.0 mL) and the resulted reaction mixture was refluxed for 16 h. The solvent was removed under reduced pressure and the residue was dissolved in ethyl acetate (20 mL). The organic layer was washed with H$_2$O (10 mL) and brine (10 mL), dried over MgSO4, filtered and concentrated under reduced pressure to obtain the N-((1-(4-chlorobenzyl)piperidin-4-yl)methyl)formamide (0.45 g) as a pale yellow solid. $^1$H NMR (500 MHz, Chloroform-d) δ8.18 (s, 1H), 7.31-7.19 (m, 4H), 5.65 (s, 1H), 3.44 (s, 2H), 3.19 (t, J=6.5 Hz, 2H), 2.85 (dt, J=12.1, 3.6 Hz, 2H), 1.93 (td, J=11.7, 2.5 Hz, 2H), 1.73-1.63 (m, 2H), 1.60-1.47 (m, 1H), 1.35-1.17 (m, 2H); MS (EI) m/z: 267.2 (M+H)$^+$.

Example 9: N-(2-aminoethyl)-4-chlorobenzamide hydrochloride

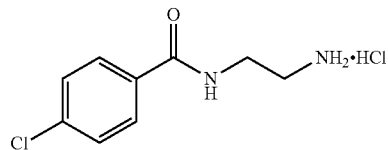

To a cooled solution of tert-butyl (2-aminoethyl)carbamate (1.5 g, 9.36 mmol) and triethylamine (2.60 mL, 18.72 mmol) in dichloromethane (20 mL) was added dropwise 4-chlorobenzoyl chloride (1.31 mL, 10.30 mmol) and stirred for 2.0 h. Reaction mixture was quenched by addition of H$_2$O and the organic layer was separated and washed with brine (10 mL), dried over MgSO4, filtered and concentrated under reduced pressure to obtain the tert-butyl (2-(4-chlorobenzamido)ethyl)carbamate (2.3 g). MS (EI) m/z: 299.2 (M+H)$^+$. The tert-butyl (2-(4-chlorobenzamido)ethyl)carbamate (2.3 g) was dissolved in 1,4-dioxane (10.0 mL) and 4N HCl/dioxane (10 mL) was added. The reaction mixture was further stirred for 16 h. The solvent was removed under reduced pressure and to the residue diethyl ether (10 mL) was added and the product N-(2-aminoethyl)-4-chlorobenzamide hydrochloride was collected by filtration as a white solid (2.0 g).

Example 10: 4-chloro-N-(2-formamidoethyl)benzamide

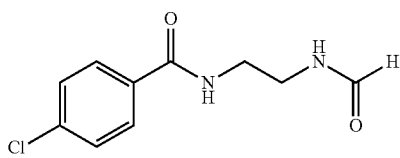 [SMILES: O=CNCCNC(=O)c1ccc(Cl)cc1]

To a stirred suspension of (N-(2-aminoethyl)-4-chlorobenzamide hydrochloride (2.3 g) in ethyl formate (20 mL) was added triethyl amine (3.0 mL) and the resulted reaction mixture was refluxed for 16 h. The solvent was removed under reduced pressure and the residue was dissolved in ethyl acetate (30 mL). The organic layer was washed with H$_2$O (10 mL) and brine (10 mL), dried over MgSO4, filtered and concentrated under reduced pressure to obtain the 4-chloro-N-(2-formamidoethyl)benzamide (2.0 g).

$^1$H NMR (500 MHz, Chloroform-d) δ8.22 (s, 1H), 7.81 (d, J=8.5 Hz, 2H), 7.64 (br. s, 1H), 7.38 (d, J=8.6 Hz, 2H), 7.04 (br. s, 1H), 3.63-3.57 (m, 2H), 3.57-3.51 (m, 2H); MS (EI) m/z: 227.1 (M+H)$^+$.

Examples 11-58 were either obtained from corresponding commercial source or prepared as per literature methods.

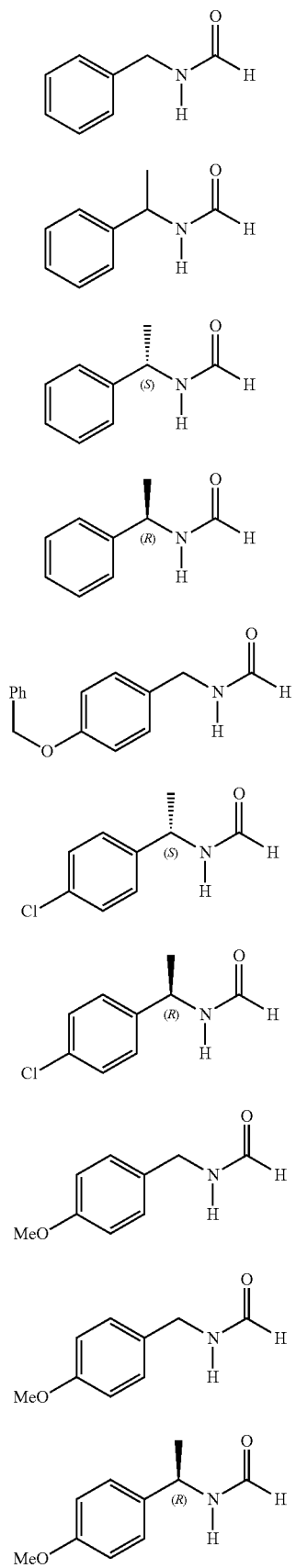
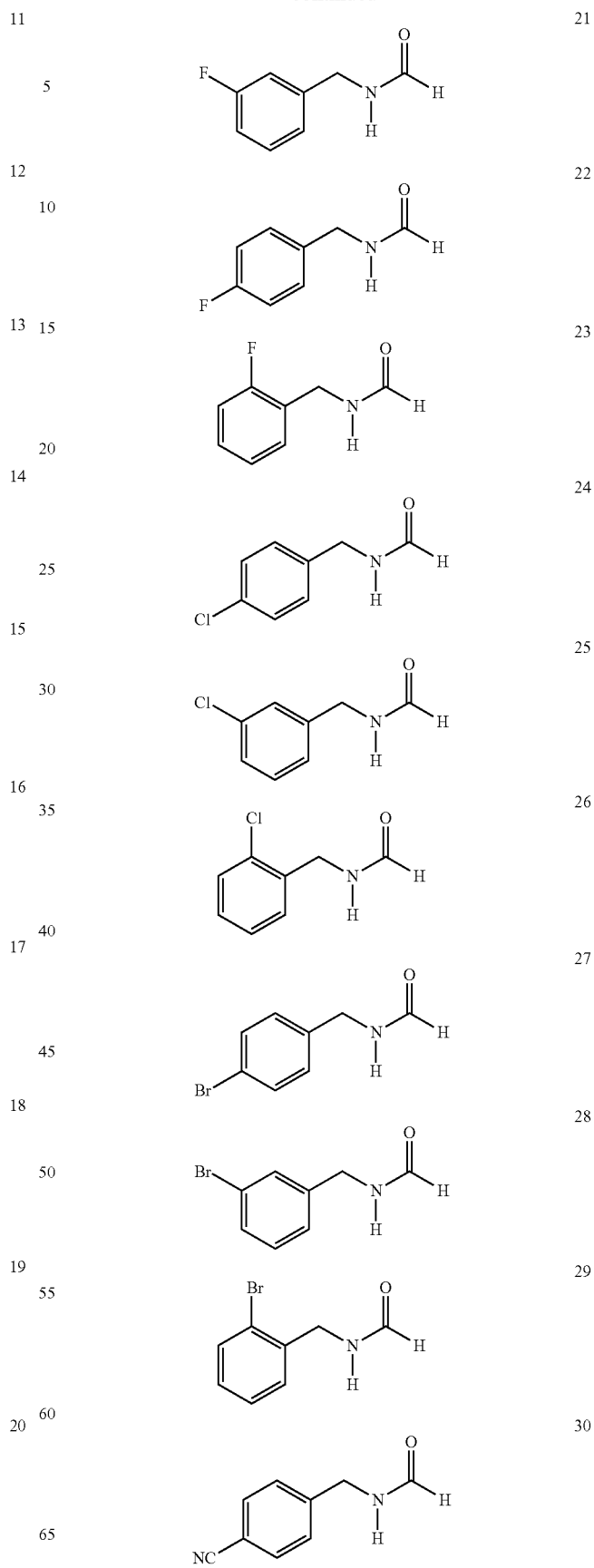

-continued
| | |
|---|---|
| 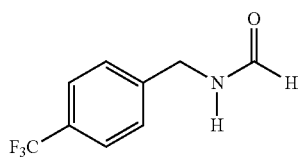 | 31 |
| 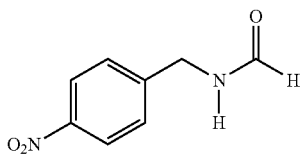 | 32 |
| 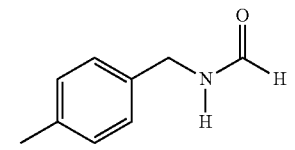 | 33 |
| 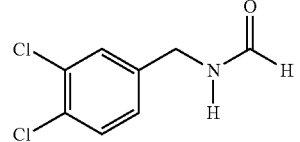 | 34 |
| 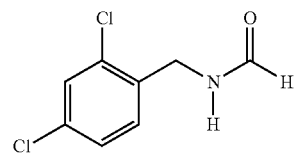 | 35 |
| 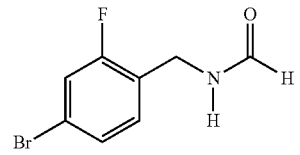 | 36 |
|  | 37 |
| 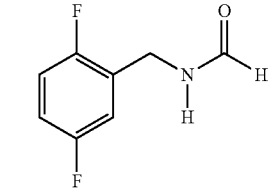 | 38 |
| 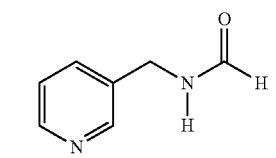 | 39 |
-continued
| | |
|---|---|
| 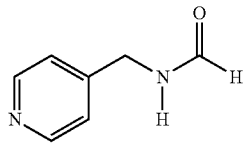 | 40 |
| 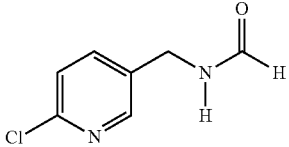 | 41 |
| 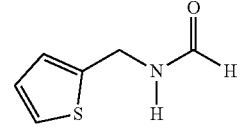 | 42 |
| 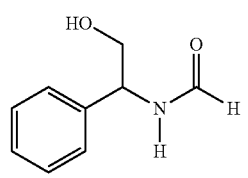 | 43 |
| 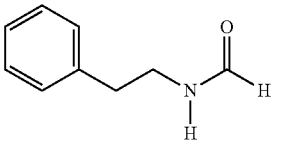 | 44 |
| 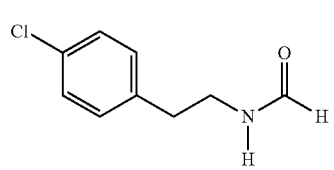 | 45 |
| 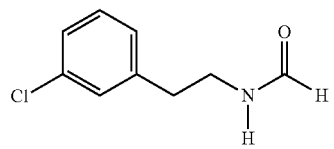 | 46 |
| 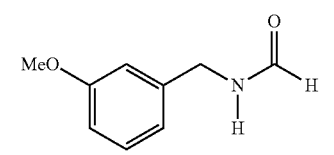 | 47 |
| 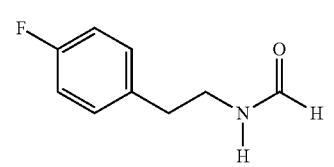 | 48 |
| | 49 |

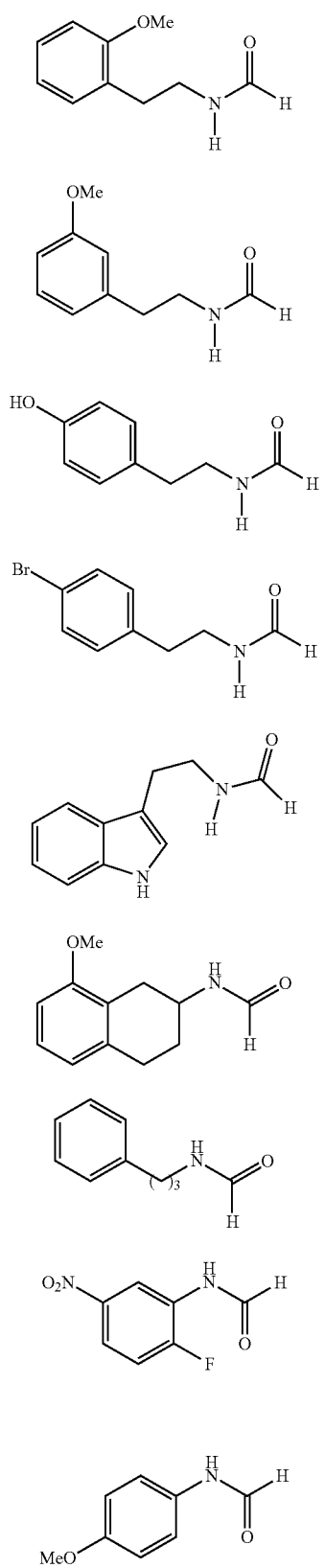
Examples 59a-59t were either obtained from corresponding commercial source or prepared as per literature methods.

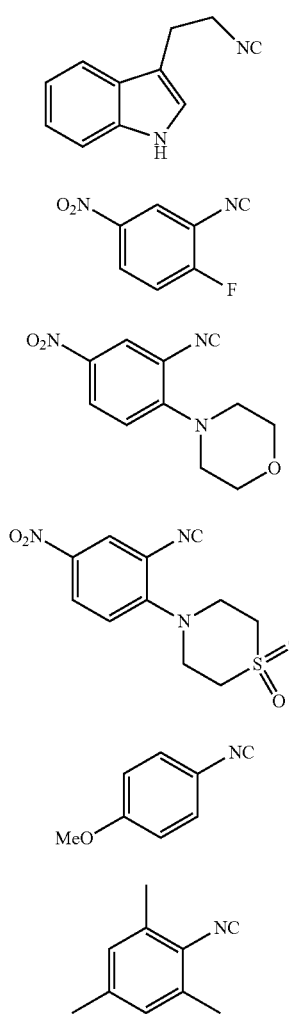
Example 60: N-benzyl-2-isocyanoacetamide
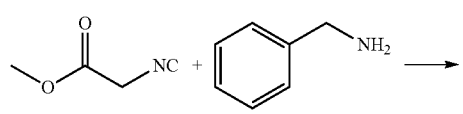
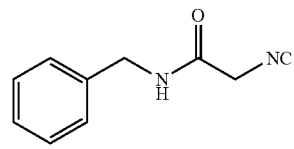
Synthesized as described in *Synthesis* 2016, 48, 3701-3712.
Examples 61-121 were prepared in analogous manner of example 60.
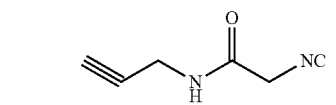

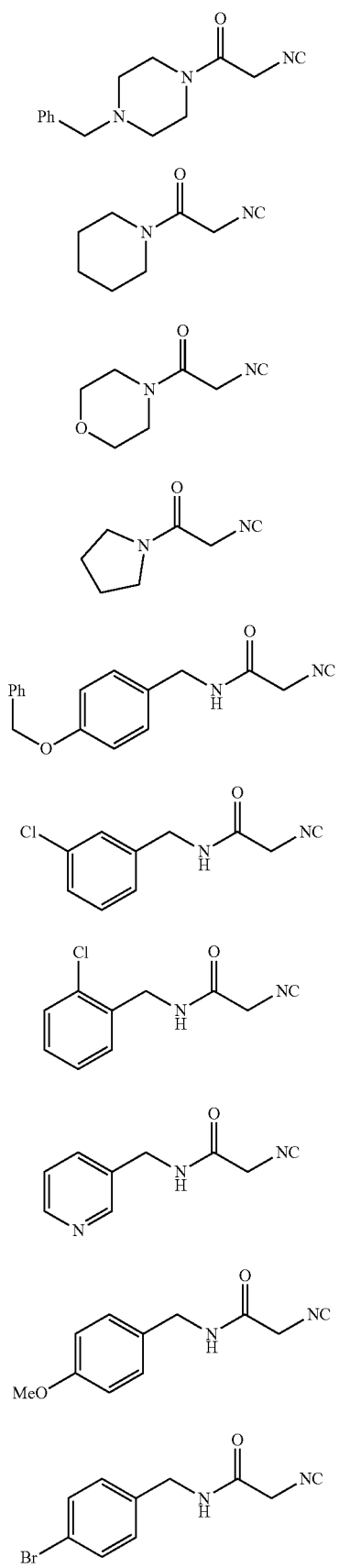
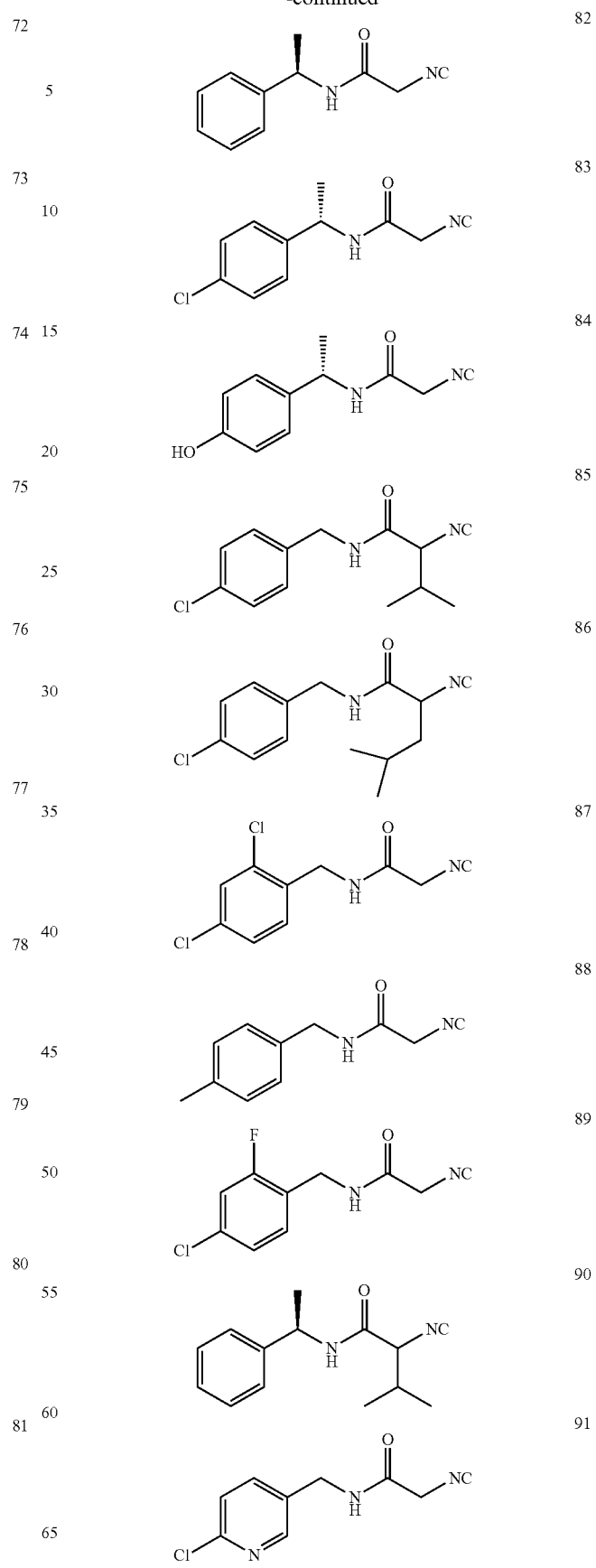

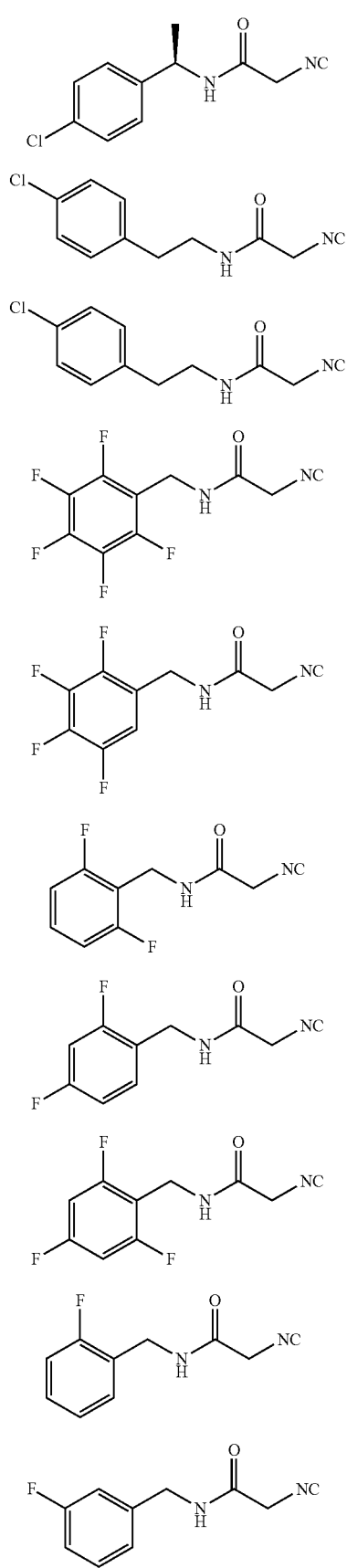
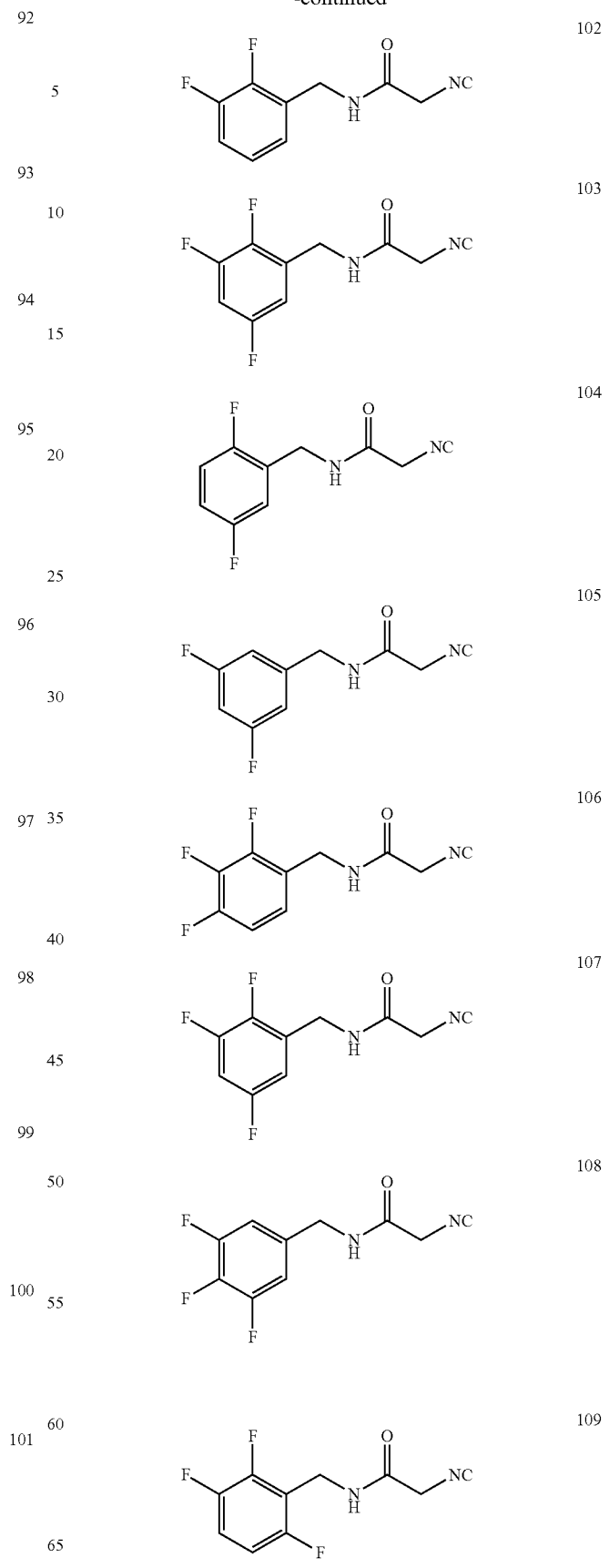

-continued
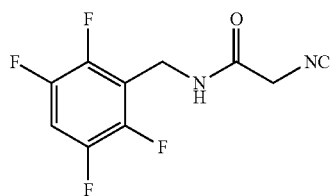
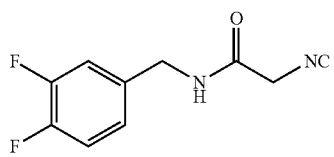
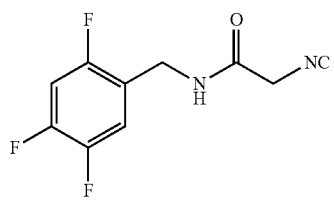
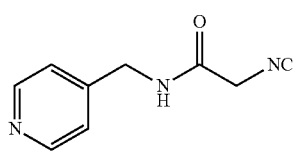
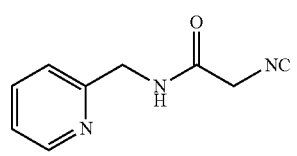
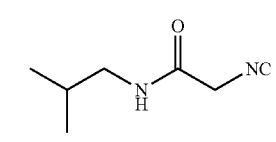
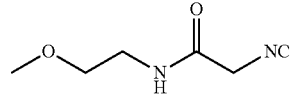
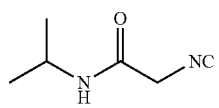
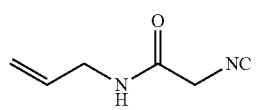
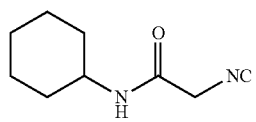
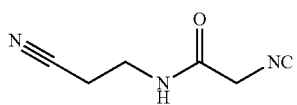
-continued
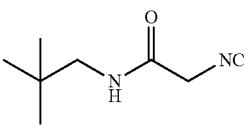
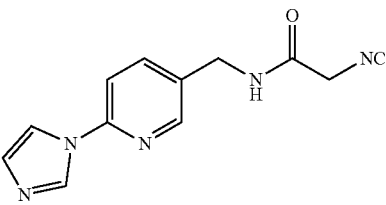
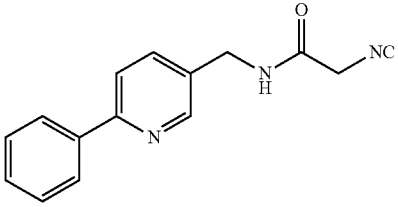
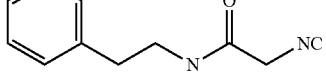
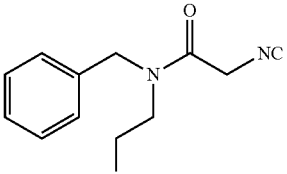
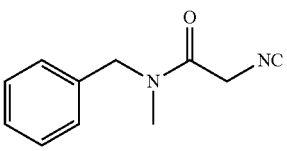
Example 127: N-benzyl-3-isocyanopropanamide
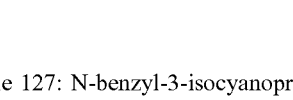
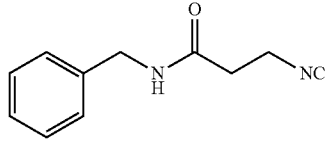
Synthesized as described in *Synthesis* 2016, 48, 3701-3712 by stirring methyl 3-isocyanopropanoate (1.0 mmol) and benzyl amine (1.0 mmol) at room temperature for 48 h.
$^1$H NMR (500 MHz, Chloroform-d) δ7.38-7.32 (m, 2H), 7.32-7.27 (m, 3H), 5.96 (s, 1H), 4.46 (d, J=5.7 Hz, 2H), 3.74 (tt, J=8.5, 4.7, 1.9 Hz, 2H), 2.58 (tt, J=6.8, 2.0 Hz, 2H).

Examples 128a-128c were prepared in analogous manner of preparation 127.

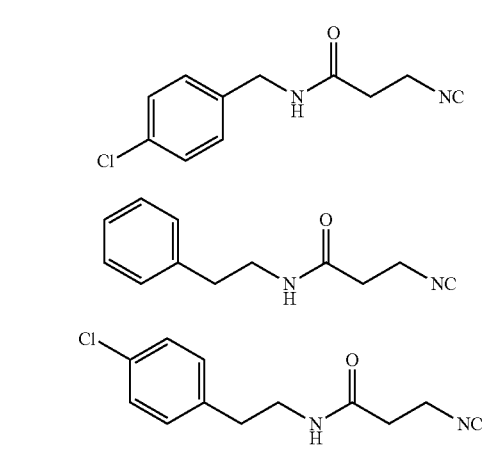

Example 129: 1-(1-(4-chlorobenzyl)-1H-tetrazol-5-yl)-5-(4,4,5,5-tetramethyl-1,3,2-dioxaborolan-2-yl)-N-tritylpentan-1-amine

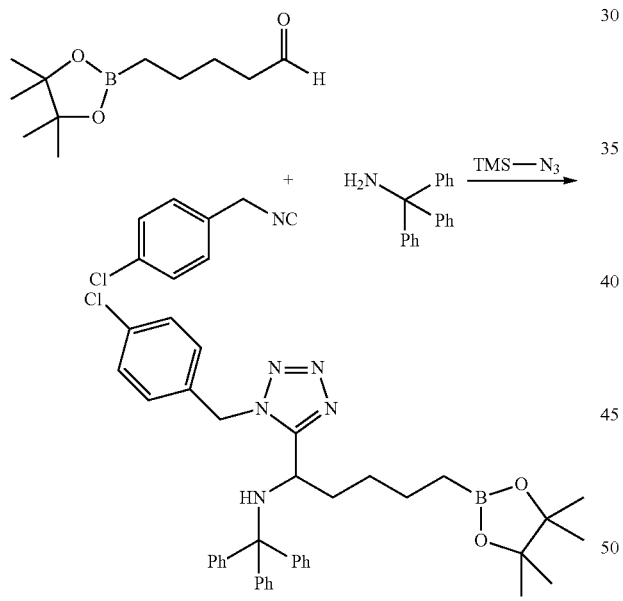

To a stirred solution of 5-(4,4,5,5-tetramethyl-1,3,2-dioxaborolan-2-yl)pentanal (0.25 g, 1.17 mmol) in methanol (2.0 mL) was added tritylamine (0.297 g, 1.17 mmol) and stirred for 0.5 h. Subsequently 1-chloro-4-(isocyanomethyl)benzene (0.16 mL, 1.17 mmol) and azidotrimethylsilane (0.15 mL, 1.17 mmol) were added and further stirred for 16 h. The solvent was removed under reduced pressure and the residue was purified using flash chromatography to provide 1-(1-(4-chlorobenzyl)-1H-tetrazol-5-yl)-5-(4,4,5,5-tetramethyl-1,3,2-dioxaborolan-2-yl)-N-tritylpentan-1-amine (0.45 g).

$^1$H NMR (500 MHz, Chloroform-d) δ7.41-7.34 (m, 6H), 7.30-7.25 (m, 2H), 7.24-7.14 (m, 9H), 6.98 (d, J=8.4 Hz, 2H), 4.97 (q, J=252.5, 15.5 Hz, 2H), 3.97 (td, J=7.8, 5.1 Hz, 1H), 2.86 (d, J=8.0 Hz, 1H), 1.60-1.50 (m, 1H), 1.44-1.32 (m, 1H), 1.21 (s, 12H), 1.20-1.07 (m, 2H), 0.91 (tdd, J=20.3, 12.4, 8.2 Hz, 2H), 0.55 (td, J=7.5, 1.7 Hz, 2H); LC-MS (EI) m/z: 670.3 (M+Na)$^+$.

Example 130: 1-(1-(2-fluoro-5-nitrophenyl)-1H-tetrazol-5-yl)-5-(4,4,5,5-tetramethyl-1,3,2-dioxaborolan-2-yl)-N-tritylpentan-1-amine

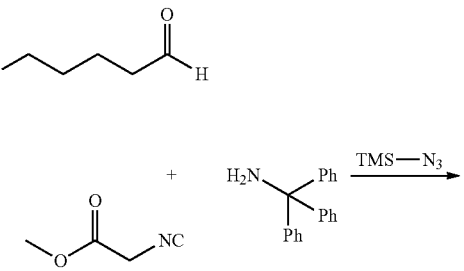

To a stirred solution of 5-(4,4,5,5-tetramethyl-1,3,2-dioxaborolan-2-yl)pentanal (0.25 g, 1.17 mmol) in methanol (2.0 mL) was added tritylamine (0.297 g, 1.17 mmol) and stirred for 0.5 h. Subsequently 1-fluoro-2-isocyano-4-nitrobenzene (0.195 g, 1.17 mmol) and azidotrimethylsilane (0.15 mL, 1.17 mmol) were added and further stirred for 16 h. The solvent was removed under reduced pressure and the residue was purified using flash chromatography to provide 1-(1-(2-fluoro-5-nitrophenyl)-1H-tetrazol-5-yl)-5-(4,4,5,5-tetramethyl-1,3,2-dioxaborolan-2-yl)-N-tritylpentan-1-amine (0.41 g).

$^1$H NMR (500 MHz, Chloroform-d) δ8.47 (dd, J=8.9, 2.5 Hz, 1H), 7.52 (s, 1H), 7.42 (d, J=8.9 Hz, 1H), 7.26-7.20 (m, 6H), 7.20-7.14 (m, 9H), 3.88-3.77 (m, 1H), 2.54 (d, J=5.6 Hz, 1H), 1.64-1.52 (m, 1H), 1.46-1.35 (m, 1H), 1.19 (s, 12H), 1.16-0.94 (m, 4H), 0.58 (t, J=7.5 Hz, 2H); LC-MS (EI) m/z: 685.3 (M+Na)$^+$.

Example 131: Methyl 2-(5-(5-(4,4,5,5-tetramethyl-1,3,2-dioxaborolan-2-yl)-1-(tritylamino)pentyl)-1H-tetrazol-1-yl)acetate

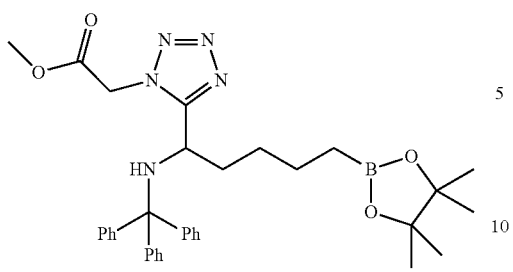

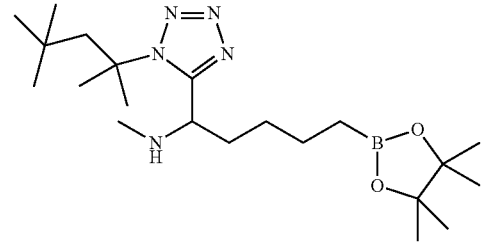

To a stirred solution of 5-(4,4,5,5-tetramethyl-1,3,2-dioxaborolan-2-yl)pentanal (0.25 g, 1.17 mmol) in methanol (2.0 mL) was added tritylamine (0.297 g, 1.17 mmol) and stirred for 0.5 h. Subsequently methyl 2-isocyanoacetate (0.1 mL, 1.17 mmol) and azidotrimethylsilane (0.15 mL, 1.17 mmol) were added and further stirred for 16 h. The solvent was removed under reduced pressure and the residue was purified using flash chromatography to provide methyl 2-(5-(5-(4,4,5,5-tetramethyl-1,3,2-dioxaborolan-2-yl)-1-(tritylamino)pentyl)-1H-tetrazol-1-yl)acetate (0.42 g).

$^1$H NMR (500 MHz, Chloroform-d) δ7.35-7.29 (m, 6H), 7.24-7.13 (m, 9H), 4.69 (q, J=348.1, 17.6 Hz, 2H), 4.05-3.97 (m, 1H), 3.72 (s, 3H), 2.85 (d, J=6.6 Hz, 1H), 1.84 (dq, J=13.3, 8.0 Hz, 1H), 1.69 (dtd, J=13.1, 7.7, 5.1 Hz, 1H), 1.34-1.28 (m, 2H), 1.21 (s, 12H), 1.19-1.13 (m, 2H), 0.69 (t, J=7.8 Hz, 2H); LC-MS (EI) m/z: 618.3 (M+Na)$^+$.

Example 132: methyl 4-(5-(5-(4,4,5,5-tetramethyl-1,3,2-dioxaborolan-2-yl)-1-(tritylamino)pentyl)-1H-tetrazol-1-yl)butanoate The compound of example 132 was obtained by similar method described in example 131. $^1$H NMR (500 MHz, Chloroform-d) δ7.41-7.36 (m, 6H), 7.22-7.16 (m, 6H), 7.16-7.10 (m, 3H), 3.92 (td, J=8.1, 4.8 Hz, 1H), 3.83 (dt, J=14.4, 7.4 Hz, 1H), 3.77-3.68 (m, 1H), 3.66 (s, 3H), 2.95 (d, J=8.2 Hz, 1H), 2.33 (td, J=6.9, 1.6 Hz, 2H), 2.05-1.95 (m, 2H), 1.93-1.83 (m, 1H), 1.72-1.61 (m, 1H), 1.38-1.27 (m, 2H), 1.20 (s, 12H), 1.16-1.03 (m, 2H), 0.69 (dd, J=8.5, 7.1 Hz, 2H); LC-MS (EI) m/z: 646.3 (M+Na)$^+$.

Example 133: N-methyl-5-(4,4,5,5-tetramethyl-1,3,2-dioxaborolan-2-yl)-1-(1-(2,4,4-trimethylpentan-2-yl)-1H-tetrazol-5-yl)pentan-1-amine

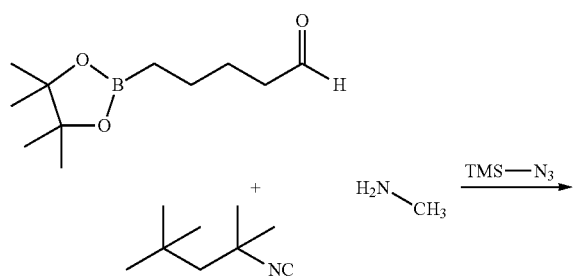

To a stirred solution of 5-(4,4,5,5-tetramethyl-1,3,2-dioxaborolan-2-yl)pentanal (0.25 g, 1.17 mmol) in methanol (2.0 mL) was added methyl amine (40% solution in methanol, 0.09 mL, 1.17 mmol) and stirred for 0.5 h. Subsequently tert-Octylisocyanide (0.2 mL, 1.17 mmol) and azidotrimethylsilane (0.15 mL, 1.17 mmol) were added and further stirred for 16 h. The solvent was removed under reduced pressure and the residue was purified using flash chromatography to provide N-methyl-5-(4,4,5,5-tetramethyl-1,3,2-dioxaborolan-2-yl)-1-(1-(2,4,4-trimethylpentan-2-yl)-1H-tetrazol-5-yl)pentan-1-amine (0.2 g).

$^1$H NMR (500 MHz, Chloroform-d) δ4.08 (dd, J=8.0, 5.2 Hz, 1H), 2.30 (s, 3H), 1.97 (q, J=27.3, 15.4 Hz, 2H), 1.89-1.75 (m, 7H), 1.61-1.52 (m, 1H), 1.50-1.30 (m, 4H), 1.22 (s, 11H), 0.84 (s, 9H), 0.77 (t, J=7.6 Hz, 2H); LC-MS (EI) m/z: 430.3 (M+Na)$^+$.

Example 134: 1-(1-benzyl-1H-tetrazol-5-yl)-N-(4-methoxybenzyl)-5-(4,4,5,5-tetramethyl-1,3,2-dioxaborolan-2-yl)pentan-1-amine

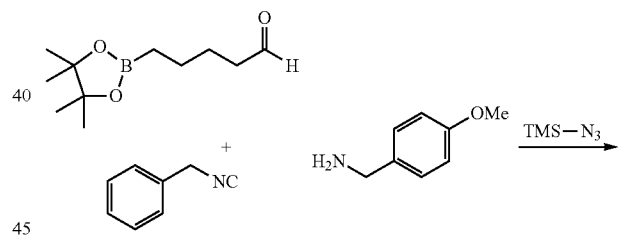

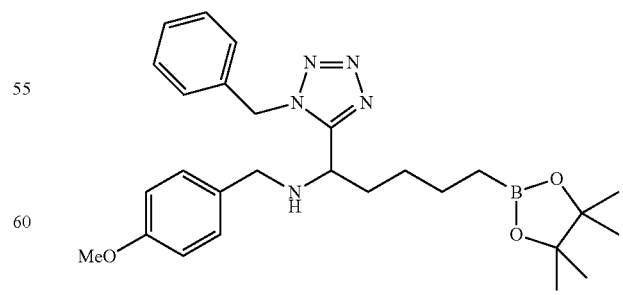

The compound of example 134 was obtained by similar method described in example 133. LC-MS (EI) m/z: 514.3 (M+Na)$^+$.

Example 135: N-(4-methoxybenzyl)-2-(1-(2,4,4-trimethylpentan-2-yl)-1H-tetrazol-5-yl)hex-5-en-2-amine

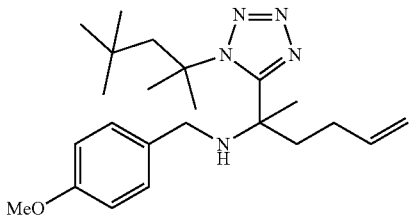 [SMILES: C=CCCC(C)(NCc1ccc(OC)cc1)c1nnnn1C(C)(C)CC(C)(C)C]

To a stirred solution of hex-5-en-2-one (0.25 g, 2.54 mmol) in methanol (1.0 mL) was added (4-methoxyphenyl)methanamine (0.32 mL, 2.54 mmol) and stirred for 1 h. Subsequently tert-Octylisocyanide (0.445 mL, 2.54 mmol) and azidotrimethylsilane (0.33 mL, 2.54 mmol) were added and further stirred for 16 h. The solvent was removed under reduced pressure and the residue was purified using flash chromatography to provide N-(4-methoxybenzyl)-2-(1-(2,4,4-trimethylpentan-2-yl)-1H-tetrazol-5-yl)hex-5-en-2-amine (0.75 g).

$^1$H NMR (500 MHz, Chloroform-d) δ7.24 (d, J=8.6 Hz, 2H), 6.86 (d, J=8.6 Hz, 2H), 5.82 (ddt, J=16.9, 10.1, 6.5 Hz, 1H), 5.01 (dd, J=17.1, 1.7 Hz, 1H), 4.96 (dd, J=10.2, 1.7 Hz, 1H), 3.79 (s, 3H), 3.68 (dd, J=27.4, 11.5 Hz, 2H), 2.36 (ddd, J=13.7, 11.7, 4.8 Hz, 1H), 2.23 (ddd, J=13.7, 11.6, 4.9 Hz, 1H), 2.13-2.06 (m, 2H), 1.97 (dd, J=27.7, 10.3 Hz, 6H), 1.87 (d, J=15.0 Hz, 1H), 1.81-1.74 (m, 1H), 1.72 (s, 3H), 0.65 (s, 9H); LC-MS (EI) m/z: 422.3 (M+Na)$^+$.

Example 136: N-(4-methoxybenzyl)-6-(4,4,5,5-tetramethyl-1,3,2-dioxaborolan-2-yl)-2-(1-(2,4,4-trimethylpentan-2-yl)-1H-tetrazol-5-yl)hexan-2-amine

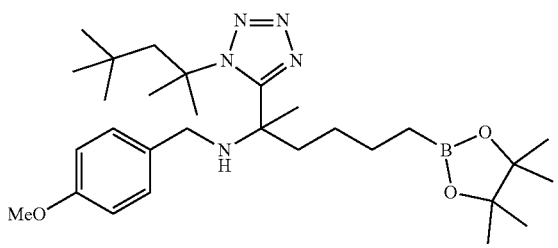 [SMILES: COc1ccc(CNC(C)(CCCCB2OC(C)(C)C(C)(C)O2)c2nnnn2C(C)(C)CC(C)(C)C)cc1]

To a solution of the chloro(1,5-cyclooctadiene)iridium(I) dimer (4.7 mg, 0.6 mmol) and ethylenebis(diphenylphosphine) (5.5 mg, 1.2 mmol) in 1.5 mL DCM was added N-(4-methoxybenzyl)-2-(1-(2,4,4-trimethylpentan-2-yl)-1H-tetrazol-5-yl)hex-5-en-2-amine (0.2 g, 0.5 mmol) and pinacolborane (0.07 mL, 0.55 mmol). The reaction mixture was stirred for 20 hours and then quenched using 0.2 mL MeOH, washed with water (2×5 mL), brine (5 mL), dried over MgSO4, filtered and concentrated under reduced pressure to obtain the crude product. The crude product was purified by flash chromatography yielding N-(4-methoxybenzyl)-6-(4,4,5,5-tetramethyl-1,3,2-dioxaborolan-2-yl)-2-(1-(2,4,4-trimethyl pen tan-2-yl)-1H-tetrazol-5-yl)hexan-2-amine (0.205 g) of as a white solid.

$^1$H NMR (500 MHz, Chloroform-d) δ7.24 (d, J=8.6 Hz, 2H), 6.86 (d, J=8.6 Hz, 2H), 3.79 (s, 3H), 3.65 (q, J=43.5, 11.7 Hz, 2H), 2.24-2.11 (m, 2H), 2.06 (d, J=14.9 Hz, 1H), 1.97 (s, 3H), 1.97 (s, 3H), 1.91 (d, J=15.0 Hz, 1H), 1.73 (s, 3H), 1.53-1.38 (m, 2H), 1.37-1.25 (m, 1H), 1.21 (d, J=2.3 Hz, 12H), 1.02-0.91 (m, 1H), 0.77 (t, J=7.8 Hz, 2H), 0.66 (s, 9H); LC-MS (EI) m/z: 550.5 (M+Na)$^+$.

Example 137a: N-phenethyl-2-(5-(5-(4,4,5,5-tetramethyl-1,3,2-dioxaborolan-2-yl)-1-(tritylamino)pentyl)-1H-tetrazol-1-yl)acetamide (Major Product)

Example 137b: N-((1-phenethyl-1H-tetrazol-5-yl)methyl)-6-(4,4,5,5-tetramethyl-1,3,2-dioxaborolan-2-yl)-2-(tritylamino)hexanamide (Minor Product)

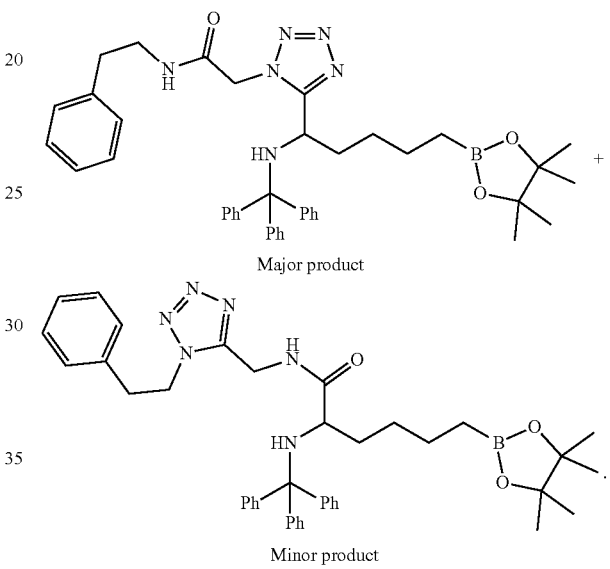

To a stirred solution of 5-(4,4,5,5-tetramethyl-1,3,2-dioxaborolan-2-yl) pentanal (0.2 g, 0.94 mmol) in methanol (2.0 mL) was added tritylamine (0.24 g, 0.94 mmol) and stirred for 0.5 h. Subsequently 2-isocyano-N-phenethylacetamide (0.176 g, 0.94 mmol) and azidotrimethylsilane (0.18 mL, 1.41 mmol) were added and further stirred for 16 h. The solvent was removed under reduced pressure and the residue was purified using flash chromatography to provide N-phenethyl-2-(5-(5-(4,4,5,5-tetramethyl-1,3,2-dioxaborolan-2-yl)-1-(tritylamino)pentyl)-1H-tetrazol-1-yl)acetamide (Major product, 0.450 g) and N-((1-phenethyl-1H-tetrazol-5-yl)methyl)-6-(4,4,5,5-tetramethyl-1,3,2-dioxaborolan-2-yl)-2-(tritylamino)hexanamide (Minor product, 0.030 g).

(Major desired product) $^1$H NMR (500 MHz, Chloroform-d) δ7.39-7.30 (m, 7H), 7.31-7.26 (m, 2H), 7.24-7.16 (m, 7H), 7.16-7.07 (m, 3H), 5.87 (t, J=5.8 Hz, 1H), 4.72 (d, J=16.6 Hz, 1H), 4.26 (d, J=16.6 Hz, 1H), 3.98 (td, J=8.0, 5.0 Hz, 1H), 3.50-3.34 (m, 2H), 2.92 (d, J=7.5 Hz, 1H), 2.72 (td, J=7.1, 2.7 Hz, 2H), 1.83 (dddd, J=13.5, 11.1, 8.4, 5.1 Hz, 1H), 1.74 (ddq, J=15.2, 12.4, 7.3, 6.2 Hz, 1H), 1.35-1.25 (m, 2H), 1.20 (s, 12H), 1.10-1.02 (m, 1H), 1.02-0.92 (m, 1H), 0.65 (td, J=7.6, 2.9 Hz, 2H); $^{13}$C NMR (126 MHz, Chloroform-d) δ 164.1, 158.4, 145.0, 138.1, 128.9, 128.9, 128.8, 128.8, 128.7, 128.6, 128.0, 126.9, 126.9, 126.8, 83.1, 71.6, 50.1, 48.7, 41.2, 41.1, 37.2, 35.4, 35.4, 27.5, 24.9, 23.8, 10.9; LC-MS (EI) m/z: 707.4 (M+Na)$^+$.

(Minor product) ¹H NMR (500 MHz, Chloroform-d) δ7.31-7.24 (m, 9H), 7.23-7.18 (m, 6H), 7.18-7.12 (m, 3H), 7.01-6.95 (m, 2H), 4.59 (td, J=6.9, 2.3 Hz, 2H), 3.71 (dd, J=15.7, 6.1 Hz, 1H), 3.57 (dd, J=15.8, 6.3 Hz, 1H), 3.24 (dd, J=6.7, 4.6 Hz, 1H), 3.13 (t, J=6.9 Hz, 2H), 1.69-1.53 (m, 1H), 1.37-1.24 (m, 4H), 1.20 (s, 12H), 1.15-1.01 (m, 1H), 0.66 (t, J=7.7 Hz, 2H); ¹³C NMR (126 MHz, Chloroform-d) δ175.4, 152.4, 145.3, 136.3, 128.9, 128.8, 128.8, 128.6, 128.5, 127.9, 127.9, 127.3, 126.8, 82.9, 71.6, 57.5, 48.7, 36.3, 34.8, 30.6, 27.5, 24.9, 24.8, 24.0, 10.9; LC-MS (EI) m/z: 707.4 (M+Na)⁺.

Example 138: 6-(4,4,5,5-tetramethyl-1,3,2-dioxaborolan-2-yl)-1-(1-(2,4,4-trimethylpentan-2-yl)-1H-tetrazol-5-yl)-N-tritylhexan-1-amine

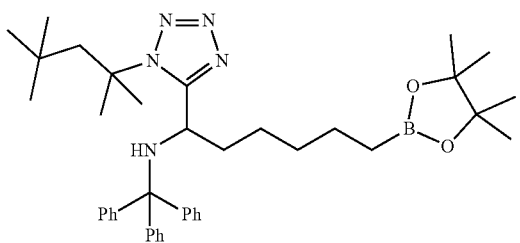 [SMILES: CC(C)(C)CC(C)(C)n1nnnc1C(CCCCCB1OC(C)(C)C(C)(C)O1)NC(c1ccccc1)(c1ccccc1)c1ccccc1]

The compound of example 138 was obtained by similar method described in example 129 starting from 6-(4,4,5,5-tetramethyl-1,3,2-dioxaborolan-2-yl)hexanal (1.0 mmol), tritylamine (1.0 mmol), tert-octyl isocyanide (1.0 mmol) and azidotrimethylsilane (1.0 mmol) in methanol.

¹H NMR (500 MHz, Chloroform-d) δ7.47-7.39 (m, 6H), 7.24-7.17 (m, 6H), 7.18-7.11 (m, 3H), 4.28 (dt, J=9.7, 5.1 Hz, 1H), 3.28 (d, J=8.9 Hz, 1H), 1.75-1.66 (m, 2H), 1.59 (s, 2H), 1.50 (s, 3H), 1.40 (s, 3H), 1.36-1.25 (m, 3H), 1.23 (s, 12H), 1.20-1.03 (m, 3H), 0.79 (s, 9H), 0.70 (t, J=7.8 Hz, 2H); LC-MS (EI) m/z: 672.3 (M+Na)⁺.

Example 139: N-benzyl-3-(5-(5-(4,4,5,5-tetramethyl-1,3,2-dioxaborolan-2-yl)-1-(tritylamino)pentyl)-1H-tetrazol-1-yl)propanamide

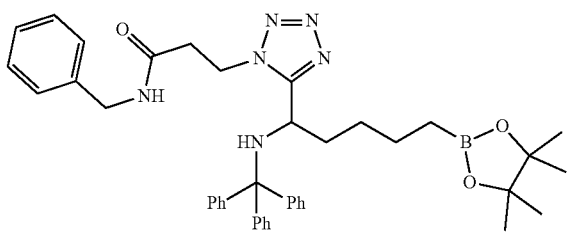 [SMILES: CC1(C)OB(CCCCC(NC(c2ccccc2)(c2ccccc2)c2ccccc2)c2nnnn2CCC(=O)NCc2ccccc2)OC1(C)C]

The compound of example 139 was obtained by similar method described in example 129 starting from 5-(4,4,5,5-tetramethyl-1,3,2-dioxaborolan-2-yl)pentanal (1.0 mmol), tritylamine (1.0 mmol), 3-isocyano-N-phenethylpropanamide (1.0 mmol) and azidotrimethylsilane (1.0 mmol) in methanol.

¹H NMR (500 MHz, Chloroform-d) δ7.41-7.35 (m, 6H), 7.35-7.30 (m, 2H), 7.24-7.15 (m, 8H), 7.15-7.09 (m, 3H), 5.93 (t, J=5.8 Hz, 1H), 4.46-4.31 (m, 2H), 4.16-3.89 (m, 3H), 2.97 (d, J=8.3 Hz, 1H), 2.64 (td, J=7.4, 1.8 Hz, 2H), 1.96-1.84 (m, 1H), 1.80-1.69 (m, 1H), 1.39-1.27 (m, 2H), 1.18 (s, 12H), 1.15-0.99 (m, 2H), 0.75-0.60 (m, 2H); LC-MS (EI) m/z: 683.3 (M–H)⁺.

Example 140: 1-(1-((1-(4-chlorobenzyl)piperidin-4-yl)methyl)-1H-tetrazol-5-yl)-5-(4,4,5,5-tetramethyl-1,3,2-dioxaborolan-2-yl)-N-tritylpentan-1-amin

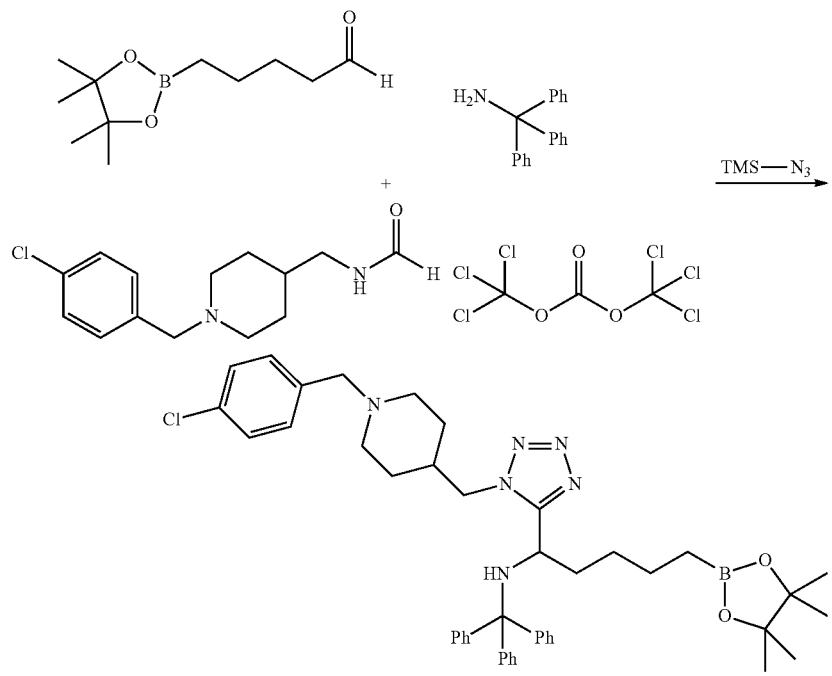

To a stirred solution of N-((1-(4-chlorobenzyl)piperidin-4-yl)methyl)formamide (0.188 g, 0.70 mmol) in DCM (1.0 mL), trimethylamine (0.24 mL, 2.4 mmol) was added and cooled to −5° C. After 10 minutes, triphosgene (0.084 g, 0.28 mmol) in DCM (0.5 mL) was added slowly. The reaction mixture was stirred for 10 minutes until the formamide was completely consumed (monitored by TLC). Afterwards, preformed Schiff's base [ prepared by mixing 5-(4,4,5,5-tetramethyl-1,3,2-dioxaborolan-2-yl) pentanal (0.1 g, 0.471 mmol) and tritylamine (0.12 g, 0.471 mmol) in methanol (1.0 mL) and stirred for 30 minutes] and azidotrimethylsilane (0.1 mL, 0.471 mmol) were added and further stirred at room temperature for 16 h. The solvent was removed under reduced pressure and the residue was purified using flash chromatography to provide 1-(1-((1-(4-chlorobenzyl)piperidin-4-yl)methyl)-1H-tetrazol-5-yl)-5-(4,4,5,5-tetramethyl-1,3,2-dioxaborolan-2-yl)-N-tritylpentan-1-amin (0.225 g).

$^1$H NMR (500 MHz, Chloroform-d) δ7.42-7.35 (m, 6H), 7.30-7.24 (m, 2H), 7.24-7.16 (m, 8H), 7.16-7.09 (m, 3H), 3.88 (td, J=7.6, 4.7 Hz, 1H), 3.61 (dd, J=13.9, 7.1 Hz, 1H), 3.48-3.35 (m, 3H), 2.91 (d, J=8.4 Hz, 1H), 2.85-2.72 (m, 2H), 1.92-1.80 (m, 3H), 1.81-1.71 (m, 1H), 1.66-1.53 (m, 2H), 1.45 (ddq, J=37.0, 13.6, 3.9, 3.4 Hz, 2H), 1.37-1.26 (m, 2H), 1.20 (s, 12H), 1.17-1.08 (m, 1H), 0.68 (t, J=7.8 Hz, 2H); $^{13}$C NMR (126 MHz, Chloroform-d) δ157.7, 145.4, 137.0, 132.8, 130.4, 128.6, 128.4, 127.9, 126.8, 83.0, 71.6, 62.4, 52.9, 52.9, 52.5, 48.1, 37.4, 35.8, 30.0, 30.0, 29.5, 27.5, 24.9, 24.9, 24.9, 24.1, 11.0; LC-MS (EI) m/z: 767.4 (M+Na)$^+$.

Example 141 to 230 were prepared in analogues manner of example 129-140 from the appropriate intermediate that are commercially available or synthesized as above.

| Ex. No. | LC-MS (EI)m/z: | IUPAC Name |
|---|---|---|
| 141 | 636.6 (M + Na)$^+$ | 1-(1-benzyl-1H-tetrazol-5-yl)-5-(4,4,5,5-tetramethyl-1,3,2-dioxaborolan-2-yl)-N-tritylpentan-1-amine. |
| 142 | 654.6 (M + Na)$^+$ | 1-(1-(3-fluorobenzyl)-1H-tetrazol-5-yl)-5-(4,4,5,5-tetramethyl-1,3,2-dioxaborolan-2-yl)-N-tritylpentan-1-amine. |
| 143 | 650.6 (M + Na)$^+$ | 1-(1-phenethyl-1H-tetrazol-5-yl)-5-(4,4,5,5-tetramethyl-1,3,2-dioxaborolan-2-yl)-N-tritylpentan-1-amine. |
| 144 | 627.4 (M + Na) | 1-(1-cyclohexyl-1H-tetrazol-5-yl)-5-(4,4,5,5-tetramethyl-1,3,2-dioxaborolan-2-yl)-N-tritylpentan-1-amine |
| 145 | 602.3 (M + Na)$^+$ | 1-(1-(tert-butyl)-1H-tetrazol-5-yl)-5-(4,4,5,5-tetramethyl-1,3,2-dioxaborolan-2-yl)-N-tritylpentan-1-amine. |
| 146 | 693.4 (M + Na)$^+$ | N-benzyl-2-(5-(5-(4,4,5,5-tetramethyl-1,3,2-dioxaborolan-2-yl)-1-(tritylamino)pentyl)-1H-tetrazol-1-yl)acetamide. |
| 147 | 513.2 (M + Na)$^+$ | 4-(1-(1-(2-fluoro-5-nitrophenyl)-1H-tetrazol-5-yl)-5-(4,4,5,5-tetramethyl-1,3,2-dioxaborolan-2-yl)pentyl)morpholine. |
| 148 | 752.5 (M + Na)$^+$ | 1-(1-(2-morpholino-5-nitrophenyl)-1H-tetrazol-5-yl)-5-(4,4,5,5-tetramethyl-1,3,2-dioxaborolan-2-yl)-N-tritylpentan-1-amine. |
| 149 | 711.4 (M + Na)$^+$ | N-(4-fluorobenzyl)-2-(5-(5-(4,4,5,5-tetramethyl-1,3,2-dioxaborolan-2-yl)-1-(tritylamino)pentyl)-1H-tetrazol-1-yl)acetamide. |
| 150 | 707.5 (M + Na)$^+$ | N-((S)-1-phenylethyl)-2-(5-(5-(4,4,5,5-tetramethyl-1,3,2-dioxaborolan-2-yl)-1-(tritylamino)pentyl)-1H-tetrazol-1-yl)acetamide. |
| 151 | 699.4 (M + Na)$^+$ | 2-(5-(5-(4,4,5,5-tetramethyl-1,3,2-dioxaborolan-2-yl)-1-(tritylamino)pentyl)-1H-tetrazol-1-yl)-N-(thiophen-2-ylmethyl)acetamide. |
| 152 | 776.5 (M + Na)$^+$ | N-(1-benzylpiperidin-4-yl)-2-(5-(5-(4,4,5,5-tetramethyl-1,3,2-dioxaborolan-2-yl)-1-(tritylamino)pentyl)-1H-tetrazol-1-yl)acetamide. |
| 153 | 643.4 (M + Na)$^+$; 619.3 (M − H)$^+$ | N-cyclopropyl-2-(5-(5-(4,4,5,5-tetramethyl-1,3,2-dioxaborolan-2-yl)-1-(tritylamino)pentyl)-1H-tetrazol-1-yl)acetamide. |
| 154 | 643.4 (M + Na)$^+$ | N-(2-morpholinoethyl)-2-(5-(5-(4,4,5,5-tetramethyl-1,3,2-dioxaborolan-2-yl)-1-(tritylamino)pentyl)-1H-tetrazol-1-yl)acetamide. |
| 155 | 767.5 (M + Na)$^+$ | N-(3,4-dimethoxyphenethyl)-2-(5-(5-(4,4,5,5-tetramethyl-1,3,2-dioxaborolan-2-yl)-1-(tritylamino)pentyl)-1H-tetrazol-1-yl)acetamide. |
| 156 | 659.4 (M + Na)$^+$ | N-butyl-2-(5-(5-(4,4,5,5-tetramethyl-1,3,2-dioxaborolan-2-yl)-1-(tritylamino)pentyl)-1H-tetrazol-1-yl)acetamide. |
| 157 | 641.3 (M + Na)$^+$ | N-(prop-2-yn-1-yl)-2-(5-(5-(4,4,5,5-tetramethyl-1,3,2-dioxaborolan-2-yl)-1-(tritylamino)pentyl)-1H-tetrazol-1-yl)acetamide. |
| 158 | 762.4 (M + Na)$^+$ | 1-(4-benzylpiperazin-1-yl)-2-(5-(5-(4,4,5,5-tetramethyl-1,3,2-dioxaborolan-2-yl)-1-(tritylamino)pentyl)-1H-tetrazol-1-yl)ethanone. |
| 159 | 673.4 (M + Na)$^+$ | 1-morpholino-2-(5-(5-(4,4,5,5-tetramethyl-1,3,2-dioxaborolan-2-yl)-1-(tritylamino)pentyl)-1H-tetrazol-1-yl)ethanone. |
| 160 | 657.4 (M + Na)$^+$ | 1-(pyrrolidin-1-yl)-2-(5-(5-(4,4,5,5-tetramethyl-1,3,2-dioxaborolan-2-yl)-1-(tritylamino)pentyl)-1H-tetrazol-1-yl)ethanone. |
| 161 | 727.5 (M + Na)$^+$ | N-(3-chlorobenzyl)-2-(5-(5-(4,4,5,5-tetramethyl-1,3,2-dioxaborolan-2-yl)-1-(tritylamino)pentyl)-1H-tetrazol-1-yl)acetamide. |
| 162 | 727.5 (M + Na)$^+$ | N-(2-chlorobenzyl)-2-(5-(5-(4,4,5,5-tetramethyl-1,3,2-dioxaborolan-2-yl)-1-(tritylamino)pentyl)-1H-tetrazol-1-yl)acetamide. |
|  | 694.4 (M + Na)$^+$ | N-(pyridin-3-ylmethyl)-2-(5-(5-(4,4,5,5-tetramethyl-1,3,2-dioxaborolan-2-yl)-1-(tritylamino)pentyl)-1H-tetrazol-1-yl)acetamide. |
| 163 | 723.4 (M + Na)$^+$ | N-(4-methoxybenzyl)-2-(5-(5-(4,4,5,5-tetramethyl-1,3,2-dioxaborolan-2-yl)-1-(tritylamino)pentyl)-1H-tetrazol-1-yl)acetamide. |
| 164 | 741.4 (M + Na)$^+$ | N-(4-chlorobenzyl)-3-(5-(5-(4,4,5,5-tetramethyl-1,3,2-dioxaborolan-2-yl)-1-(tritylamino)pentyl)-1H-tetrazol-1-yl)propanamide. |
| 165 | 721.4 (M + Na)$^+$ | N-phenethyl-3-(5-(5-(4,4,5,5-tetramethyl-1,3,2-dioxaborolan-2-yl)-1-(tritylamino)pentyl)-1H-tetrazol-1-yl)propanamide |
| 166 | 646.5 (M + Na)$^+$ | methyl 4-(5-(5-(4,4,5,5-tetramethyl-1,3,2-dioxaborolan-2-yl)-1-(tritylamino)pentyl)-1H-tetrazol-1-yl)butanoate. |
| 167 | 689.4 (M + Na)$^+$ | 1-(1-(2-(1H-indol-3-yl)ethyl)-1H-tetrazol-5-yl)-5-(4,4,5,5-tetramethyl-1,3,2-dioxaborolan-2-yl)-N-tritylpentan-1-amine. |
| 168 | 737.4 (M + Na)$^+$ | N-benzyl-N-(2-hydroxyethyl)-2-(5-(5-(4,4,5,5-tetramethyl-1,3,2-dioxaborolan-2-yl)-1-(tritylamino)pentyl)-1H-tetrazol-1-yl)acetamide. |
| 169 | 707.4 (M + Na)$^+$ | N-benzyl-N-methyl-2-(5-(5-(4,4,5,5-tetramethyl-1,3,2-dioxaborolan-2-yl)-1-(tritylamino)pentyl)-1H-tetrazol-1-yl)acetamide. |
| 170 | 741.5 (M + Na)$^+$ | N-((S)-1-(4-chlorophenyl)ethyl)-2-(5-(5-(4,4,5,5-tetramethyl-1,3,2-dioxaborolan-2-yl)-1-(tritylamino)pentyl)-1H-tetrazol-1-yl)acetamide. |
| 171 | 650.4 (M + Na)$^+$ | 1-(1-(1-phenylethyl)-1H-tetrazol-5-yl)-5-(4,4,5,5-tetramethyl-1,3,2-dioxaborolan-2-yl)-N-tritylpentan-1-amine. |
| 172 | 650.4 (M + Na)$^+$ | 1-(1-((R)-1-phenylethyl)-1H-tetrazol-5-yl)-5-(4,4,5,5-tetramethyl-1,3,2-dioxaborolan-2-yl)-N-tritylpentan-1-amine. |
| 173 | 650.4 (M + Na)$^+$ | 1-(1-((S)-1-phenylethyl)-1H-tetrazol-5-yl)-5-(4,4,5,5-tetramethyl-1,3,2-dioxaborolan-2-yl)-N-tritylpentan-1-amine. |
| 174 | 684.4 (M + Na)$^+$ | 1-(1-((R)-1-(4-chlorophenyl)ethyl)-1H-tetrazol-5-yl)-5-(4,4,5,5-tetramethyl-1,3,2-dioxaborolan-2-yl)-N-tritylpentan-1-amine. |
| 175 | 684.4 (M + Na)$^+$ | 1-(1-((R)-1-(4-methoxyphenyl)ethyl)-1H-tetrazol-5-yl)-5-(4,4,5,5-tetramethyl-1,3,2-dioxaborolan-2-yl)-N-tritylpentan-1-amine. |

-continued

| Ex. No. | LC-MS (EI)m/z: | IUPAC Name |
|---|---|---|
| 176 | 654.4 (M + Na)+ | 1-(1-(4-fluorobenzyl)-1H-tetrazol-5-yl)-5-(4,4,5,5-tetramethyl-1,3,2-dioxaborolan-2-yl)-N-tritylpentan-1-amine. |
| 177 | 654.4 (M + Na)+ | 1-(1-(2-fluorobenzyl)-1H-tetrazol-5-yl)-5-(4,4,5,5-tetramethyl-1,3,2-dioxaborolan-2-yl)-N-tritylpentan-1-amine. |
| 178 | 670.3 (M + Na)+ | 1-(1-(3-chlorobenzyl)-1H-tetrazol-5-yl)-5-(4,4,5,5-tetramethyl-1,3,2-dioxaborolan-2-yl)-N-tritylpentan-1-amine. |
| 179 | 670.3 (M + Na)+ | 1-(1-(2-chlorobenzyl)-1H-tetrazol-5-yl)-5-(4,4,5,5-tetramethyl-1,3,2-dioxaborolan-2-yl)-N-tritylpentan-1-amine. |
| 180 | 714.3 [M(Br79) + Na]+; 716.3 [M(Br81) + Na]+ | 1-(1-(4-bromobenzyl)-1H-tetrazol-5-yl)-5-(4,4,5,5-tetramethyl-1,3,2-dioxaborolan-2-yl)-N-tritylpentan-1-amine. |
| 181 | 661.4 (M + Na)+ | 4-((5-(5-(4,4,5,5-tetramethyl-1,3,2-dioxaborolan-2-yl)-1-(tritylamino)pentyl)-1H-tetrazol-1-yl)methyl)benzonitrile |
| 182 | 704.4 (M + Na)+ | 1-(1-(2,4-dichlorobenzyl)-1H-tetrazol-5-yl)-5-(4,4,5,5-tetramethyl-1,3,2-dioxaborolan-2-yl)-N-tritylpentan-1-amine. |
| 183 | 704.4 (M + Na)+ | 1-(1-(3,4-dichlorobenzyl)-1H-tetrazol-5-yl)-5-(4,4,5,5-tetramethyl-1,3,2-dioxaborolan-2-yl)-N-tritylpentan-1-amine. |
| 184 | 732.3 [M(Br79) + Na]+; 734.3 [M(Br81) + Na]+ | 1-(1-(4-bromo-2-fluorobenzyl)-1H-tetrazol-5-yl)-5-(4,4,5,5-tetramethyl-1,3,2-dioxaborolan-2-yl)-N-tritylpentan-1-amine |
| 185 | 666.4 (M + Na)+ | 1-(1-(2-methoxybenzyl)-1H-tetrazol-5-yl)-5-(4,4,5,5-tetramethyl-1,3,2-dioxaborolan-2-yl)-N-tritylpentan-1-amine. |
| 186 | 656.4 (M − H)+ | 3-phenyl-3-(5-(5-(4,4,5,5-tetramethyl-1,3,2-dioxaborolan-2-yl)-1-(tritylamino)pentyl)-1H-tetrazol-1-yl)propan-1-ol. |
| 187 | 637.4 (M + Na)+ | 1-(1-(pyridin-3-ylmethyl)-1H-tetrazol-5-yl)-5-(4,4,5,5-tetramethyl-1,3,2-dioxaborolan-2-yl)-N-tritylpentan-1-amine. |
| 188 | 642.3 (M + Na)+ | 5-(4,4,5,5-tetramethyl-1,3,2-dioxaborolan-2-yl)-1-(1-(thiophen-2-ylmethyl)-1H-tetrazol-5-yl)-N-tritylpentan-1-amine. |
| 190 | 668.4 (M + Na)+ | 1-(1-(4-fluorophenethyl)-1H-tetrazol-5-yl)-5-(4,4,5,5-tetramethyl-1,3,2-dioxaborolan-2-yl)-N-tritylpentan-1-amine. |
| 191 | 710.4 (M + Na)+ | 1-(1-(3,4-dimethoxyphenethyl)-1H-tetrazol-5-yl)-5-(4,4,5,5-tetramethyl-1,3,2-dioxaborolan-2-yl)-N-tritylpentan-1-amine. |
| 192 | 680.4 (M + Na)+ | 1-(1-(2-methoxyphenethyl)-1H-tetrazol-5-yl)-5-(4,4,5,5-tetramethyl-1,3,2-dioxaborolan-2-yl)-N-tritylpentan-1-amine. |
| 193 | 642.3 (M − H)+ | 4-(2-(5-(5-(4,4,5,5-tetramethyl-1,3,2-dioxaborolan-2-yl)-1-(tritylamino)pentyl)-1H-tetrazol-1-yl)ethyl)phenol. |
| 194 | 680.4 (M + Na)+ | 1-(1-(3-methoxyphenethyl)-1H-tetrazol-5-yl)-5-(4,4,5,5-tetramethyl-1,3,2-dioxaborolan-2-yl)-N-tritylpentan-1-amine. |
| 195 | 664.5 (M + Na)+ | 1-(1-(3-phenylpropyl)-1H-tetrazol-5-yl)-5-(4,4,5,5-tetramethyl-1,3,2-dioxaborolan-2-yl)-N-tritylpentan-1-amine. |
| 196 | 728.3 [M(Br79) + Na]+; 730.3 [M(Br81) + Na]+. | 1-(1-(4-bromophenethyl)-1H-tetrazol-5-yl)-5-(4,4,5,5-tetramethyl-1,3,2-dioxaborolan-2-yl)-N-tritylpentan-1-amine. |
| 197 | 672.4 (M + Na)+ | 1-(1-(2,5-difluorobenzyl)-1H-tetrazol-5-yl)-5-(4,4,5,5-tetramethyl-1,3,2-dioxaborolan-2-yl)-N-tritylpentan-1-amine. |
| 198 | 705.3 (M − H)+ | N-(2,4-difluorobenzyl)-2-(5-(5-(4,4,5,5-tetramethyl-1,3,2-dioxaborolan-2-yl)-1-(tritylamino)pentyl)-1H-tetrazol-1-yl)acetamide. |
| 199 | 683.5 (M − H)+ | N-(4-methylbenzyl)-2-(5-(5-(4,4,5,5-tetramethyl-1,3,2-dioxaborolan-2-yl)-1-(tritylamino)pentyl)-1H-tetrazol-1-yl)acetamide. |
| 200 | 741.5 (M + Na)+ | N-(4-chlorophenethyl)-2-(5-(5-(4,4,5,5-tetramethyl-1,3,2-dioxaborolan-2-yl)-1-(tritylamino)pentyl)-1H-tetrazol-1-yl)acetamide. |
| 201 | 721.3 (M − H)+ | N-(4-chloro-2-fluorobenzyl)-2-(5-(5-(4,4,5,5-tetramethyl-1,3,2-dioxaborolan-2-yl)-1-(tritylamino)pentyl)-1H-tetrazol-1-yl)acetamide. |
| 202 | 705.5 (M − H)+ | N-(2,6-difluorobenzyl)-2-(5-(5-(4,4,5,5-tetramethyl-1,3,2-dioxaborolan-2-yl)-1-(tritylamino)pentyl)-1H-tetrazol-1-yl)acetamide. |
| 203 | 694.4 (M − H)+ | N-(4-cyanobenzyl)-2-(5-(5-(4,4,5,5-tetramethyl-1,3,2-dioxaborolan-2-yl)-1-(tritylamino)pentyl)-1H-tetrazol-1-yl)acetamide. |
| 204 | 745.4 (M + Na)+ | N-(4-chlorobenzyl)-3-methyl-2-(5-(5-(4,4,5,5-tetramethyl-1,3,2-dioxaborolan-2-yl)-1-(tritylamino)pentyl)-1H-tetrazol-1-yl)butanamide |
| 205 | 747.4 (M(Br79) − H)+; 749.4 [M(Br81) − H]+ | N-(4-bromobenzyl)-2-(5-(5-(4,4,5,5-tetramethyl-1,3,2-dioxaborolan-2-yl)-1-(tritylamino)pentyl)-1H-tetrazol-1-yl)acetamide. |
| 206 | 672.3 (M + Na)+ | 6-(4,4,5,5-tetramethyl-1,3,2-dioxaborolan-2-yl)-1-(1-(2,4,4-trimethylpentan-2-yl)-1H-tetrazol-5-yl)-N-tritylhexan-1-amine. |
| 207 | 707.4 (M + Na)+ | N-benzyl-2-(5-(6-(4,4,5,5-tetramethyl-1,3,2-dioxaborolan-2-yl)-1-(tritylamino)hexyl)-1H-tetrazol-1-yl)acetamide. |
| 208 | 741.3 (M + Na)+ | N-(4-chlorobenzyl)-2-(5-(6-(4,4,5,5-tetramethyl-1,3,2-dioxaborolan-2-yl)-1-(tritylamino)hexyl)-1H-tetrazol-1-yl)acetamide. |
| 209 | 655.4 (M + Na)+ | N-(prop-2-yn-1-yl)-2-(5-(6-(4,4,5,5-tetramethyl-1,3,2-dioxaborolan-2-yl)-1-(tritylamino)hexyl)-1H-tetrazol-1-yl)acetamide. |
| 210 | 721.5 (M + Na)+ | N-phenethyl-2-(5-(6-(4,4,5,5-tetramethyl-1,3,2-dioxaborolan-2-yl)-1-(tritylamino)hexyl)-1H-tetrazol-1-yl)acetamide. |
| 211 | 783.2 (M + Na)+ | N-((perfluorophenyl)methyl)-2-(5-(5-(4,4,5,5-tetramethyl-1,3,2-dioxaborolan-2-yl)-1-(tritylamino)pentyl)-1H-tetrazol-1-yl)acetamide. |
| 212 | 765.2 (M + Na)+ | N-(2,3,4,5-tetrafluorobenzyl)-2-(5-(5-(4,4,5,5-tetramethyl-1,3,2-dioxaborolan-2-yl)-1-(tritylamino)pentyl)-1H-tetrazol-1-yl)acetamide. |
| 213 | 747.2 (M + Na)+ | 2-(5-(5-(4,4,5,5-tetramethyl-1,3,2-dioxaborolan-2-yl)-1-(tritylamino)pentyl)-1H-tetrazol-1-yl)-N-(2,4,6-trifluorobenzyl)acetamide. |
| 214 | 728.2 (M + Na)+ | N-((6-chloropyridin-3-yl)methyl)-2-(5-(5-(4,4,5,5-tetramethyl-1,3,2-dioxaborolan-2-yl)-1-(tritylamino)pentyl)-1H-tetrazol-1-yl)acetamide. |
| 215 | 729.2 (M + Na)+ | N-(2,3-difluorobenzyl)-2-(5-(5-(4,4,5,5-tetramethyl-1,3,2-dioxaborolan-2-yl)-1-(tritylamino)pentyl)-1H-tetrazol-1-yl)acetamide. |
| 216 | 729.2 (M + Na)+ | N-(2,5-difluorobenzyl)-2-(5-(5-(4,4,5,5-tetramethyl-1,3,2-dioxaborolan-2-yl)-1-(tritylamino)pentyl)-1H-tetrazol-1-yl)acetamide. |
| 217 | 729.2 (M + Na)+ | N-(3,5-difluorobenzyl)-2-(5-(5-(4,4,5,5-tetramethyl-1,3,2-dioxaborolan-2-yl)-1-(tritylamino)pentyl)-1H-tetrazol-1-yl)acetamide. |
| 218 | 747.2 (M + Na)+ | 2-(5-(5-(4,4,5,5-tetramethyl-1,3,2-dioxaborolan-2-yl)-1-(tritylamino)pentyl)-1H-tetrazol-1-yl)-N-(2,3,4-trifluorobenzyl)acetamide |
| 219 | 747.2 (M + Na)+ | 2-(5-(5-(4,4,5,5-tetramethyl-1,3,2-dioxaborolan-2-yl)-1-(tritylamino)pentyl)-1H-tetrazol-1-yl)-N-(2,3,5-trifluorobenzyl)acetamide. |
| 220 | 747.2 (M + Na)+ | 2-(5-(5-(4,4,5,5-tetramethyl-1,3,2-dioxaborolan-2-yl)-1-(tritylamino)pentyl)-1H-tetrazol-1-yl)-N-(3,4,5-trifluorobenzyl)acetamide. |
| 221 | 747.2 (M + Na)+ | 2-(5-(5-(4,4,5,5-tetramethyl-1,3,2-dioxaborolan-2-yl)-1-(tritylamino)pentyl)-1H-tetrazol-1-yl)-N-(2,3,6-trifluorobenzyl)acetamide. |
| 222 | 765.2 (M + Na)+ | N-(2,3,5,6-tetrafluorobenzyl)-2-(5-(5-(4,4,5,5-tetramethyl-1,3,2-dioxaborolan-2-yl)-1-(tritylamino)pentyl)-1H-tetrazol-1-yl)acetamide. |

| Ex. No. | LC-MS (EI)m/z: | IUPAC Name |
|---|---|---|
| 223 | 729.2 (M + Na)+ | N-(3,4-difluorobenzyl)-2-(5-(5-(4,4,5,5-tetramethyl-1,3,2-dioxaborolan-2-yl)-1-(tritylamino)pentyl)-1H-tetrazol-1-yl)acetamide. |
| 224 | 747.2 (M + Na)+ | 2-(5-(5-(4,4,5,5-tetramethyl-1,3,2-dioxaborolan-2-yl)-1-(tritylamino)pentyl)-1H-tetrazol-1-yl)-N-(2,4,5-trifluorobenzyl)acetamide. |
| 225 | 767.4 (M + Na)+ | 1-(1-((1-(4-chlorobenzyl)piperidin-4-yl)methyl)-1H-tetrazol-5-yl)-5-(4,4,5,5-tetramethyl-1,3,2-dioxaborolan-2-yl)-N-tritylpentan-1-amine. |
| 226 | 707.3 (M + Na)+ | N-((R)-1-phenylethyl)-2-(5-(5-(4,4,5,5-tetramethyl-1,3,2-dioxaborolan-2-yl)-1-(tritylamino)pentyl)-1H-tetrazol-1-yl)acetamide. |
| 227 | 728.1 (M + Na)+ | 4-chloro-N-(2-(5-(5-(4,4,5,5-tetramethyl-1,3,2-dioxaborolan-2-yl)-1-(tritylamino)pentyl)-1H-tetrazol-1-yl)ethyl)benzamide. |
| 228 | 554.3 (M + H)+ | N-(4-chlorobenzyl)-2-(5-(1-((pyridin-4-ylmethyl)amino)-5-(4,4,5,5-tetramethyl-1,3,2-dioxaborolan-2-yl)pentyl)-1H-tetrazol-1-yl)acetamide. |
| 229 | 560.4 (M + H)+ | tert-butyl ((1-(1-(1-(2-((4-chlorobenzyl)amino)-2-oxoethyl)-1H-tetrazol-5-yl)-5-(4,4,5,5-tetramethyl-1,3,2-dioxaborolan-2-yl)pentyl)piperidin-4-yl)methyl)carbamate. |
| 230 | 560.3 (M + H)+ | N-(4-chlorobenzyl)-2-(5-(1-((1-methylpiperidin-4-yl)amino)-5-(4,4,5,5-tetramethyl-1,3,2-dioxaborolan-2-yl)pentyl)-1H-tetrazol-1-yl)acetamide. |

Example 231: N-(2-fluorobenzyl)-2-(5-(5-(4,4,5,5-tetramethyl-1,3,2-dioxaborolan-2-yl)-1-(tritylamino)pentyl)-1H-tetrazol-1-yl)acetamide

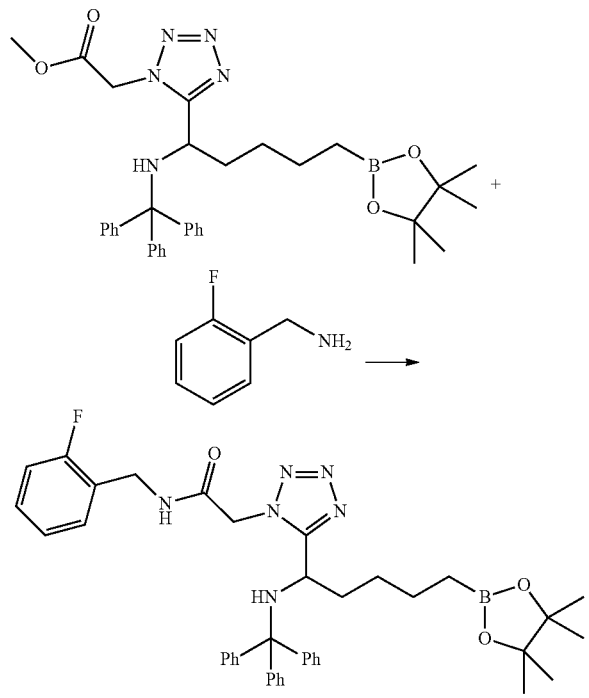

Under the $N_2$ atmosphere methyl 2-(5-(5-(4,4,5,5-tetramethyl-1,3,2-dioxaborolan-2-yl)-1-(tritylamino)pentyl)-1H-tetrazol-1-yl)acetate (0.5 g, 0.839 mmol, obtained in example 131) and (2-fluorophenyl) methanamine (0.48 mL, 4.19 mmol) mixed together and stirred at room temperature for 16 h. Excess amine was removed by washing with petroleum ether and decantation procedure (3×20 mL). The crude residue was purified using flash chromatography to provide N-(2-fluorobenzyl)-2-(5-(5-(4,4,5,5-tetramethyl-1,3,2-dioxaborolan-2-yl)-1-(tritylamino)pentyl)-1H-tetrazol-1-yl)acetamide (0.4 g).

$^1$H NMR (500 MHz, Chloroform-d) δ7.36-7.30 (m, 6H), 7.25-7.21 (m, 1H), 7.21-7.15 (m, 7H), 7.15-7.10 (m, 3H), 7.08 (td, J=7.5, 1.2 Hz, 1H), 7.02 (ddd, J=9.5, 8.1, 1.2 Hz, 1H), 6.26 (t, J=5.9 Hz, 1H), 4.80 (d, J=16.7 Hz, 1H), 4.53-4.30 (m, 3H), 4.01 (q, J=7.6 Hz, 1H), 2.93 (d, J=7.4 Hz, 1H), 1.91-1.80 (m, 1H), 1.80-1.69 (m, 1H), 1.31-1.23 (m, 2H), 1.20 (s, 12H), 1.15-0.94 (m, 2H), 0.64 (td, J=7.6, 2.3 Hz, 2H); LC-MS (EI) m/z: 711.4 (M+Na)+.

Example 232 to 233 were prepared in analogues manner of example 231 from the appropriate intermediate that are commercially or synthesized as above.

| Ex. No. | LC-MS (EI)m/z: | IUPAC Name |
|---|---|---|
| 232 | 727.5 (M + Na)+ | N-(4-chlorobenzyl)-2-(5-(5-(4,4,5,5-tetramethyl-1,3,2-dioxaborolan-2-yl)-1-(tritylamino)pentyl)-1H-tetrazol-1-yl)acetamide. |
| 233 | 707.4 (M + Na)+ | N-phenethyl-2-(5-(5-(4,4,5,5-tetramethyl-1,3,2-dioxaborolan-2-yl)-1-(tritylamino)pentyl)-1H-tetrazol-1-yl)acetamide. |

Example 234: 2-(5-(5-(4,4,5,5-tetramethyl-1,3,2-dioxaborolan-2-yl)-1-(tritylamino) pentyl)-1H-tetrazol-1-yl)acetic acid

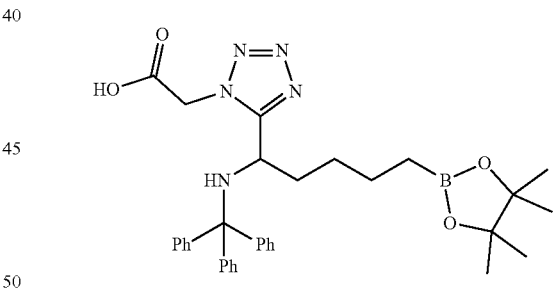

To a stirred solution of methyl 2-(5-(5-(4,4,5,5-tetramethyl-1,3,2-dioxaborolan-2-yl)-1-(tritylamino)pentyl)-1H-tetrazol-1-yl)acetate (3.5 g, 5.87 mmol, obtained in example 131) in THF (12.0 mL) was added LiOH (0.423 g, 17.63 mmol) dissolved in $H_2O$ (6.0 mL) and MeOH (1.0 mL) and the reaction mixture was stirred for 16 h. The solvent was removed under reduced pressure and the residue was re-dissolved in $H_2O$ (10 mL), cooled to 0° C. and acidified with 1N aqueous HCl to pH~4-5 and extracted with ethyl acetate (3×100 mL). Combined organic layer was washed with brine (100 mL), dried over anhydrous $MgSO_4$, filtered and concentrated under reduced pressure to obtain 2-(5-(5-(4,4,5,5-tetramethyl-1,3,2-dioxaborolan-2-yl)-1-(tritylamino)pentyl)-1H-tetrazol-1-yl)acetic acid as a white solid (2.45 g) LC-MS (EI) m/z: 604.3 (M+Na)+.

Example 235: N-(4-chlorophenyl)-2-(5-(5-(4,4,5,5-tetramethyl-1,3,2-dioxaborolan-2-yl)-1-(tritylamino)pentyl)-1H-tetrazol-1-yl)acetamide

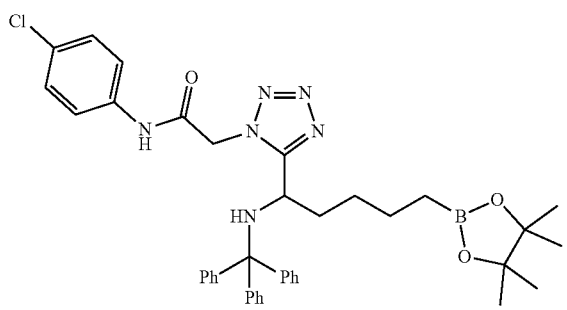 [SMILES: CC1(C)OB(CCCCC(NC(c2ccccc2)(c2ccccc2)c2ccccc2)c2nnnn2CC(=O)Nc2ccc(Cl)cc2)OC1(C)C]

To a stirred solution of 2-(5-(5-(4,4,5,5-tetramethyl-1,3,2-dioxaborolan-2-yl)-1-(tritylamino)pentyl)-1H-tetrazol-1-yl)acetic acid (0.15 g, 0.258 mmol) in DMF (2.0 mL) was added 4-chloroaniline (0.050 g, 0.38 mmol), HOBt·HCl (0.035 g, 0.258 mmol) and NMM (0.1 mL, 0.774 mmol). After 0.5 h of stirring, EDCI·HCl (0.098 g, 0.516 mmol) was added and the reaction mixture was further stirred at room temperature of 16 h. The reaction mixture was poured on ice-cold water, solid precipitated out, collected by filtration and vacuum dried to obtain title compound as a pale yellow solid (0.210 g).

$^1$H NMR (500 MHz, Chloroform-d) δ7.88 (s, 1H), 7.41-7.31 (m, 8H), 7.31-7.25 (m, 2H), 7.19 (t, J=7.7 Hz, 6H), 7.17-7.08 (m, 3H), 4.88 (d, J=16.6 Hz, 1H), 4.55 (d, J=16.6 Hz, 1H), 4.11-4.03 (m, 1H), 2.99 (d, J=7.2 Hz, 1H), 1.93-1.78 (m, 2H), 1.35-1.26 (m, 2H), 1.19 (s, 12H), 1.16-1.05 (m, 1H), 1.05-0.92 (m, 1H), 0.60 (td, J=7.8, 7.1, 2.3 Hz, 2H); $^{13}$C NMR (126 MHz, Chloroform-d) δ162.21, 158.75, 144.94, 135.41, 130.25, 129.18, 128.58, 128.05, 126.90, 121.52, 83.02, 71.65, 50.54, 48.91, 37.13, 27.67, 24.87, 23.84, 10.94; LC-MS (EI) m/z: 713.2 (M+Na)$^+$.

Example 236 and 237 were prepared in analogues manner of example 235 from the appropriate intermediate that are commercially or synthesized as above.

| Ex. No. | LC-MS (EI)m/z: | IUPAC Name |
|---|---|---|
| 236 | 760.3 (M + Na)$^+$ | N-((6-(1H-imidazol-1-yl)pyridin-3-yl)methyl)-2-(5-(5-(4,4,5,5-tetramethyl-1,3,2-dioxaborolan-2-yl)-1-(tritylamino)pentyl)-1H-tetrazol-1-yl)acetamide. |
| 237 | 769.3 (M + Na)$^+$ | N-([1,1'-biphenyl]-4-ylmethyl)-2-(5-(5-(4,4,5,5-tetramethyl-1,3,2-dioxaborolan-2-yl)-1-(tritylamino)pentyl)-1H-tetrazol-1-yl)acetamide. |

Example 238: N-((1-(4-chlorobenzyl)-1H-1,2,3-triazol-4-yl)methyl)-2-(5-(5-(4,4,5,5-tetramethyl-1,3,2-dioxaborolan-2-yl)-1-(tritylamino)pentyl)-1H-tetrazol-1-yl)acetamide

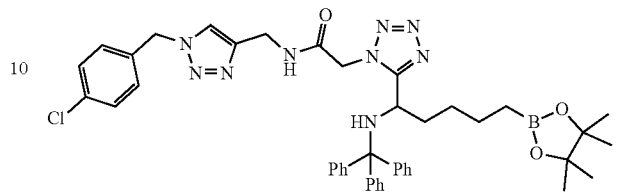

To a stirred solution of N-(prop-2-yn-1-yl)-2-(5-(5-(4,4,5,5-tetramethyl-1,3,2-dioxaborolan-2-yl)-1-(tritylamino)pentyl)-1H-tetrazol-1-yl)acetamide (0.1 g, 0.161 mmol, obtained in example 157) in DMF (1.0 mL) was added aqueous solution of Cu(II)SO$_4$·5H$_2$O (0.025 g in 0.4 mL H$_2$O, 0.097 mmol) and ascorbic acid (0.092 g in 0.4 mL H$_2$O, 0.466 mmol) respectively followed by 1-(azidomethyl)-4-chlorobenzene (0.035 g, 0.209 mmol) and further stirred for 14 h. The reaction mixture was poured on ice-cold water, solid precipitated out, collected by filtration and vacuum dried and further purified by flash chromatography to obtain title compound as a pale yellow solid (0.110 g).

$^1$H NMR (500 MHz, Chloroform-d) δ8.01 (s, 1H), 7.36-7.29 (m, 9H), 7.20-7.15 (m, 11H), 5.43-5.32 (m, 2H), 4.80 (d, J=16.5 Hz, 1H), 4.42 (dt, J=5.9, 3.0 Hz, 3H), 4.38-4.31 (m, 2H), 4.07-3.93 (m, 1H), 1.90-1.80 (m, 1H), 1.74-1.66 (m, 1H), 1.27 (ddd, J=13.3, 9.3, 6.7 Hz, 2H), 1.20 (d, J=4.3 Hz, 12H), 1.14-0.98 (m, 2H), 0.63 (tt, J=8.4, 4.1 Hz, 2H); LC-MS (EI) m/z: 785.08 (M–H)$^+$.

Example 239: N-((1-(2-fluoroethyl)-1H-1,2,3-triazol-4-yl)methyl)-2-(5-(5-(4,4,5,5-tetramethyl-1,3,2-dioxaborolan-2-yl)-1-(tritylamino)pentyl)-1H-tetrazol-1-yl)acetamide Example 239 was prepared in analogues manner of example 238, starting from appropriate intermediates that are available commercially or synthesized as above.

| Ex. No. | LC-MS (EI)m/z: | IUPAC Name |
|---|---|---|
| 239 | 730.3 (M + Na)$^+$ | N-((1-(2-fluoroethyl)-1H-1,2,3-triazol-4-yl)methyl)-2-(5-(5-(4,4,5,5-tetramethyl-1,3,2-dioxaborolan-2-yl)-1-(tritylamino)pentyl)-1H-tetrazol-1-yl)acetamide. |

Examples 240-247: Chirally Pure Compounds

Analytical Methods Used for Chiral Separation

Method-1:—Column-Chiral IC (250×4.6) mm, 5 mm; Flow: 4.0 ml min$^{-1}$; Mobile Phase: Isocratic; Ethanol: CO$_2$ (13:87); Column Temperature: 40° C., Detection wavelength: photodiode array (PDA); Pressure: 120 bar; Run length: 18 min.

Method-2: Column-Chiral IC (250×4.6) mm, 5 mm; Flow: 4.0 ml min$^{-1}$; Mobile Phase: Isocratic; Ethanol: CO$_2$ (20:80); Column Temperature: 40° C., Detection wavelength: photodiode array (PDA); Pressure: 120 bar; Run length: 15 min.

Method-3:—Column-Chiral IC (250×4.6) mm, 5 mm; Flow: 4.0 ml min$^{-1}$; Mobile Phase: Isocratic; Ethanol: CO$_2$ (14:86); Column Temperature: 40° C., Detection wavelength: photodiode array (PDA); Pressure: 120 bar; Run length: 25 min.

Method-4:—Column-Chiral IC (250×4.6) mm, 5 mm; Flow: 4.0 ml min$^{-1}$; Mobile Phase: Isocratic; Ethanol: CO$_2$ (15:85); Column Temperature: 40° C., Detection wavelength: photodiode array (PDA); Pressure: 120 bar; Run length: 30 min.

| Ex. No. | LC-MS (EI)m/z: | IUPAC Name and Chiral HPLC RT | Method Used |
|---|---|---|---|
| 240 | 641.4 (M + Na)$^+$ | (−)-N-(prop-2-yn-1-yl)-2-(5-(5-(4,4,5,5-tetramethyl-1,3,2-dioxaborolan-2-yl)-1-(tritylamino)pentyl)-1H-tetrazol-1-yl)acetamide. Peak1-RT = 10.6 min | Method 1 |
| 241 | 641.4 (M + Na)$^+$ | (+)-N-(prop-2-yn-1-yl)-2-(5-(5-(4,4,5,5-tetramethyl-1,3,2-dioxaborolan-2-yl)-1-(tritylamino)pentyl)-1H-tetrazol-1-yl)acetamide. Peak2-RT = 13 min | Method 1 |
| 242 | 727.5 (M + Na)$^+$ | (−)-(R)-N-(4-chlorobenzyl)-2-(5-(5-(4,4,5,5-tetramethyl-1,3,2-dioxaborolan-2-yl)-1-(tritylamino)pentyl)-1H-tetrazol-1-yl)acetamide. Peak1-RT = 6.5 min | Method 2 |
| 243 | 727.5 (M + Na)$^+$ | (+)-(S)-N-(4-chlorobenzyl)-2-(5-(5-(4,4,5,5-tetramethyl-1,3,2-dioxaborolan-2-yl)-1-(tritylamino)pentyl)-1H-tetrazol-1-yl)acetamide. Peak2-RT = 9.4 min | Method 2 |
| 244 | 711.4 (M + Na)$^+$ | (−)-N-(2-fluorobenzyl)-2-(5-(5-(4,4,5,5-tetramethyl-1,3,2-dioxaborolan-2-yl)-1-(tritylamino)pentyl)-1H-tetrazol-1-yl)acetamide. Peak1-RT = 15.1 min | Method 3 |
| 245 | 711.4 (M + Na)$^+$ | (+)-N-(2-fluorobenzyl)-2-(5-(5-(4,4,5,5-tetramethyl-1,3,2-dioxaborolan-2-yl)-1-(tritylamino)pentyl)-1H-tetrazol-1-yl)acetamide. Peak2-RT = 22.1 min | Method 3 |
| 246 | 707.4 (M + Na)$^+$ | (−)-N-phenethyl-2-(5-(5-(4,4,5,5-tetramethyl-1,3,2-dioxaborolan-2-yl)-1-(tritylamino)pentyl)-1H-tetrazol-1-yl)acetamide. Peak1-RT = 22.1 min | Method 4 |
| 247 | 707.4 (M + Na)$^+$ | (+)-N-phenethyl-2-(5-(5-(4,4,5,5-tetramethyl-1,3,2-dioxaborolan-2-yl)-1-(tritylamino)pentyl)-1H-tetrazol-1-yl)acetamide. Peak2-RT = 22.1 min | Method 4 |

Example 248: (5-amino-5-(1-(4-chlorobenzyl)-1H-tetrazol-5-yl)pentyl)boronic acid hydrochloride

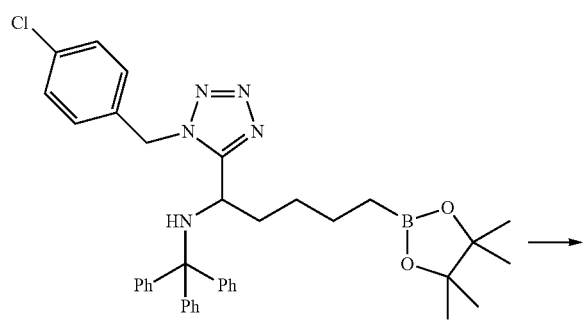

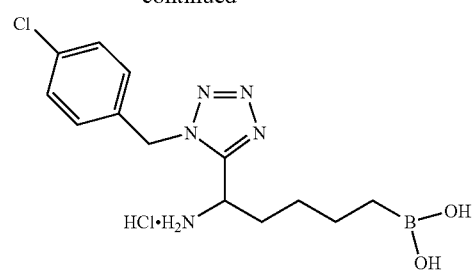

1-(1-(4-chlorobenzyl)-1H-tetrazol-5-yl)-5-(4,4,5,5-tetramethyl-1,3,2-dioxaborolan-2-yl)-N-tritylpentan-1-amine (0.2 g, 0.308 mmol, obtained in example 129) was dissolved in DCM (1.0 mL) to it was added 3N aqueous HCl (5.0 mL) and resulted reaction mixture was heated at 70° C. for 18 h. The reaction mixture was further diluted with 5.0 mL water and the aqueous layer was washed with DCM (2×10 mL). The aqueous phase was concentrated to dryness under reduced pressure afforded the title off white solid (0.095 g).

$^1$H NMR (500 MHz, Methanol-d$_4$) δ7.43 (d, J=8.2 Hz, 2H), 7.36 (d, J=8.5 Hz, 2H), 5.85 (d, J=15.7 Hz, 1H), 5.70 (d, J=15.7 Hz, 1H), 3.64-3.53 (m, 1H), 1.94-1.74 (m, 2H), 1.27-1.08 (m, 2H), 1.08-0.88 (m, 2H), 0.60 (t, J=7.7 Hz, 2H); LC-MS (EI) m/z: 338.1 (M+15)$^+$.

Example 249: (5-amino-5-(1-(2-fluoro-5-nitrophenyl)-1H-tetrazol-5-yl)pentyl)boronic acid hydrochloride

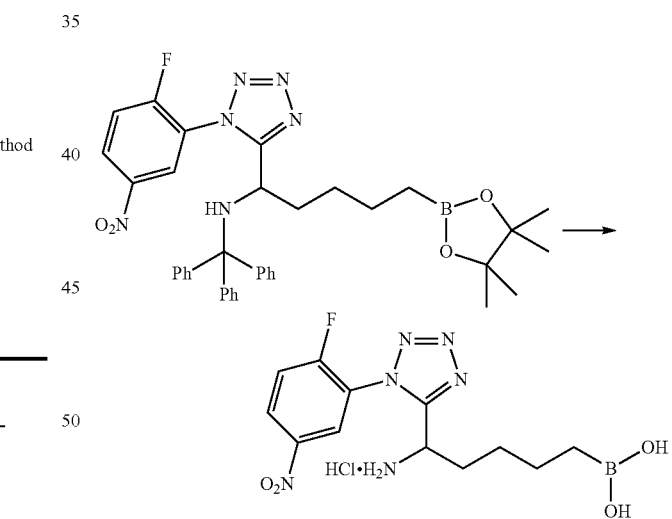

The compound of example 249 was obtained by similar method described in example 248 using 1-(1-(2-fluoro-5-nitrophenyl)-1H-tetrazol-5-yl)-5-(4,4,5,5-tetramethyl-1,3,2-dioxaborolan-2-yl)-N-tritylpentan-1-amine (0.1 g, 0.15 mmol, obtained in example 130) in DCM (0.5 mL), 3N aqueous HCl (3.0 mL) heated at 70° C. for 18 h to provide the title compound (0.050 g)

$^1$H NMR (500 MHz, Methanol-d$_4$) δ8.64 (dt, J=9.0, 2.6 Hz, 1H), 8.61 (t, J=2.5 Hz, 1H), 7.86 (dd, J=8.9, 2.3 Hz, 1H), 4.79-4.71 (m, 1H), 2.07-1.88 (m, 2H), 1.38-1.08 (m, 4H), 0.78-0.59 (m, 2H); LC-MS (EI) m/z: 339.1 (M+H)$^+$.

Example 250: 2-(5-(1-amino-5-(4,4,5,5-tetramethyl-1,3,2-dioxaborolan-2-yl)pentyl)-1H-tetrazol-1-yl) acetic acid hydrochloride

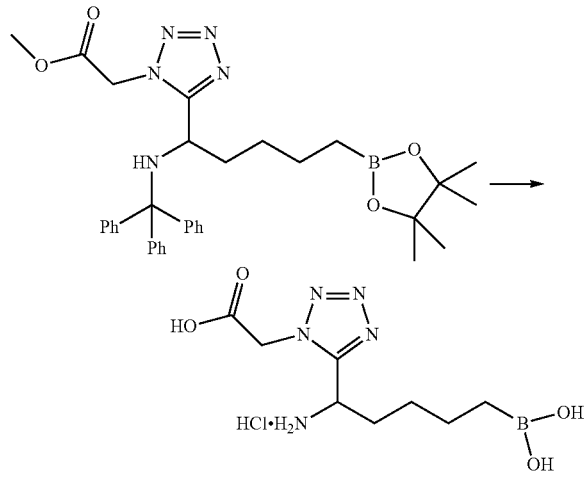

The compound of example 250 was obtained by similar method described in example 248 using Methyl 2-(5-(5-(4,4,5,5-tetramethyl-1,3,2-dioxaborolan-2-yl)-1-(tritylamino)pentyl)-1H-tetrazol-1-yl)acetate (0.2 g, 0.335 mmol, obtained in example 131) in DCM (0.5 mL), 3N aqueous HCl (5.0 mL) heated at 100° C. for 18 h to provide the title compound (0.090 g) NMR; LC-MS (EI) m/z: 256.2 (M−H)+.

Example 251: (5-amino-5-(1H-tetrazol-5-yl)hexyl)boronic acid hydrochloride

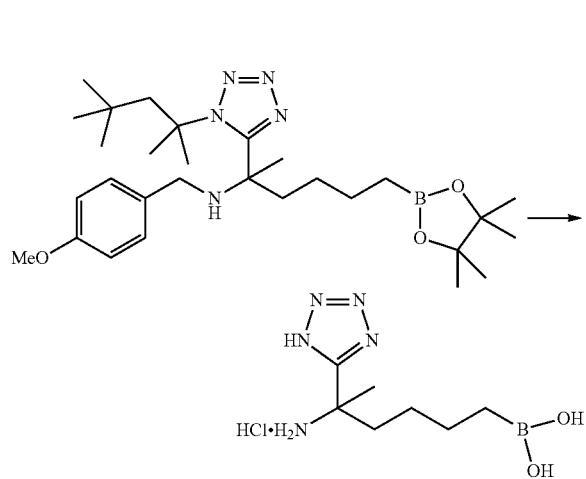

The compound of example 251 was obtained by similar method described in example 248 using N-(4-methoxybenzyl)-6-(4,4,5,5-tetramethyl-1,3,2-dioxaborolan-2-yl)-2-(1-(2,4,4-trimethylpentan-2-yl)-1H-tetrazol-5-yl)hexan-2-amine (0.1 g, 0.335 mmol, obtained in example 136) in DCM (0.5 mL), 3N aqueous HCl (3.0 mL) heated at 100° C. for 18 h to provide the title compound (0.040 g)

$^1$H NMR (500 MHz, Methanol-$d_4$) δ2.15-2.00 (m, 2H), 1.80 (s, 3H), 1.42-1.31 (m, 2H), 1.30-1.14 (m, 3H), 0.81-0.69 (m, 2H); LC-MS (EI) m/z: 228.2 (M+15)+.

Example 252: (6-amino-6-(1H-tetrazol-5-yl)hexyl)boronic acid hydrochloride

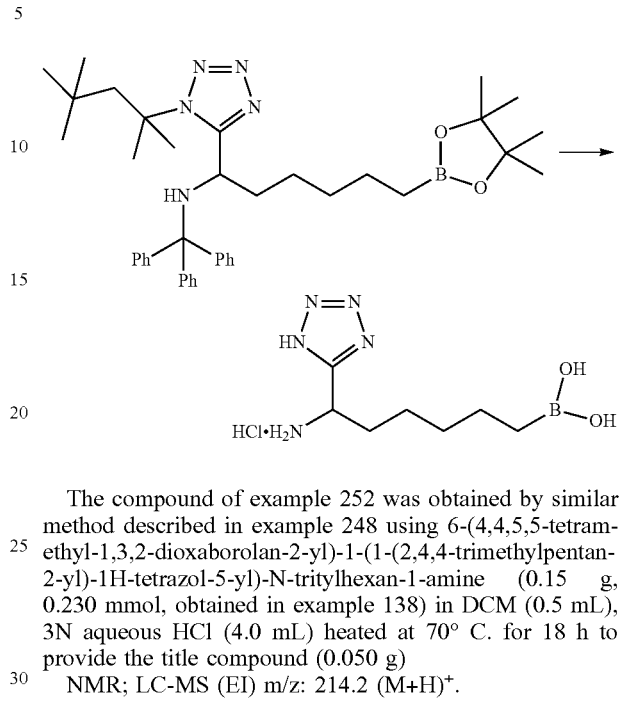

The compound of example 252 was obtained by similar method described in example 248 using 6-(4,4,5,5-tetramethyl-1,3,2-dioxaborolan-2-yl)-1-(1-(2,4,4-trimethylpentan-2-yl)-1H-tetrazol-5-yl)-N-tritylhexan-1-amine (0.15 g, 0.230 mmol, obtained in example 138) in DCM (0.5 mL), 3N aqueous HCl (4.0 mL) heated at 70° C. for 18 h to provide the title compound (0.050 g)

NMR; LC-MS (EI) m/z: 214.2 (M+H)+.

Example 253: (5-amino-5-(1-(2-((2-fluorobenzyl)amino)-2-oxoethyl)-1H-tetrazol-5-yl)pentyl)boronic acid hydrochloride

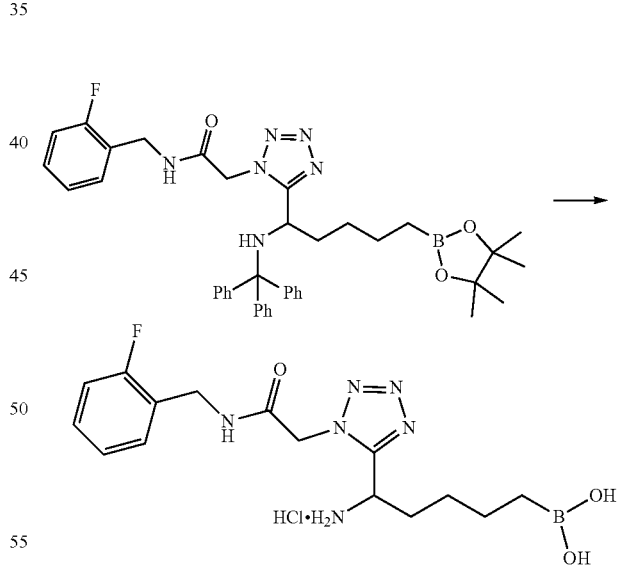

The compound of example 253 was obtained by similar method described in example 248 using N-(2-fluorobenzyl)-2-(5-(5-(4,4,5,5-tetramethyl-1,3,2-dioxaborolan-2-yl)-1-(tritylamino)pentyl)-1H-tetrazol-1-yl)acetamide (0.15 g, 0.217 mmol, obtained in example 231) in DCM (0.5 mL), 3N aqueous HCl (4.0 mL) heated at 70° C. for 18 h to provide the title compound (0.080 g)

(Major rotamer is given) $^1$H NMR (500 MHz, Deuterium Oxide) δ7.43-7.35 (m, 2H), 7.21-7.11 (m, 2H), 5.45 (q, J=35.5, 17.7 Hz, 2H), 4.89 (t, J=7.1 Hz, 1H), 4.17 (s, 2H), 2.16-1.99 (m, 2H), 1.37-1.09 (m, 4H), 0.64 (t, J=7.8 Hz, 2H); LC-MS (EI) m/z: 379.2 (M+15)$^+$.

Example 254 to 362 were prepared in analogues manner of example 248-253 from the appropriate intermediate that are available commercially or synthesized as above.

| Ex. No | LC-MS (EI) m/z: | IUPAC Name |
|---|---|---|
| 254 | 304.2 (M + 15)$^+$ | (5-amino-5-(1-benzyl-1H-tetrazol-5-yl)pentyl)boronic acid hydrochloride. |
| 255 | 228.1 (M + 15)$^+$ | (5-(methylamino)-5-(1H-tetrazol-5-yl)pentyl)boronic acid hydrochloride. |
| 256 | 322.2 (M + 15) | (5-amino-5-(1-(3-fluorobenzyl)-1H-tetrazol-5-yl)pentyl) boronic acid hydrochloride. |
| 257 | 318.2 (M + 15)$^+$ | (5-amino-5-(1-phenethyl-1H-tetrazol-5-yl)pentyl)boronic acid hydrochloride. |
| 258 | 296.2 (M + 15)$^+$ | (5-amino-5-(1-cyclohexyl-1H-tetrazol-5-yl)pentyl)boronic acid hydrochloride. |
| 259 | 214.2 (M + 15)$^+$ | (5-amino-5-(1H-tetrazol-5-yl)pentyl)boronic acid hydrochloride. |
| 260 | 347.2 (M + H)$^+$ | (5-amino-5-(1-(2-(benzylamino)-2-oxoethyl)-1H-tetrazol-5-yl)pentyl)boronic acid hydrochloride. |
| 261 | 409.2 (M + H)$^+$ | (5-(1-(2-fluoro-5-nitrophenyl)-1H-tetrazol-5-yl)-5-morpholinopentyl)boronicacid hydrochloride. |
| 262 | 406.2 (M + H)$^+$ | (5-amino-5-(1-(2-morpholino-5-nitrophenyl)-1H-tetrazol-5-yl)pentyl)boronicacid hydrochloride |
| 262 | 228.2 (M + 15)$^+$ | (5-amino-5-(1H-tetrazol-5-yl)hexyl)boronicacid hydrochloride. |
| 263 | 381.1 (M + H)$^+$ | (5-amino-5-(1-(2-((4-chlorobenzyl)amino)-2-oxoethyl)-1H-tetrazol-5-yl)pentyl)boronic acid hydrochloride. |
| 264 | 361.2 (M + H)$^+$ | (5-amino-5-(1-(2-oxo-2-(((S)-1-phenylethyl)amino)ethyl)-1H-tetrazol-5-yl)pentyl)boronic acid hydrochloride. |
| 265 | 353.2 (M + H)$^+$ | (5-amino-5-(1-(2-oxo-2-((thiophen-2-ylmethyl)amino)ethyl)-1H-tetrazol-5-yl)pentyl)boronic acid hydrochloride. |
| 266 | 361.2 (M + H)$^+$ | 5-Amino-5-(1-(2-oxo-2-(phenethylamino)ethyl)-1H-tetrazol-5-yl)pentyl)boronic acid hydrochloride. |
| 267 | 430.3 (M + H)$^+$ | (5-amino-5-(1-(2-((1-benzylpiperidin-4-yl)amino)-2-oxoethyl)-1H-tetrazol-5-yl)pentyl)boronic acid hydrochloride. |
| 268 | 297.2 (M + H)$^+$ | (5-amino-5-(1-(2-(cyclopropylamino)-2-oxoethyl)-1H-tetrazol-5-yl)pentyl)boronic acid hydrochloride. |
| 269 | 370.4 (M + H)$^+$ | (5-amino-5-(1-(2-((2-morpholinoethyl)amino)-2-oxoethyl)-1H-tetrazol-5-yl)pentyl)boronic acid hydrochloride. |
| 270 | 421.2 (M + H)$^+$ | (5-amino-5-(1-(2-((3,4-dimethoxyphenethyl)amino)-2-oxoethyl)-1H-tetrazol-5-yl)pentyl)boronic acid hydrochloride. |
| 271 | 297.1 (M + H)$^+$ | (5-amino-5-(1-(2-(butylamino)-2-oxoethyl)-1H-tetrazol-5-yl)pentyl)boronic acid hydrochloride. |
| 272 | 295.1 (M + H)$^+$ | (5-amino-5-(1-(2-oxo-2-(prop-2-yn-1-ylamino)ethyl)-1H-tetrazol-5-yl)pentyl)boronic acid hydrochloride. |
| 273 | 416.2 (M + H)$^+$ | (5-amino-5-(1-(2-(4-benzylpiperazin-1-yl)-2-oxoethyl)-1H-tetrazol-5-yl)pentyl)boronic acid hydrochloride. |
| 274 | 416.2 (M + H)$^+$ | (5-amino-5-(1-(2-morpholino-2-oxoethyl)-1H-tetrazol-5-yl)pentyl)boronic acid hydrochloride. |
| 275 | 311.2 (M + H)$^+$ | (5-amino-5-(1-(2-oxo-2-(pyrrolidin-1-yl)ethyl)-1H-tetrazol-5-yl)pentyl)boronic acid hydrochloride. |
| 276 | 381.2 (M + H)$^+$ | (5-amino-5-(1-(2-((3-chlorobenzyl)amino)-2-oxoethyl)-1H-tetrazol-5-yl)pentyl)boronic acid hydrochloride. |
| 277 | 381.2 (M + H)$^+$ | (5-amino-5-(1-(2-((2-chlorobenzyl)amino)-2-oxoethyl)-1H-tetrazol-5-yl)pentyl)boronic acid hydrochloride. |
| 278 | 348.2 (M + H)$^+$ | (5-amino-5-(1-(2-oxo-2-((pyridin-3-ylmethyl)amino)ethyl)-1H-tetrazol-5-yl)pentyl)boronic acid hydrochloride. |
| 279 | 377.2 (M + H)$^+$ | (5-amino-5-(1-(2-((4-methoxybenzyl)amino)-2-oxoethyl)-1H-tetrazol-5-yl)pentyl)boronic acid hydrochloride. |
| 280 | 348.2 (M + H)$^+$ | (5-amino-5-(1-(2-oxo-2-((pyridin-4-ylmethyl)amino)ethyl)-1H-tetrazol-5-yl)pentyl)boronic acid hydrochloride. |
| 281 | 395.2 (M + H)$^+$ | (5-amino-5-(1-(3-((4-chlorobenzyl)amino)-3-oxopropyl)-1H-tetrazol-5-yl)pentyl)boronic acid hydrochloride. |
| 282 | 375.2 (M + H)$^+$ | (5-amino-5-(1-(3-oxo-3-(phenethylamino)propyl)-1H-tetrazol-5-yl)pentyl)boronic acid hydrochloride. |
| 283 | 284.1 (M − H)$^+$ | 4-(5-(1-amino-5-boronopentyl)-1H-tetrazol-1-yl)butanoic acid hydrochloride. |
| 284 | 243.2 (M + H)$^+$ | (5-(1-(2-(1H-indol-3-yl)ethyl)-1H-tetrazol-5-yl)-5-aminopentyl)boronic acid hydrochloride. |
| 285 | 405.3 (M + 15)$^+$ | (5-amino-5-(1-(2-(benzyl(2-hydroxyethyl)amino)-2-oxoethyl)-1H-tetrazol-5-yl)pentyl)boronic acid hydrochloride. |
| 286 | 361.2 (M + H)$^+$ | (5-amino-5-(1-(2-(benzyl(methyl)amino)-2-oxoethyl)-1H-tetrazol-5-yl)pentyl)boronic acid hydrochloride. |
| 287 | 395.3 (M + H)$^+$ | (5-amino-5-(1-(2-(((S)-1-(4-chlorophenyl)ethyl)amino)-2-oxoethyl)-1H-tetrazol-5-yl)pentyl)boronic acid hydrochloride. |
| 288 | 318.2 (M + 15)$^+$ | (5-amino-5-(1-(1-phenylethyl)-1H-tetrazol-5-yl)pentyl)boronic acid hydrochloride. |
| 289 | 318.2 (M + 15)$^+$ | (5-amino-5-(1-((S)-1-phenylethyl)-1H-tetrazol-5-yl)pentyl)boronic acid hydrochloride. |
| 290 | 318.2 (M + 15)$^+$ | (5-amino-5-(1-((R)-1-phenylethyl)-1H-tetrazol-5-yl)pentyl)boronic acid hydrochloride. |
| 291 | 352.2 (M + 15)$^+$ | (5-amino-5-(1-((S)-1-(4-chlorophenyl)ethyl)-1H-tetrazol-5-yl)pentyl)boronic acid hydrochloride. |
| 292 | 352.2 (M + 15)$^+$ | (5-amino-5-(1-((R)-1-(4-chlorophenyl)ethyl)-1H-tetrazol-5-yl)pentyl)boronic acid hydrochloride. |
| 293 | 348.2 (M + 15)$^+$ | (5-amino-5-(1-((R)-1-(4-methoxyphenyl)ethyl)-1H-tetrazol-5-yl)pentyl)boronic acid hydrochloride. |
| 294 | 322.1 (M + 15)$^+$ | (5-amino-5-(1-(4-fluorobenzyl)-1H-tetrazol-5-yl)pentyl)boronic acid hydrochloride. |
| 295 | 322.1 (M + 15)$^+$ | (5-amino-5-(1-(2-fluorobenzyl)-1H-tetrazol-5-yl)pentyl)boronic acid hydrochloride. |
| 296 | 338.2 (M + 15)$^+$ | (5-amino-5-(1-(3-chlorobenzyl)-1H-tetrazol-5-yl)pentyl)boronic acid hydrochloride. |
| 297 | 338.2 (M + 15)$^+$ | (5-amino-5-(1-(2-chlorobenzyl)-1H-tetrazol-5-yl)pentyl)boronic acid hydrochloride. |
| 298 | 381.1 [M (Br$^{79}$) + 15]$^+$; 383.1 [M (Br$^{81}$) + 15]$^+$ | (5-amino-5-(1-(4-bromobenzyl)-1H-tetrazol-5-yl)pentyl)boronic acid hydrochloride. |
| 299 | 329.2 (M + 15)$^+$ | (5-amino-5-(1-(4-cyanobenzyl)-1H-tetrazol-5-yl)pentyl)boronic acid hydrochloride. |
| 300 | 372.0 (M + 15)$^+$ | (5-amino-5-(1-(2,4-dichlorobenzyl)-1H-tetrazol-5-yl)pentyl)boronic acid hydrochloride. |
| 301 | 372.0 (M + 15)$^+$ | (5-amino-5-(1-(3,4-dichlorobenzyl)-1H-tetrazol-5-yl)pentyl)boronic acid hydrochloride. |
| 302 | 399.1 [M (Br$^{79}$) + 15]$^+$; 401.1 [M (Br$^{81}$) + 15]$^+$ | (5-amino-5-(1-(4-bromo-2-fluorobenzyl)-1H-tetrazol-5-yl)pentyl)boronic acid hydrochloride. |
| 303 | 334.2 (M + 15)$^+$ | (5-amino-5-(1-(2-methoxybenzyl)-1H-tetrazol-5-yl)pentyl)boronic acid hydrochloride. |
| 304 | 334.2 (M + H)$^+$ | (5-amino-5-(1-(3-hydroxy-1-phenylpropyl)-1H-tetrazol-5-yl)pentyl)boronic acid hydrochloride. |
| 305 | 305.2 (M + 15)$^+$ | (5-amino-5-(1-(pyridin-3-ylmethyl)-1H-tetrazol-5-yl)pentyl)boronic acid hydrochloride. |
| 306 | 310.1 (M + 15)$^+$ | (5-amino-5-(1-(thiophen-2-ylmethyl)-1H-tetrazol-5-yl)pentyl)boronic acid hydrochloride. |
| 307 | 336.2 (M + 15)$^+$ | (5-amino-5-(1-(4-fluorophenethyl)-1H-tetrazol-5-yl)pentyl)boronic acid hydrochloride. |
| 308 | 378.2 (M + 15)$^+$ | (5-amino-5-(1-(3,4-dimethoxyphenethyl)-1H-tetrazol-5-yl)pentyl)boronic acid hydrochloride. |
| 309 | 348.2 (M + 15)$^+$ | (5-amino-5-(1-(2-methoxyphenethyl)-1H-tetrazol-5-yl)pentyl)boronic acid hydrochloride. |

-continued

| Ex. No | LC-MS (EI) m/z: | IUPAC Name |
|---|---|---|
| 310 | 318.3 (M − H)+ | (5-amino-5-(1-(4-hydroxyphenethyl)-1H-tetrazol-5-yl)pentyl)boronic acid hydrochloride. |
| 311 | 348.2 (M + 15)+ | (5-amino-5-(1-(3-methoxyphenethyl)-1H-tetrazol-5-yl)pentyl)boronic acid hydrochloride. |
| 312 | 332.2 (M + 15)+ | (5-amino-5-(1-(3-phenylpropyl)-1H-tetrazol-5-yl)pentyl)boronic acid hydrochloride. |
| 313 | 431.1 [M (Br79) + 15]+; 433.1 [M (Br81) + 15]+ | (5-amino-5-(1-(4-bromophenethyl)-1H-tetrazol-5-yl)pentyl)boronic acid hydrochloride. |
| 314 | 340.2 (M + 15)+ | (5-amino-5-(1-(2,5-difluorobenzyl)-1H-tetrazol-5-yl)pentyl)boronic acid hydrochloride. |
| 315 | 383.1 (M + H)+ | (5-amino-5-(1-(2-((2,4-difluorobenzyl)amino)-2-oxoethyl)-1H-tetrazol-5-yl)pentyl)boronic acid hydrochloride. |
| 316 | 361.2 (M + 15)+ | (5-amino-5-(1-(2-((4-methylbenzyl)amino)-2-oxoethyl)-1H-tetrazol-5-yl)pentyl)boronic acid hydrochloride. |
| 317 | 395.2 (M + 15)+ | (5-amino-5-(1-(2-((4-chlorophenethyl)amino)-2-oxoethyl)-1H-tetrazol-5-yl)pentyl)boronic acid hydrochloride. |
| 318 | 435.3 (M + 15)+ | (5-amino-5-(1-(2-((4-chloro-2-fluorobenzyl)amino)-2-oxoethyl)-1H-tetrazol-5-yl)pentyl)boronic acid hydrochloride. |
| 319 | 383.1 (M + 15)+ | (5-amino-5-(1-(2-((2,6-difluorobenzyl)amino)-2-oxoethyl)-1H-tetrazol-5-yl)pentyl)boronic acid hydrochloride. |
| 320 | 386.2 (M + 15)+ | (5-amino-5-(1-(2-((4-cyanobenzyl)amino)-2-oxoethyl)-1H-tetrazol-5-yl)pentyl)boronic acid hydrochloride. |
| 321 | 437.2 (M + 15)+ | (5-amino-5-(1-(1-((4-chlorobenzyl)amino)-3-methyl-1-oxobutan-2-yl)-1H-tetrazol-5-yl)pentyl)boronic acid hydrochloride. |
| 322 | 451.3 (M + 15)+ | (5-amino-5-(1-(1-((4-chlorobenzyl)amino)-4-methyl-1-oxopentan-2-yl)-1H-tetrazol-5-yl)pentyl)boronic acid hydrochloride |
| 323 | 424.1 [M (Br79) + H]+; 426.1 [M (Br81) + H]+ | (5-amino-5-(1-(2-((4-bromobenzyl)amino)-2-oxoethyl)-1H-tetrazol-5-yl)pentyl)boronic acid hydrochloride. |
| 324 | 375.2 (M + 15)+ | (6-amino-6-(1-(2-(benzylamino)-2-oxoethyl)-1H-tetrazol-5-yl)hexyl)boronic acid hydrochloride. |
| 325 | 409.2 (M + 15)+ | (6-amino-6-(1-(2-((4-chlorobenzyl)amino)-2-oxoethyl)-1H-tetrazol-5-yl)hexyl)boronic acid hydrochloride. |
| 326 | 443.2 (M + 15)+ | (6-amino-6-(1-(2-((2,4-dichlorobenzyl)amino)-2-oxoethyl)-1H-tetrazol-5-yl)hexyl)boronic acid hydrochloride. |
| 327 | 323.2 (M + 15)+ | (6-amino-6-(1-(2-oxo-2-(prop-2-yn-1-ylamino)ethyl)-1H-tetrazol-5-yl)hexyl)boronic acid hydrochloride. |
| 328 | 389.3 (M + 15)+ | (6-amino-6-(1-(2-oxo-2-(phenethylamino)ethyl)-1H-tetrazol-5-yl)hexyl)boronic acid hydrochloride. |
| 329 | 451.1 (M + 15)+ | (5-amino-5-(1-(2-oxo-2-(((perfluorophenyl)methyl)amino)ethyl)-1H-tetrazol-5-yl)pentyl)boronic acid hydrochloride. |
| 330 | 433.1 (M + 15)+ | (5-amino-5-(1-(2-oxo-2-((2,3,4,5-tetrafluorobenzyl)amino)ethyl)-1H-tetrazol-5-yl)pentyl)boronic acid hydrochloride. |
| 331 | 415.2 (M + 15)+ | (5-amino-5-(1-(2-oxo-2-((2,4,6-trifluorobenzyl)amino)ethyl)-1H-tetrazol-5-yl)pentyl)boronic acid hydrochloride. |
| 332 | 396.3 (M + 15)+ | (5-amino-5-(1-(2-(((6-chloropyridin-3-yl)methyl)amino)-2-oxoethyl)-1H-tetrazol-5-yl)pentyl)boronic acid hydrochloride. |
| 333 | 379.2 (M + 15)+ | (5-amino-5-(1-(2-((3-fluorobenzyl)amino)-2-oxoethyl)-1H-tetrazol-5-yl)pentyl)boronic acid hydrochloride. |
| 334 | 383.1 (M + 15)+ | (5-amino-5-(1-(2-((2,3-difluorobenzyl)amino)-2-oxoethyl)-1H-tetrazol-5-yl)pentyl)boronic acid hydrochloride. |
| 335 | 383.1 (M + 15)+ | (5-amino-5-(1-(2-((2,5-difluorobenzyl)amino)-2-oxoethyl)-1H-tetrazol-5-yl)pentyl)boronic acid hydrochloride. |
| 336 | 383.1 (M + 15)+ | (5-amino-5-(1-(2-((3,5-difluorobenzyl)amino)-2-oxoethyl)-1H-tetrazol-5-yl)pentyl)boronic acid hydrochloride. |
| 337 | 415.2 (M + 15)+ | (5-amino-5-(1-(2-oxo-2-((2,3,4-trifluorobenzyl)amino)ethyl)-1H-tetrazol-5-yl)pentyl)boronic acid hydrochloride. |
| 338 | 415.2 (M + 15)+ | (5-amino-5-(1-(2-oxo-2-((2,3,5-trifluorobenzyl)amino)ethyl)-1H-tetrazol-5-yl)pentyl)boronic acid hydrochloride. |
| 339 | 415.2 (M + 15)+ | (5-amino-5-(1-(2-oxo-2-((3,4,5-trifluorobenzyl)amino)ethyl)-1H-tetrazol-5-yl)pentyl)boronic acid hydrochloride |
| 340 | 415.2 (M + 15)+ | (5-amin o-5-(1-(2-oxo-2-((2,3,6-trifluorobenzyl)amino)ethyl)-1H-tetrazol-5-yl)pentyl)boronic acid hydrochloride. |
| 341 | 433.1 (M + 15)+ | (5-amino-5-(1-(2-oxo-2-((2,3,5,6-tetrafluorobenzyl)amino)ethyl)-1H-tetrazol-5-yl)pentyl)boronic acid hydrochloride. |
| 342 | 383.1 (M + 15)+ | (5-amino-5-(1-(2-((3,4-difluorobenzyl)amino)-2-oxoethyl)-1H-tetrazol-5-yl)pentyl)boronic acid hydrochloride. |
| 343 | 415.2 (M + 15)+ | (5-amino-5-(1-(2-oxo-2-((2,4,5-trifluorobenzyl)amino)ethyl)-1H-tetrazol-5-yl)pentyl)boronic acid hydrochloride. |
| 344 | 435.8 (M + 15)+ | (5-amino-5-(1-(((1-(4-chlorobenzyl)piperidin-4-yl)methyl)-1H-tetrazol-5-yl)pentyl)boronic acid hydrochloride. |
| 345 | 375.2 (M + 15)+ | (5-amino-5-(1-(2-oxo-2-(((R)-1-phenylethyl)amino)ethyl)-1H-tetrazol-5-yl)pentyl)boronic acid hydrochloride. |
| 346 | 398.2 (M + 15)+ | (5-amino-5-(1-(2-(((1-(2-fluoroethyl)-1H-1,2,3-triazol-4-yl)methyl)amino)-2-oxoethyl)-1H-tetrazol-5-yl)pentyl)boronic acid hydrochloride. |
| 347 | 395.2 (M + 15)+ | (5-amino-5-(1-(2-(4-chlorobenzamido)ethyl)-1H-tetrazol-5-yl)pentyl)boronic acid hydrochloride. |
| 348 | 476.2 (M + 15)+ | (5-amino-5-(1-(2-(((1-(4-chlorobenzyl)-1H-1,2,3-triazol-4-yl)methyl)amino)-2-oxoethyl)-1H-tetrazol-5-yl)pentyl)boronic acid hydrochloride. |
| 349 | 486.2 (M + 15)+ | (5-(1-(2-((4-chlorobenzyl)amino)-2-oxoethyl)-1H-tetrazol-5-yl)-5-((pyridin-4-ylmethyl)amino)pentyl)boronic acid hydrochloride. |
| 350 | 492.3 (M + 15)+ | (5-(4-(aminomethyl)piperidin-1-yl)-5-(1-(2-((4-chlorobenzyl)amino)-2-oxoethyl)-1H-tetrazol-5-yl)pentyl)boronic acid hydrochloride. |
| 351 | 492.2 (M + 15)+ | (5-(1-(2-((4-chlorobenzyl)amino)-2-oxoethyl)-1H-tetrazol-5-yl)-5-((1-methylpiperidin-4-yl)amino)pentyl)boronic acid hydrochloride. |
| 352 | 437.2 (M + 15)+ | (5-(1-(2-(([1,1'-biphenyl]-4-ylmethyl)amino)-2-oxoethyl)-1H-tetrazol-5-yl)-5-aminopentyl)boronic acid |
| 353 | 428.2 (M + 15)+ | (5-(1-(2-(((6-(1H-imidazol-1-yl)pyridin-3-yl)methyl)amino)-2-oxoethyl)-1H-tetrazol-5-yl)-5-aminopentyl)boronic acid hydrochloride. |
| 354 | 381.3 (M + 15)+ | (5-amino-5-(1-(2-((4-chlorophenyl)amino)-2-oxoethyl)-1H-tetrazol-5-yl)pentyl)boronic acid hydrochloride. |
| 355 | 295.1 (M + H)+ | (+)-(R)-(5-amino-5-(1-(2-oxo-2-(prop-2-yn-1-ylamino)ethyl)-1H-tetrazol-5-yl)pentyl)boronic acid hydrochloride. |
| 356 | 295.1 (M + H)+ | (−)-(S)-(5-amino-5-(1-(2-oxo-2-(prop-2-yn-1-ylamino)ethyl)-1H-tetrazol-5-yl)pentyl)boronic acid hydrochloride. |
| 357 | 381.1 (M + H)+ | (+)-(R)-(5-amino-5-(1-(2-((4-chlorobenzyl)amino)-2-oxoethyl)-1H-tetrazol-5-yl)pentyl)boronic acid hydrochloride. |
| 358 | 365.2 (M + H)+ | (−)-(S)-(5-amino-5-(1-(2-((4-chlorobenzyl)amino)-2-oxoethyl)-1H-tetrazol-5-yl)pentyl)boronic acid hydrochloride. |
| 359 | 365.2 (M + H)+ | (+)-(R)-(5-amino-5-(1-(2-((2-fluorobenzyl)amino)-2-oxoethyl)-1H-tetrazol-5-yl)pentyl)boronic acid hydrochloride. |

53

-continued

| Ex. No | LC-MS (EI) m/z: | IUPAC Name |
|---|---|---|
| 360 | 365.2 (M + H)+ | (−)-(S)-(5-amino-5-(1-(2-((2-fluorobenzyl)amino)-2-oxoethyl)-1H-tetrazol-5-yl)pentyl)boronic acid hydrochloride. |
| 361 | 361.2 (M + H)+ | (+)-(R)-(5-amino-5-(1-(2-oxo-2-(phenethylamino)ethyl)-1H-tetrazol-5-yl)pentyl)boronic acid hydrochloride. |
| 362 | 361.2 (M + H)+ | (−)-(S)-(5-amino-5-(1-(2-oxo-2-(phenethylamino)ethyl)-1H-tetrazol-5-yl)pentyl)boronic acid hydrochloride. |
| 363 | 365.2 (M + H)+ | (5-amino-5-(1-(2-((4-fluorobenzyl)amino)-2-oxoethyl)-1H-tetrazol-5-yl)pentyl)boronic acid hydrochloride. |

Example 364: (5-amino-5-(1-(5-amino-2-fluorophenyl)-1H-tetrazol-5-yl)pentyl)boronic acid hydrochloride

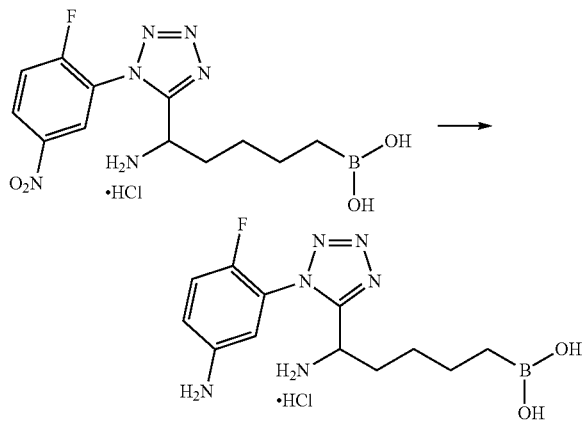

Under the nitrogen atmosphere to the stirred solution of (5-amino-5-(1-(2-fluoro-5-nitrophenyl)-1H-tetrazol-5-yl)pentyl)boronic acid hydrochloride (0.080 g, obtained in example 249) in methanol (3.0 mL) was added 10% Pd/C (0.030 g) and hydrogenation reaction was carried out using hydrogen balloon for 2.5 h. Reaction mixture was filtered through the celite pad. The Celite pad was washed with excess methanol. Finally solvent was removed under reduced pressure to obtain the title compound (0.035 g).

$^1$H NMR (500 MHz, Methanol-$d_4$) δ 6.89 (t, J=2.4 Hz, 2H), 6.62 (s, 1H), 4.54-4.42 (m, 1H), 2.05-1.78 (m, 2H), 1.36-1.16 (m, 4H), 0.68 (t, J=6.9 Hz, 2H); LC-MS (EI) m/z: 323.2 (M+15)+.

Examples 365 and 366 were prepared in analogues manner of example 355 from the appropriate intermediate that are available commercially or synthesized as above.

| Ex. No | LC-MS (EI)m/z: | IUPAC Name |
|---|---|---|
| 365 | 376.2 (M + 15)+ | 5-amino-5-(1-(5-amino-2-morpholinophenyl)-1H-tetrazol-5-yl)pentyl)boronic acid hydrochloride. |
| 366 | 438.2 (M + 15)+ | (5-amino-5-(1-(5-amino-2-(1,1-dioxidothiomorpholino)phenyl)-1H-tetrazol-5-yl)pentyl)boronic acid hydrochloride. |

54

Inhibition of Arginase

The compounds of the present invention inhibit human arginase I (ARG I) and arginase II (ARG II) as evidenced by an ex vivo assay set forth by a published protocol (Baggio et al. *J. Pharmacol. Exp. Ther.* 1999, 290, 1409-1416). The assay established the concentration of inhibitor that is required to reduce arginase activity by 50% ($IC_{50}$).

Assay Protocol

Inhibition of arginase I (ARG I) and arginase II (ARGG II) novel compounds is followed spectrophotometrically at 530 nm. The compound to be tested is dissolved in $H_2O$ and prepared 100 mM stock solution. 10 μl of the stock solution is diluted in 90 μl of the assay buffer that comprises 0.1M sodium phosphate buffer containing 130 mM NaCl, pH 7.4, to which is added ovalbumin (OVA) at a concentration of 1 mg/ml. Solutions of arginase I and II are prepared in 100 mM sodium phosphate buffer, pH 7.4 containing 1 mg/ml OVA to give an arginase stock solution at a final concentration of 100 ng/ml. To each well of a 96-well microtiter plate is add 40 μl of enzyme, 10 μl of an inventive compound and 10 μl of enzyme substrate (L-arginine+manganese sulfate). For wells that are used as positive controls, only the enzyme and its substrate are added, while wells used as negative controls contain only manganese sulfate. After incubating the microtiter plate at 37° C. for 60 minutes, 150 μl of a urea reagent obtained by combining equal proportions (1:1) of reagents A and B is added to each well of the microtiter plate to stop the reaction. The urea reagent is made just before use by combining Reagent A (10 mM o-phthaldialdehyde, and 0.4% polyoxyethylene (23) lauryl ether (w/v) in 1.8 M sulfuric acid) with Reagent B (1.3 mM primaquinone diphosphate, 0.4% polyoxyethylene (23) lauryl ether (w/v), 130 mM boric acid in 3.6 M sulfuric acid). After quenching the reaction mixture, the microtiter plate is allowed to stand for an additional 10 minutes at room temperature to allow color development. The inhibition of arginase is computed by measuring the optical density (OD) of the reaction mixture at 530 nm and normalizing the OD value to percent inhibition observed in the control. The normalized OD is then used to generate a dose-response curve by plotting the normalized OD values against log [concentration] and using regression analysis to compute the $IC_{50}$ values.

Arginase $IC_{50}$ Values

TABLE 1

| Example No | IUPAC Name | rhArg I ($IC_{50}$) | rhArg II ($IC_{50}$) |
|---|---|---|---|
| 248 | (5-amino-5-(1-(4-chlorobenzyl)-1H-tetrazol-5-yl)pentyl)boronic acid hydrochloride. | >100 | |
| 249 | (5-amino-5-(1-(2-fluoro-5-nitrophenyl)-1H-tetrazol-5-yl)pentyl)boronic acid hydrochloride. | >100 | |
| 250 | 2-(5-(1-amino-5-boronopentyl)-1H-tetrazol-1-yl)acetic acid hydrochloride. | >100 | |
| 251 | (5-amino-5-(1H-tetrazol-5-yl)hexyl)boronic acid hydrochloride. | >100 | |
| 252 | (6-amino-6-(1H-tetrazol-5-yl)hexyl)boronic acid hydrochloride. | >100 | |
| 253 | (5-amino-5-(1-(2-((2-fluorobenzyl)amino)-2-oxoethyl)-1H-tetrazol-5-yl)pentyl)boronic acid hydrochloride | 9.4 | 8 |

TABLE 1-continued

| Example No | IUPAC Name | rhArg I (IC$_{50}$) | rhArg II (IC$_{50}$) |
|---|---|---|---|
| 254 | (5-amino-5-(1-benzyl-1H-tetrazol-5-yl)pentyl)boronic acid hydrochloride. | 180 | |
| 255 | (5-(methylamino)-5-(1H-tetrazol-5-yl)pentyl)boronic acid hydrochloride. | >500 | |
| 256 | (5-amino-5-(1-(3-fluorobenzyl)-1H-tetrazol-5-yl)pentyl) boronic acid hydrochloride. | >100 | |
| 257 | (5-amino-5-(1-phenethyl-1H-tetrazol-5-yl)petyl)boronic acid hydrochloride | >100 | |
| 258 | (5-amino-5-(1-cyclohexyl-1H-tetrazol-5-yl)pentyl)boronic acid hydrochloride. | >100 | |
| 259 | (5-amino-5-(1H-tetrazol-5-yl)pentyl)boronic acid hydrochloride. | >500 | |
| 260 | (5-amino-5-(1-(2-(benzylamino)-2-oxoethyl)-1H-tetrazol-5-yl)pentyl)boronic acid hydrochloride | 40 | |
| 261 | (5-(1-(2-fluoro-5-nitrophenyl)-1H-tetrazol-5-yl)-5-morpholinopentyl)boronicacid hydrochloride. | >500 | |
| 262 | (5-amino-5-(1-(2-morpholino-5-nitrophenyl)-1H-tetrazol-5-yl)pentyl)boronicacid hydrochloride. | >500 | |
| 262 | 5-amino-5-(1H-tetrazol-5-yl)hexyl)boronicacid hydrochloride. | >100 | |
| 263 | (5-amino-5-(1-(2-((4-chlorobenzyl)amino)-2-oxoethyl)-1H-tetrazol-5-yl)pentyl)boronic acid hydrochloride | 14 | 7 |
| 264 | (5-amino-5-(1-(2-oxo-2-(((S)-1-phenylethyl)amino)ethyl)-1H-tetrazol-5-yl)pentyl)boronic acid hydrochloride | 13 | |
| 265 | (5-amino-5-(1-(2-oxo-2-((thiophen-2-ylmethyl)amino)ethyl)-1H-tetrazol-5-yl)pentyl)boronic acid hydrochloride | 23 | |
| 266 | (5-Amino-5-(1-(2-oxo-2-(phenethylamino)ethyl)-1H-tetrazol-5-yl)pentyl)boronic acid hydrochloride | 15 | 13 |
| 267 | (5-amino-5-(1-(2-((1-benzylpiperidin-4-yl)amino)-2-oxoethyl)-1H-tetrazol-5-yl)pentyl)boronic acid hydrochloride. | 248 | |
| 268 | (5-amino-5-(1-(2-(cyclopropylamino)-2-oxoethyl)-1H-tetrazol-5-yl)pentyl)boronic acid hydrochloride. | 21 | |
| 269 | (5-amino-5-(1-(2-((2-morpholinoethyl)amino)-2-oxoethyl)-1H-tetrazol-5-yl)pentyl)boronic acid hydrochloride. | >500 | |
| 270 | (5-amino-5-(1-(2-((3,4-dimethoxyphenethyl)amino)-2-oxoethyl)-1H-tetrazol-5-yl)pentyl)boronic acid hydrochloride. | 29 | |
| 271 | (5-amino-5-(1-(2-(butylamino)-2-oxoethyl)-1H-tetrazol-5-yl)pentyl)boronic acid hydrochloride. | 14 | |
| 272 | (5-amino-5-(1-(2-oxo-2-(prop-2-yn-1-ylamino)ethyl)-1H-tetrazol-5-yl)pentyl)boronic acid hydrochloride. | 17 | 12 |
| 273 | (5-amino-5-(1-(2-(4-benzylpiperazin-1-yl)-2-oxoethyl)-1H-tetrazol-5-yl)pentyl)boronic acid hydrochloride. | >500 | |
| 274 | (5-amino-5-(1-(2-morpholino-2-oxoethyl)-1H-tetrazol-5-yl)pentyl)boronic acid hydrochloride | 340 | |
| 275 | (5-amino-5-(1-(2-oxo-2-(pyrrolidin-1-yl)ethyl)-1H-tetrazol-5-yl)pentyl)boronic acid hydrochloride. | 448 | |
| 276 | (5-amino-5-(1-(2-((3-chlorobenzyl)amino)-2-oxoethyl)-1H-tetrazol-5-yl)pentyl)boronic acid hydrochloride. | 50 | |
| 277 | (5-amino-5-(1-(2-((2-chlorobenzyl)amino)-2-oxoethyl)-1H-tetrazol-5-yl)pentyl)boronic acid hydrochloride. | 55 | |
| 278 | (5-amino-5-(1-(2-oxo-2-((pyridin-3-ylmethyl)amino)ethyl)-1H-tetrazol-5-yl)pentyl)boronic acid hydrochloride. | 58 | |
| 279 | (5-amino-5-(1-(2-((4-methoxybenzyl)amino)-2-oxoethyl)-1H-tetrazol-5-yl)pentyl)boronic acid hydrochloride. | 45 | |
| 280 | (5-amino-5-(1-(2-oxo-2-((pyridin-4-ylmethyl)amino)ethyl)-1H-tetrazol-5-yl)pentyl)boronic acid hydrochloride. | 65 | |
| 281 | (5-amino-5-(1-(3-((4-chlorobenzyl)amino)-3-oxopropyl)-1H-tetrazol-5-yl)pentyl)boronic acid hydrochloride | 70 | |
| 282 | (5-amino-5-(1-(3-oxo-3-(phenethylamino)propyl)-1H-tetrazol-5-yl)pentyl)boronic acid hydrochloride. | 110 | |
| 283 | 4-(5-(1-amino-5-boronopentyl)-1H-tetrazol-1-yl)butanoic acid hydrochloride | 250 | |
| 284 | (5-(1-(2-(1H-indol-3-yl)ethyl)-1H-tetrazol-5-yl)-5-aminopentyl)boronic acid hydrochloride. | 115 | |
| 285 | (5-amino-5-(1-(2-(benzyl(2-hydroxyethyl)amino)-2-oxoethyl)-1H-tetrazol-5-yl)pentyl)boronic acid hydrochloride. | 155 | |
| 286 | (5-amino-5-(1-(2-(benzyl(methyl)amino)-2-oxoethyl)-1H-tetrazol-5-yl)pentyl)boronic acid hydrochloride. | 80 | |
| 287 | (5-amino-5-(1-(2-(((S)-1-(4-chlorophenyl)ethyl)amino)-2-oxoethyl)-1H-tetrazol-5-yl)pentyl)boronic acid hydrochloride. | 35 | |
| 288 | (5-amino-5-(1-(1-phenylethyl)-1H-tetrazol-5-yl)pentyl)boronic acid hydrochloride. | 210 | |
| 289 | (5-amino-5-(1-((S)-1-phenylethyl)-1H-tetrazol-5-yl)pentyl)boronic acid hydrochloride. | 155 | |
| 290 | (5-amino-5-(1-((R)-1-phenylethyl)-1H-tetrazol-5-yl)pentyl)boronic acid hydrochloride. | <101 | |
| 291 | (5-amino-5-(1-((S)-1-(4-chlorophenyl)ethyl)-1H-tetrazol-5-yl)pentyl)boronic acid hydrochloride. | <101 | |
| 292 | (5-amino-5-(1-((R)-1-(4-chlorophenyl)ethyl)-1H-tetrazol-5-yl)pentyl)boronic acid hydrochloride. | <101 | |
| 293 | (5-amino-5-(1-((R)-1-(4-methoxyphenyl)ethyl)-1H-tetrazol-5-yl)pentyl)boronic acid hydrochloride. | <101 | |
| 294 | (5-amino-5-(1-(4-fluorobenzyl)-1H-tetrazol-5-yl)pentyl)boronic acid hydrochloride. | <101 | |
| 295 | (5-amino-5-(1-(2-fluorobenzyl)-1H-tetrazol-5-yl)pentyl)boronic acid hydrochloride. | <101 | |
| 296 | (5-amino-5-(1-(3-chlorobenzyl)-1H-tetrazol-5-yl)pentyl)boronic acid hydrochloride. | <101 | |
| 297 | (5-amino-5-(1-(2-chlorobenzyl)-1H-tetrazol-5-yl)pentyl)boronic acid hydrochloride. | <101 | |
| 298 | (5-amino-5-(1-(4-bromobenzyl)-1H-tetrazol-5-yl)pentyl)boronic acid hydrochloride. | <101 | |
| 299 | (5-amino-5-(1-(4-cyanobenzyl)-1H-tetrazol-5-yl)pentyl)boronic acid hydrochloride. | <101 | |
| 300 | (5-amino-5-(1-(2,4-dichlorobenzyl)-1H-tetrazol-5-yl)pentyl)boronic acid hydrochloride. | <101 | |
| 301 | (5-amino-5-(1-(3,4-dichlorobenzyl)-1H-tetrazol-5-yl)pentyl)boronic acid hydrochloride. | <101 | |
| 302 | (5-amino-5-(1-(4-bromo-2-fluorobenzyl)-1H-tetrazol-5-yl)pentyl)boronic acid hydrochloride. | <101 | |

TABLE 1-continued

| Example No | IUPAC Name | rhArg I (IC$_{50}$) | rhArg II (IC$_{50}$) |
|---|---|---|---|
| 303 | (5-amino-5-(1-(2-methoxybenzyl)-1H-tetrazol-5-yl)pentyl)boronic acid hydrochloride. | <101 | |
| 304 | (5-amino-5-(1-(3-hydroxy-1-phenylpropyl)-1H-tetrazol-5-yl)pentyl)boronic acid hydrochloride. | <101 | |
| 305 | (5-amino-5-(1-(pyridin-3-ylmethyl)-1H-tetrazol-5-yl)pentyl)boronic acid hydrochloride. | <101 | |
| 306 | (5-amino-5-(1-(thiophen-2-ylmethyl)-1H-tetrazol-5-yl)pentyl)boronic acid hydrochloride. | <101 | |
| 307 | (5-amino-5-(1-(4-fluorophenethyl)-1H-tetrazol-5-yl)pentyl)boronic acid hydrochloride. | <101 | |
| 308 | (5-amino-5-(1-(3,4-dimethoxyphenethyl)-1H-tetrazol-5-yl)pentyl)boronic acid hydrochloride. | <101 | |
| 309 | (5-amino-5-(1-(2-methoxyphenethyl)-1H-tetrazol-5-yl)pentyl)boronic acid hydrochloride. | <101 | |
| 310 | (5-amino-5-(1-(4-hydroxyphenethyl)-1H-tetrazol-5-yl)pentyl)boronic acid hydrochloride. | <101 | |
| 311 | (5-amino-5-(1-(3-methoxyphenethyl)-1H-tetrazol-5-yl)pentyl)boronic acid hydrochloride. | <101 | |
| 312 | (5-amino-5-(1-(3-phenylpropyl)-1H-tetrazol-5-yl)pentyl)boronic acid hydrochloride. | <101 | |
| 313 | (5-amino-5-(1-(4-bromophenethyl)-1H-tetrazol-5-yl)pentyl)boronic acid hydrochloride. | <101 | |
| 314 | (5-amino-5-(1-(2,5-difluorobenzyl)-1H-tetrazol-5-yl)pentyl)boronic acid hydrochloride. | <101 | |
| 315 | (5-amino-5-(1-(2-((2,4-difluorobenzyl)amino)-2-oxoethyl)-1H-tetrazol-5-yl)pentyl)boronic acid hydrochloride. | 9.1 | |
| 316 | (5-amino-5-(1-(2-((4-methylbenzyl)amino)-2-oxoethyl)-1H-tetrazol-5-yl)pentyl)boronic acid hydrochloride. | 33 | |
| 317 | (5-amino-5-(1-(2-((4-chlorophenethyl)amino)-2-oxoethyl)-1H-tetrazol-5-yl)pentyl)boronic acid hydrochloride. | 75 | |
| 318 | (5-amino-5-(1-(2-((4-chloro-2-fluorobenzyl)amino)-2-oxoethyl)-1H-tetrazol-5-yl)pentyl)boronic acid hydrochloride. | 15.5 | 18.6 |
| 319 | (5-amino-5-(1-(2-((2,6-difluorobenzyl)amino)-2-oxoethyl)-1H-tetrazol-5-yl)pentyl)boronic acid hydrochloride. | 12.4 | |
| 320 | (5-amino-5-(1-(2-((4-cyanobenzyl)amino)-2-oxoethyl)-1H-tetrazol-5-yl)pentyl)boronic acid hydrochloride. | 43 | |
| 321 | (5-amino-5-(1-(1-((4-chlorobenzyl)amino)-3-methyl-1-oxobutan-2-yl)-1H-tetrazol-5-yl)pentyl)boronic acid hydrochloride. | 150 | |
| 322 | (5-amino-5-(1-(1-((4-chlorobenzyl)amino)-4-methyl-1-oxopentan-2-yl)-1H-tetrazol-5-yl)pentyl)boronic acid hydrochloride | 110 | |
| 323 | (5-amino-5-(1-(2-((4-bromobenzyl)amino)-2-oxoethyl)-1H-tetrazol-5-yl)pentyl)boronic acid hydrochloride. | 55 | |
| 324 | (6-amino-6-(1-(2-(benzylamino)-2-oxoethyl)-1H-tetrazol-5-yl)hexyl)boronic acid hydrochloride. | 120 | |
| 325 | (6-amino-6-(1-(2-((4-chlorobenzyl)amino)-2-oxoethyl)-1H-tetrazol-5-yl)hexyl)boronic acid hydrochloride | 7.8 | |
| 326 | (6-amino-6-(1-(2-((2,4-dichlorobenzyl)amino)-2-oxoethyl)-1H-tetrazol-5-yl)hexyl)boronic acid hydrochloride. | 13 | |
| 327 | (6-amino-6-(1-(2-oxo-2-(prop-2-yn-1-ylamino)ethyl)-1H-tetrazol-5-yl)hexyl)boronic acid hydrochloride. | 38 | |
| 328 | (6-amino-6-(1-(2-oxo-2-(phenethylamino)ethyl)-1H-tetrazol-5-yl)hexyl)boronic acid hydrochloride. | <110 | |
| 329 | (5-amino-5-(1-(2-oxo-2-(((perfluorophenyl)methyl)amino)ethyl)-1H-tetrazol-5-yl)pentyl)boronic acid hydrochloride. | 16.8 | |
| 330 | (5-amino-5-(1-(2-oxo-2-((2,3,4,5-tetrafluorobenzyl)amino)ethyl)-1H-tetrazol-5-yl)pentyl)boronic acid hydrochloride. | 13 | |
| 331 | (5-amino-5-(1-(2-oxo-2-((2,4,6-trifluorobenzyl)amino)ethyl)-1H-tetrazol-5-yl)pentyl)boronic acid hydrochloride. | 12.5 | |
| 332 | (5-amino-5-(1-(2-(((6-chloropyridin-3-yl)methyl)amino)-2-oxoethyl)-1H-tetrazol-5-yl)pentyl)boronic acid hydrochloride. | 5.5 | |
| 333 | (5-amino-5-(1-(2-((3-fluorobenzyl)amino)-2-oxoethyl)-1H-tetrazol-5-yl)pentyl)boronic acid hydrochloride. | 10.6 | |
| 334 | (5-amino-5-(1-(2-((2,3-difluorobenzyl)amino)-2-oxoethyl)-1H-tetrazol-5-yl)pentyl)boronic acid hydrochloride. | 11.5 | 56 |
| 335 | (5-amino-5-(1-(2-((2,5-difluorobenzyl)amino)-2-oxoethyl)-1H-tetrazol-5-yl)pentyl)boronic acid. hydrochloride. | 13 | |
| 336 | (5-amino-5-(1-(2-((3,5-difluorobenzyl)amino)-2-oxoethyl)-1H-tetrazol-5-yl)pentyl)boronic acid hydrochloride. | 19 | |
| 337 | (5-amino-5-(1-(2-oxo-2-((2,3,4-trifluorobenzyl)amino)ethyl)-1H-tetrazol-5-yl)pentyl)boronic acid hydrochloride. | 49 | |
| 338 | (5-amino-5-(1-(2-oxo-2-((2,3,5-trifluorobenzyl)amino)ethyl)-1H-tetrazol-5-yl)pentyl)boronic acid hydrochloride. | 43 | |
| 339 | (5-amino-5-(1-(2-oxo-2-((3,4,5-trifluorobenzyl)amino)ethyl)-1H-tetrazol-5-yl)pentyl)boronic acid hydrochloride. | 56 | |
| 340 | (5-amin o-5-(1-(2-oxo-2-((2,3,6-trifluorobenzyl)amino)ethyl)-1H-tetrazol-5-yl)pentyl)boronic acid hydrochloride. | | |
| 341 | (5-amino-5-(1-(2-oxo-2-((2,3,5,6-tetrafluorobenzyl)amino)ethyl)-1H-tetrazol-5-yl)pentyl)boronic acid hydrochloride. | 33 | |
| 342 | (5-amino-5-(1-(2-((3,4-difluorobenzyl)amino)-2-oxoethyl)-1H-tetrazol-5-yl)pentyl)boronic acid hydrochloride. | 51 | |
| 343 | (5-amino-5-(1-(2-oxo-2-((2,4,5-trifluorobenzyl)amino)ethyl)-1H-tetrazol-5-yl)pentyl)boronic acid hydrochloride. | 15 | |
| 344 | (5-amino-5-(1-((1-(4-chlorobenzyl)piperidin-4-yl)methyl)-1H-tetrazol-5-yl)pentyl)boronic acid hydrochloride. | 24 | |
| 345 | (5-amino-5-(1-(2-oxo-2-(((R)-1-phenylethyl)amino)ethyl)-1H-tetrazol-5-yl)pentyl)boronic acid hydrochloride. | 15 | |
| 346 | (5-amino-5-(1-(2-(((1-(2-fluoroethyl)-1H-1,2,3-triazol-4-yl)methyl)amino)-2-oxoethyl)-1H-tetrazol-5-yl)pentyl)boronic acid hydrochloride. | 23 | |

TABLE 1-continued

| Example No | IUPAC Name | rhArg I (IC$_{50}$) | rhArg II (IC$_{50}$) |
|---|---|---|---|
| 347 | (5-amino-5-(1-(2-(4-chlorobenzamido)ethyl)-1H-tetrazol-5-yl)pentyl)boronic acid hydrochloride | 95 | |
| 348 | (5-amino-5-(1-(2-(((1-(4-chlorobenzyl)-1H-1,2,3-triazol-4-yl)methyl)amino)-2-oxoethyl)-1H-tetrazol-5-yl)pentyl)boronic acid hydrochloride | 27 | |
| 349 | (5-(1-(2-((4-chlorobenzyl)amino)-2-oxoethyl)-1H-tetrazol-5-yl)-5-((pyridin-4-ylmethyl)amino)pentyl)boronic acid hydrochloride. | 120 | |
| 350 | (5-(4-(aminomethyl)piperidin-1-yl)-5-(1-(2-((4-chlorobenzyl)amino)-2-oxoethyl)-1H-tetrazol-5-yl)pentyl)boronic acid hydrochloride. | 150 | |
| 351 | (5-(1-(2-((4-chlorobenzyl)amino)-2-oxoethyl)-1H-tetrazol-5-yl)-5-((1-methylpiperidin-4-yl)amino)pentyl)boronic acid hydrochloride. | 250 | |
| 352 | (5-(1-(2-(((1,1'-biphenyl]-4-ylmethyl)amino)-2-oxoethyl)-1H-tetrazol-5-yl)-5-aminopentyl)boronic acid. | 250 | |
| 353 | (5-(1-(2-(((6-(1H-imidazol-1-yl)pyridin-3-yl)methyl)amino)-2-oxoethyl)-1H-tetrazol-5-yl)-5-aminopentyl)boronic acid hydrochloride. | 130 | |
| 354 | (5-amino-5-(1-(2-((4-chlorophenyl)amino)-2-oxoethyl)-1H-tetrazol-5-yl)pentyl)boronic acid hydrochloride. | 255 | |
| 355 | (+)-(R)-(5-amino-5-(1-(2-oxo-2-(prop-2-yn-1-ylamino)ethyl)-1H-tetrazol-5-yl)pentyl)boronic acid hydrochloride. | 15 | 30 |
| 356 | (−)-(S)-(5-amino-5-(1-(2-oxo-2-(prop-2-yn-1-ylamino)ethyl)-1H-tetrazol-5-yl)pentyl)boronic acid hydrochloride. | 28 | 35 |
| 357 | (+)-(R)-(5-amino-5-(1-(2-((4-chlorobenzyl)amino)-2-oxoethyl)-1H-tetrazol-5-yl)pentyl)boronic acid hydrochloride. | 55 | 137 |
| 358 | (−)-(S)-(5-amino-5-(1-(2-((4-chlorobenzyl)amino)-2-oxoethyl)-1H-tetrazol-5-yl)pentyl)boronic acid hydrochloride. (SHK227) | 12 | 6 |
| 359 | (+)-(R)-(5-amino-5-(1-(2-((2-fluorobenzyl)amino)-2-oxoethyl)-1H-tetrazol-5-yl)pentyl)boronic acid hydrochloride. (SHK242) | 3.4 | 2.9 |
| 360 | (−)-(S)-(5-amino-5-(1-(2-((2-fluorobenzyl)amino)-2-oxoethyl)-1H-tetrazol-5-yl)pentyl)boronic acid hydrochloride. | 36.4 | 5 |
| 361 | (+)-(R)-(5-amino-5-(1-(2-oxo-2-(phenethylamino)ethyl)-1H-tetrazol-5-yl)pentyl)boronic acid hydrochloride. (SHK277) | 10.5 | 4.0 |
| 362 | (−)-(S)-(5-amino-5-(1-(2-oxo-2-(phenethylamino)ethyl)-1H-tetrazol-5-yl)pentyl)boronic acid hydrochloride. | 13.2 | 10.2 |
| 363 | (5-amino-5-(1-(2-((4-fluorobenzyl)amino)-2-oxoethyl)-1H-tetrazol-5-yl)pentyl)boronic acid hydrochloride. | 34 | |
| 364 | (5-amino-5-(1-(5-amino-2-fluorophenyl)-1H-tetrazol-5-yl)pentyl)boronic acid hydrochloride. | 250 | |
| 365 | 5-amino-5-(1-(5-amino-2-morpholinophenyl)-1H-tetrazol-5-yl)pentyl)boronic acid hydrochloride. | 300 | |
| 366 | (5-amino-5-(1-(5-amino-2-(1,1-dioxidothiomorpholino)phenyl)-1H-tetrazol-5-yl)pentyl)boronic acid hydrochloride. | 200 | |

Further data for some compounds of the present invention is disclosed in Van den Berg M. P. M. et al. "Pharmacological screening identifies SHK242 and SHK277 as novel arginase inhibitors with efficacy against allergen-induced airway narrowing in vitro and in vivo" Journal of Pharmacology and Experimental Therapeutics Apr. 13, 2020, jpet.119.264341; DOI: 10.1124/jpet.119.264341.

The invention claimed is:

1. A compound of formula (I):

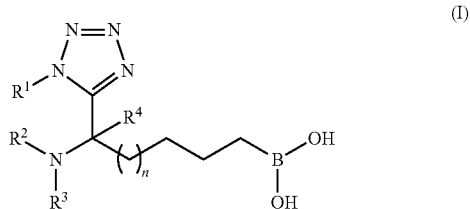

wherein n is 1 or 2;

$R^1$ is hydrogen or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted;

$R^2$ is hydrogen or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted, and $R^3$ is hydrogen; or $R^2$ and $R^3$ together are part of an optionally substituted heterocycloalkyl or heteroaryl group; and $R^4$ is hydrogen or methyl;

or a pharmaceutically acceptable salt, solvate or hydrate or a pharmaceutically acceptable formulation thereof.

2. The compound according to claim 1, wherein $R^4$ is hydrogen.

3. The compound according to claim 1, wherein $R^2$ and $R^3$ are hydrogen.

4. The compound according to claim 1, wherein $R^1$ is a group of formula —CH$_2$—C(=O)—NH—R$^5$, a group of formula —CH$_2$—CH$_2$—C(=O)—NH—R$^5$, or a group of formula —CH$_2$—C(=O)—N(CH$_3$)—R$^5$, wherein $R^5$ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted.

5. The compound according to claim 1, wherein $R^1$ is a group of formula -L$^1$-Cy$^1$-L$^2$-Cy$^2$, wherein L$^1$ and L$^2$ are independently selected from a bond, a C$_{1-4}$ alkyl group or a C$_{1-4}$ heteroalkyl group;

Cy$^1$ is a C$_{3-7}$ cycloalkylene group, a heterocycloalkylene group containing from 3 to 7 ring atoms selected from O, S, N and C, a phenylene group or a heteroarylene group containing 5 or 6 ring atoms selected from O, S, N and C, all of which groups may optionally be substituted; and Cy$^2$ is a C$_{3-7}$ cycloalkyl group, a heterocycloalkyl group containing from 3 to 7 ring atoms selected from O, S, N and C, a phenyl group or a heteroaryl group containing 5 or 6 ring atoms selected from O, S, N and C, all of which groups may optionally be substituted.

6. The compound according to claim 1, having the following formula (II):

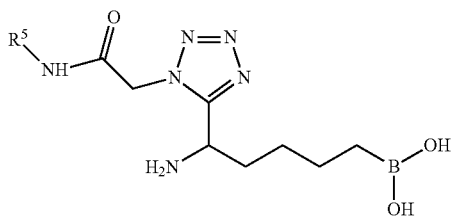

(II)

wherein R⁵ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted;

or a pharmaceutically acceptable salt, solvate or hydrate or a pharmaceutically acceptable formulation thereof.

7. The compound according to claim 1, having the following formula (III):

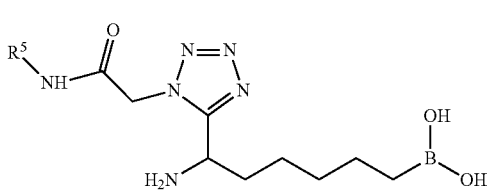

(III)

wherein R⁵ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted;

or a pharmaceutically acceptable salt, solvate or hydrate or a pharmaceutically acceptable formulation thereof.

8. The compound according to claim 4, wherein R⁵ is a group of formula —CH₂—R⁶, —CH₂CH₂—R⁶ or —CH(CH₃)—R⁶ wherein R⁶ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted.

9. The compound according to claim 8, wherein R⁶ is a $C_{1-4}$ alkyl, a $C_{2-4}$ alkenyl, a $C_{2-4}$ alkynyl or a $C_{1-4}$ heteroalkyl group.

10. The compound according to claim 8, wherein R⁶ is selected from the following groups, all of which may optionally be substituted: $C_{3-7}$ cycloalkyl, phenyl, heterocycloalkyl containing from 3 to 7 ring atoms selected from C, N, O and S and heteroaryl containing 5 or 6 ring atoms selected from C, N, O and S.

11. A pharmaceutical composition comprising a compound according to claim 1 or a pharmaceutically acceptable salt, solvate or hydrate thereof, optionally in combination with a pharmaceutically acceptable carrier and/or adjuvant.

12. A method of treating a disease that is associated with arginase activity, comprising administering a compound of claim 1.

13. The compound according to claim 6, wherein R⁵ is a group of formula —CH₂—R⁶, —CH₂CH₂—R⁶ or —CH(CH₃)—R⁶ wherein R⁶ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted.

14. The compound according to claim 13, wherein R⁶ is a $C_{1-4}$ alkyl, a $C_{2-4}$ alkenyl, a $C_{2-4}$ alkynyl or a $C_{1-4}$ heteroalkyl group.

15. The compound according to claim 13, wherein R⁶ is selected from the following groups, all of which may optionally be substituted: $C_{3-7}$ cycloalkyl, phenyl, heterocycloalkyl containing from 3 to 7 ring atoms selected from C, N, O and S and heteroaryl containing 5 or 6 ring atoms selected from C, N, O and S.

16. The compound according to claim 7, wherein R⁵ is a group of formula —CH₂—R⁶, —CH₂CH₂—R⁶ or —CH(CH₃)—R⁶ wherein R⁶ is an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted.

17. The compound according to claim 16, wherein R⁶ is a $C_{1-4}$ alkyl, a $C_{2-4}$ alkenyl, a $C_{2-4}$ alkynyl or a $C_{1-4}$ heteroalkyl group.

18. The compound according to claim 16, wherein R⁶ is selected from the following groups, all of which may optionally be substituted: $C_{3-7}$ cycloalkyl, phenyl, heterocycloalkyl containing from 3 to 7 ring atoms selected from C, N, O and S and heteroaryl containing 5 or 6 ring atoms selected from C, N, O and S.

19. The method of claim 12, wherein the disease is asthma, COPD and allergic rhinitis.

* * * * *